US 8,182,786 B2

(12) United States Patent
O'Brien et al.

(10) Patent No.: US 8,182,786 B2
(45) Date of Patent: May 22, 2012

(54) NANO-SIZED PARTICLES, PROCESSES OF MAKING, COMPOSITIONS AND USES THEREOF

(75) Inventors: Stephen O'Brien, New York, NY (US); Ming Yin, Los Alamos, NM (US)

(73) Assignee: The Trustees of Columbia University in the City of New York, New York, NY (US)

(*) Notice: Subject to any disclaimer, the term of this patent is extended or adjusted under 35 U.S.C. 154(b) by 1210 days.

(21) Appl. No.: 11/451,251

(22) Filed: Jun. 12, 2006

(65) Prior Publication Data
US 2007/0140951 A1   Jun. 21, 2007

Related U.S. Application Data

(63) Continuation-in-part of application No. PCT/US2004/041141, filed on Dec. 9, 2004.

(60) Provisional application No. 60/528,667, filed on Dec. 11, 2003.

(51) Int. Cl.
C01G 49/02 (2006.01)
(52) U.S. Cl. ........................ 423/632; 423/633
(58) Field of Classification Search .................. 423/632, 423/633
See application file for complete search history.

(56) References Cited

U.S. PATENT DOCUMENTS

| | | | |
|---|---|---|---|
| 4,649,037 A | 3/1987 | Marsh et al. |
| 4,705,762 A | 11/1987 | Ota et al. |
| 5,133,974 A | 7/1992 | Paradissis et al. |
| 5,618,475 A | 4/1997 | Johnson et al. |
| 5,665,277 A | 9/1997 | Johnson et al. |
| 5,716,565 A | 2/1998 | Stangle et al. |
| 5,733,895 A | 3/1998 | Forestier et al. |
| 5,766,635 A | 6/1998 | Spenleuhauer et al. |
| 5,783,263 A | 7/1998 | Majetich et al. |
| 5,840,111 A | 11/1998 | Wiederhoft et al. |
| 5,879,715 A | 3/1999 | Higgins et al. |
| 5,885,596 A | 3/1999 | Parab |
| 5,948,483 A | 9/1999 | Kim et al. |
| 5,952,125 A | 9/1999 | Bi et al. |
| 5,958,329 A | 9/1999 | Brown |
| 6,036,886 A | 3/2000 | Chhabra et al. |
| 6,048,515 A | 4/2000 | Kresse et al. |
| 6,136,156 A | 10/2000 | El-Shall et al. |
| 6,143,211 A | 11/2000 | Mathiowitz et al. |
| 6,162,530 A | 12/2000 | Xiao et al. |
| 6,168,798 B1 | 1/2001 | O'Halloran et al. |
| 6,197,757 B1 | 3/2001 | Perrier et al. |
| 6,200,680 B1 | 3/2001 | Takeda et al. |
| 6,262,129 B1 | 7/2001 | Murray et al. |
| 6,302,940 B2 | 10/2001 | Murray et al. |
| 6,403,653 B1 | 6/2002 | Hobson et al. |
| 6,416,818 B1 | 7/2002 | Aikens et al. |
| 6,416,862 B1 | 7/2002 | Kogoi et al. |
| 6,420,437 B1 | 7/2002 | Mori et al. |
| 6,440,213 B1 | 8/2002 | Alivisatos et al. |
| 6,451,220 B1 | 9/2002 | Ziolo et al. |
| 6,458,431 B2 | 10/2002 | Hill et al. |
| 6,506,493 B1 | 1/2003 | Kumar et al. |
| 6,514,481 B1 | 2/2003 | Prasad et al. |
| 6,514,767 B1 | 2/2003 | Natan |
| 6,514,772 B2 | 2/2003 | Siiman et al. |
| 6,517,802 B1 | 2/2003 | Xiao et al. |
| 6,530,944 B2 | 3/2003 | West et al. |
| 6,548,168 B1 | 4/2003 | Mulvaney et al. |
| 6,562,318 B1 | 5/2003 | Filler |
| 6,592,903 B2 | 7/2003 | Ryde et al. |
| 6,592,945 B2 | 7/2003 | Suzuki et al. |
| 6,605,565 B1 | 8/2003 | Zhang et al. |
| 6,616,869 B2 | 9/2003 | Mathiowitz et al. |
| 6,623,761 B2 | 9/2003 | Hassan |
| 7,407,527 B2 * | 8/2008 | Hyeon ............................ 75/351 |
| 2004/0161380 A1 | 8/2004 | Zimehl et al. |
| 2006/0264520 A1 | 11/2006 | Sonezaki et al. |
| 2009/0297626 A1 | 12/2009 | O'Brien et al. |

FOREIGN PATENT DOCUMENTS

WO   WO-2004087577 A1   10/2004

OTHER PUBLICATIONS

"PCT Application No. PCT/US2004/041141, International Search Report mailed Jul. 27, 2005", 2 pgs.
Amekura, H., et al., "Reconfirmation With Discussions of Anomalies in Photoconductivity of Cu₂O at Low Temperatures", *Journal of the Physical Society of Japan*, 64(7), (1995), 2684-2696.
Ayyub, P., et al., "Effect of Crystal Size Reduction on Lattice Symmetry and Cooperative Properties", *Physical Review B*, 51(9), (1995), 6135-6138.
Bohannan, E. W., et al., "Epitaxial Electrodeposition of Copper(I) Oxide on Single-Crystal Gold(100)", *Chemistry of Materials*, 11(9), (1999), 2289-2291.
Borgohain, K., et al., "Synthesis and Properties of Cu₂O Quantum Particles", *Journal of Applied Physics*, 92(3), (2002), 1292-1297.
Caswell, N., et al., "Physical Origin of the Anomalous Temperature Dependence of the 1S Yellow Exciton Luminescence Intensity in Cu₂O", *Physical Review B*, 25(8), (1982), 5519-5522.
Deki, S., et al., "Preparation and Characterization of Copper(I) Oxide Nanoparticles Dispersed in a Polymer Matrix", *Journal of Materials Chemistry*, 8(8), (1998), 1865-1868.
Dong, Y., et al., "Preparation of Cuprous Oxide Particles of Different Crystallinity", *Journal of Colloid Interface Science*, 243, (2001), 85-89.
Gastev, S. V., et al., "Relaxed Excitons in Cu₂O", *Solid State Communications*, 42(5), (1982), 389-391.

(Continued)

Primary Examiner — Edward Johnson
(74) Attorney, Agent, or Firm — Schwegman, Lundberg & Woessner, P.A.

(57) ABSTRACT

The present invention describes methods for preparing high quality nanoparticles, i.e., metal oxide based nanoparticles of uniform size and monodispersity. The nanoparticles advantageously comprise organic alkyl chain capping groups and are stable in air and in nonpolar solvents. The methods of the invention provide a simple and reproducible procedure for forming transition metal oxide nanocrystals, with yields over 80%. The highly crystalline and monodisperse nanocrystals are obtained directly without further size selection; particle size can be easily and fractionally increased by the methods. The resulting nanoparticles can exhibit magnetic and/or optical properties. These properties result from the methods used to prepare them. Also advantageously, the nanoparticles of this invention are well suited for use in a variety of industrial applications, including cosmetic and pharmaceutical formulations and compositions.

48 Claims, 56 Drawing Sheets

OTHER PUBLICATIONS

Goto, T., et al., "Bose-Einstein Statistics of Orthoexcitons Generated by Two-Photon Resonant Absorption in Cuprous Oxide", *Physical Review B*, 55(12), (1997), 7609-7614.

Gou, L., et al., "Solution-Phase Synthesis of $Cu_2O$ Nanocubes", *Nano Letters*, 3(2), (2003), 231-234.

Herhold, A. B., et al., "Structural Transformations and Metastability in Semiconductor Nanocrystals", *Phase Transitions*, 68(1), (1999), 1-25.

Hyeon, T., et al., "Synthesis of Highly Crystalline and Monodisperse Maghemite Nanocystallites without a Size-Selection Process", *Journal of the American Chemical Society*, 123, (2001), 12798-12801.

Lifshitz, I. M., et al., "The Kinetics of Precipitation From Supersaturated Solid Solutions", *J. Phys. Chem. Solids*, 19(½), (1961), 35-50.

McFadyen, P., et al., "Copper Hydrous Oxide Sols of Uniform Particle Shape and Size", *Journal of Colloid and Interface Science*, 44(1), (1973), 95-106.

Muramatsu, A., "Synthesis of Uniform Spherical $Cu_2O$ Particles from Condensed CuO Suspensions", *Journal of Colloid and Interface Science*, 189, (1997), 167-173.

Musa, A. O., et al., "Production of Cuprous Oxide, a Solar Cell Material, by Thermal Oxidation and a Study of its Physical and Electrical Properties", *Solar Energy Materials and Solar Cells*, 51(3-4), (1998),305-316.

Oskam, G., et al., "The Growth Kinetics of $TiO_2$ Nanoparticles from Titanium(IV) Alkoxide at High Water/Titanium Ratio", *J. Phys. Chem. B.*, 107, (2003), 1734-1738.

Palkar, V. R., et al., "Size-Induced Structural Transitions in the Cu-O and Ce-O Systems", *Physical Review B*, 53(5), (1996), 2167-2170.

Park, J., et al., "Ultra-Large-Scale Syntheses of Monodisperse Nanocrystals", *Nature Materials*, 3, (2004), 891-895.

Peng, X., et al., "Kinetics of II-VI and III-V Colloidal Semiconductor Nanocrystal Growth: "Focusing" of Size Distributions", *Journal of the American Chemical Society*, 120(21), (1998), 5343-5344.

Ponyatovskiĭ, E. G., et al., "Nanocrystalline $Cu_2O$ Prepared Under High Pressures", *Physics of the Solid State*, 44(5), (2002), 852-856.

Qadri, S. B., et al., "Size-Induced Transition-Temperature Reduction in Nanoparticles of ZuS", *Physical Review B*, 60(13), (1999),9191-9193.

Ram, S., et al., "Formation of Stable $Cu_2O$ Nanocrystals in a New Orthorhombic Crystal Structure", *Materials Science and Engineering*, A304-306, (2001), 805-809.

Redl, F. X., et al., "Three-Dimensional Binary Superlattices of Magnetic Nanocrystals and Semiconductor Quantum Dots", *Nature*, 423, (2003), 968-971.

Snoke, D. W., et al., "Carrier Thermalization in $Cu_2O$: Phonon Emission by Excitons", *Physical Review B*, 44(7), (1991), 2991-3000.

Snoke, D. W., et al., "Evidence for Bose-Einstein Condensation of Excitons in $Cu_2O$", *Physical Review B*, 41(16), (1990), 11171-11184.

Son, S. U., et al., "Synthesis of $Cu_2O$ Coated Cu Nanoparticles and Their Successful Applications to Ullmann-Type Amination Coupling Reactions of Aryl Chlorides", *Chemical Communication*, (2004),778-779.

Trebin, H.-R., et al., "Excitons in Cuprous Oxide Under Uniaxial Stress", *Physical Review B*, 23(2), (1981), 597-606.

Wagner, C., "Theorie der Alterung von Niederschäldgen durch Umlösen", *Z. Elektrochem.*, 65(⅞), (1961), 581-594.

Yin, M., et al., "Synthesis of Monodisperse Nanocrystals of Manganese Oxide", *Journal of the American Chemical Society*, 125(34), (2003), 10180-10181.

Yin, M., "Synthesis, Characterization and Properties of Nano-Sized Transition Metal Oxide", Doctoral Research Proposal, Doctor of Philosophy in the Graduate School of Arts and Science, Columbia University, (Apr. 14, 2003), 38 pgs.

Yin, M., et al., "Zinc Oxide Quantum Rods", *Journal of the American Chemical Society*, 126, (2004), 6206-6207.

"U.S. Appl. No. 11/982,842, Final Office Action mailed Mar. 16, 2011", 18 pgs.

"U.S. Appl. No. 11/982,842, Non-Final Office Action mailed Sep. 13, 2010", 12 pgs.

"U.S. Appl. No. 11/982,842, Response filed Jul. 8, 2011 to Final Office Action mailed Mar. 16, 2011", 16 pgs.

"U.S. Appl. No. 11/982,842, Response filed Dec. 13, 2010 to Non Final Office Action mailed Sep. 13, 2010", 16 pgs.

Ba, Jianhua, et al., "Nonaqueous Synthesis of Uniform Indium Tin Oxide Nanocrystals and Their Electrical Conductivity in Dependence of the Tin Oxide Concentration", *Chem. Mater.* 18, (2006), 2848-2854.

Niederberger, M., et al., "Benzyl Alcohol and Titanium Tetrachloride—A Versatile Reaction System for the Nonaqueous and Low-Temperature Preparation of Crystalline and Luminescent Titania Nanoparticles", *Chemical Materials*, 14(10), (2002), 4364-4370.

Spanhel, L., "Colloidal ZnO Nanostructures and Functional Coatings: A Survey", *Journal of Sol-Gel Science and Technology*, 39(1), (2006), 7-24.

Viswanatha, R., et al., "Synthesis and Characterization of Mn-Doped ZnO Nanocrystals", *J. Phys. Chem. B*, 108, (2004), 6303-6310.

Wakefield, G., et al., "Modified Titania Nanomaterials for Sunscreen Applications—Reducing Free Radical Generation and DNA Damage", *Materials Science and Technology*, 20(8), (2004), 985-988.

Zhang, H., et al., "Synthesis of Flower-Like ZnO Nanostructures by an Organic-Free Hydrothermal Process", *Nanotechnology*, 15, (2004), 622-626.

\* cited by examiner ized Particles, Processes of Making, Compositions and Uses Thereof This application is a continuation-in-part of International Application No. PCT/US2004/041141, filed Dec. 9, 2004, which claims the benefit of U.S. Provisional Patent Application No. 60/528,667, filed Dec. 11, 2003, each of which is incorporated herein by reference in its entirety.

The United States Government may have certain rights in the present invention pursuant to partial funding by grants from the Materials Research Science and Engineering Center (DMR-0213574 MRSEC) and the Nanoscale Science and Engineering Center (CHE-0117752 NSEC) of the National Science Foundation and pursuant to partial funding by the U.S. Department of Energy, Office of Basic Energy Sciences, through the Catalysis Futures grant DE-FG02-03ER15463, and in part by the (i) the MRSEC program of the National Science Foundation under award number DMR-0213574, and NSF-CAREER award, DMR-0348938.

This patent disclosure contains material which is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

FIELD OF THE INVENTION

The present invention relates generally to nanoparticles of transition metals, e.g., nanocrystals, their synthesis and characterization. More particularly, the invention relates to the synthesis of metal oxide nanoparticles that are monodisperse, uniform in size and stable. The nanoparticles of the present invention are safer and more environmentally benign than those prepared by previously described methods.

BACKGROUND OF THE INVENTION

Nanocrystals typically have a diameter of between 1 and 100 nm and may contain as few as a hundred or as many as tens of thousands of atoms having size-dependent properties and the possibility of arrangement in micro (and nano) assemblies. Nanocrystals have become the focus of intensive research due to their numerous applications in diverse fields such as catalyst production, ultramodern electronic and electrooptical devices, supermagnets, photographic suspensions, etc.

The development, characterization and exploitation of nanometer sized materials is an exceptionally active and rapidly expanding field. The exploration of complex structures on the nanometer size scale is underway in a variety of disciplines, such as chemistry, physics and engineering. The importance of such new interdisciplinary studies may be realized in the design and characterization of advanced materials. Studies of nanometer sized semiconductors, metals and refractories (nanoceramics) provide powerful examples of how control of particle size can optimize material performance.

The ability to engineer materials and assemble devices on the nanometer size scale is a goal in fields as diverse as opto-electronics, catalysis, ceramics and magnetic storage. To produce functional materials and devices, nanocrystals must be organized into solid superstructures while maintaining and enhancing their novel mesoscopic properties. In addition to this general requirement, there are formidable practical constraints. For example, materials must display mesoscopic phenomena at or near room temperature and be robust both chemically and mechanically. In addition, materials must be produced by cost effective methods. These challenges must be met to transform scientific curiosities into technological advances.

The applications of nano-sized particles in many aspects of industry and commercial products require efficient and economical ways to synthesize such particles that are of high quality and exhibit desired properties, e.g., magnetism and stability over time. Conventional techniques for nanoparticle production have typically been beset by drawbacks in the formation of uniformly-sized and chemically stable nanoparticle products, thus jeopardizing the reliability of the systems in which they are employed. Needed in the art are new methods that overcome existing problems for readily forming high quality and stable nanoparticles of several different metal oxides that exhibit desired properties for widespread use. Also needed are new and reliable types of metal oxide nanoparticle products with improved characteristics and properties for use in diverse applications. This present invention addresses and responds to these needs.

SUMMARY OF THE INVENTION

It is an aspect of the present invention to provide new methods of producing nanoparticles, such as metal oxide-based nanoparticles (also referred to as nanocrystals herein). The methods are economical and efficient, particularly due to the ready availability of starting material or metal precursors used in the methods. Through the practice of the methods, high-quality nanoparticles are formed having the characteristics of uniform size, monodispersity, stability (i.e., lack of degradation due, for example, to oxidation) as well as stability in non-polar solvents due to the presence of one or more non-polar capping groups at the surface, and magnetic properties. The methods are suitable for obtaining metal-based nanoparticles, particularly transition metal oxides, including for example and without limitation, zinc (Zn), iron (Fe), manganese (Mn), cobalt (Co), ruthenium (Ru), copper (Cu), scandium (Sc), titanium (Ti), vanadium (V), chromium (Cr), molybdenum (Mo), yttrium (Y), zirconium (Zr), hafnium (Hf), and nickel (Ni) metal-based nanoparticles.

It is another aspect of the present invention to provide new methods for the synthesis of nanocrystals to attain well-defined particle size and morphology. In accordance with this invention, a non-hydrolytic synthetic method is provided for effectively tailoring a uniform particle size and controlling the homogeneous dispersion of ultrafine metal oxide nanocrystals, e.g., iron oxide nanocrystals, zinc oxide nanocrystals and manganese oxide nanocrystals. Magnetic nanocrystals, and uses thereof, of metal oxides, e.g., manganese oxide, provide a particular aspect of this invention. In accordance with the invention, the method involves a non-aqueous environment, e.g., hydrocarbon-based solvents, in which anhydrous acetate precursors of a given metal are used. The use of a metal acetate starting material or precursor in such a solvent environment is a unique aspect of the present invention. The method further involves heating the metal acetate precursors, which are readily available and inexpensive, to a high temperature, e.g., greater than about 100° C. The metal acetate is then decomposed at high temperature in the presence of an organic solvent, e.g., trialkylamine, comprising at least one organic stabilizing ligand (also referred to as an organic stabilizer or organic ligand), e.g., oleic acid. The metal oxide nanoparticles are extracted at a temperature lower than that of the reaction temperature, e.g., room temperature, using a flocculating agent, e.g., a polar organic solvent, to precipitate the metal oxide nanoparticles into hydrocarbon solvent, such as an alkane. The metal oxide nanocrystals resulting from the methods of the invention are monodisperse, of uniform size, and are enclosed (packaged) in an organic outside layer or coating (e.g., ligand capped). Particular monodisperse metal oxide nanoparticles produced by the present methods include, without limitation, zinc oxide nanoparticles, manganese oxide nanoparticles, iron oxide nanoparticles and cupric oxide nanoparticles.

In a related aspect, the present invention provides a method of producing uniformed sized nanoparticles having useful properties, such as light reflecting and absorbing properties for use in preventative or therapeutic products and formulations to prevent, reduce, retard, ameliorate, or eliminate photodamage and/or photoaging in a human or animal due to exposure to sunlight. Such products and formulations are useful as sunscreens, suntan lotions and sunblocks, and as components thereof. The nanoparticles also may have magnetic properties, which are significantly different from the bulk material and which enhance their use in magnetic recording media, and read and write heads, as well as in a number of imaging, optical and electrical methods and devices. As but one example, the nanoparticles find use in the area of electrical field deposition technology for thin films, and in laser technology for use in laser materials. In addition, the nanoparticles have a significant grain size. Control of grain size is important in being able to tune the properties of a specific material for a particular application. For example semiconducting materials such as cadmium selenide, have a tunable bandgap energy as a function of size in the nanoscale regime which gives rise to tunable optical properties. Their outer organic layer or coating, uniform size and composition should allow the nanoparticles to cross the blood brain barrier, thus affording materials for formulating into useful compositions, e.g., drugs, small molecules, for medical and pharmaceutical uses. The properties of the nanoparticles prepared by the methods of this invention provide further commercially applicable utility for these materials in a variety of products such as many types of cosmetics, polymers, plastics, paints, and a variety of other industrial products and formulations. Other examples of applications of the nanoparticles prepared by the methods of this invention include skin products, drug delivery vehicles, and MRI contrast enhancement agents.

In another aspect, the present invention provides compositions comprising the monodisperse and stable nanoparticles for use in cosmetics and pharmaceutical compositions. For pharmaceutical compositions, a pharmaceutically or physiologically acceptable carrier, diluent, excipient, or vehicle is further included.

Yet another aspect of the present invention provides efficient and inexpensive methods for synthesizing nanoparticles, in particular, specific transition metal oxide nanoparticles, such as iron oxide, manganese oxide, and zinc oxide, in which the method comprises treating a metal acetate precursor under anhydrous conditions in the presence of organic solvent, e.g., trialkylamine, and at least one organic stabilizing ligand, e.g., oleic acid, and at temperature of from about 100° C.-150° C., and decomposing the metal acetate to produce metal oxide nanoparticles of uniform crystal size.

A further aspect of the present invention provides high quality monodisperse, uniformly-sized nanoparticles, which are stable; resist degradation, e.g., via oxidation or nonpolar solvents; are encased or packaged in an outer organic layer or coating; and which result from the practice of the described methods. The nanoparticles can be magnetic and can comprise thin films. A composition comprising the nanoparticles of the invention can be used for the preparation of magnetic recording media, read and write heads, imaging devices or components thereof (including contrast enhancement agents in MRI imaging and/or other biomedical imaging applications), electrical field deposition devices or components thereof, magnetic devices or components thereof, optical devices or components thereof, or thin films. Such nanoparticles can be employed in a variety of applications, including those described hereinabove.

In a particular aspect, the present invention involves a method of synthesizing iron oxide (FeO) nanoparticles of uniform size and monodispersity comprising subjecting iron acetate starting material to a temperature of from about 200° C. to about 260° C., preferably about 250° C., in an organic solvent, e.g., trialkylamine, in the presence of oleic acid to produce iron oxide nanocrystals having the desired properties following decomposition of the iron acetate and precipitation of the FeO nanocrystals with a flocculent, e.g., a polar organic solvent, into hydrocarbon solvent under conditions of a temperature lower than the reaction temperature used with the iron acetate, e.g., room temperature, or 100° C. or lower.

In another particular aspect, the present invention involves a method of synthesizing monodispersed and uniform manganese oxide, i.e., MnO and $Mn_3O_4$, nanoparticles comprising subjecting manganese acetate starting material to a temperature of from about 300° C. to about 350° C., preferably about 320° C., in an organic solvent, e.g., trialkylamine, in the presence of oleic acid to produce manganese oxide nanocrystals having the desired properties following decomposition of the manganese acetate and precipitation of the MnO nanocrystals with a flocculent, e.g., a polar organic solvent, into hydrocarbon solvent under conditions of a temperature lower than the reaction temperature used with the iron acetate, e.g., room temperature, or 100° C. or lower. The method produces superlattices of MnO (FIG. 2F). $Mn_3O_4$ nanocrystals can be prepared by oxidation of the. MnO nanoparticles, e.g., by natural oxidation of MnO in air; such $Mn_3O_4$ nanocrystals have magnetic properties, e.g., ferromagnetic properties.

In a related particular aspect, the $Mn_3O_4$ nanocrystals synthesized in accordance with this invention provide a magnetic material having magnetic properties and applications. A $Mn_3O_4/Fe_3O_4$ superlattice comprising the $Mn_3O_4$ nanocrystals provides a magnet. A superlattice thin film comprising $Mn_3O_4/Fe_3O_4$ is further provided by the invention. In addition, magnetoresistive material, involving magnetoresistive oxide thin films can be produced using electrical field deposition technology, which is a technique practiced in the art.

Additional aspects, features and advantages afforded by the present invention will be apparent from the detailed description, figures, and exemplification hereinbelow.

DESCRIPTION OF THE FIGURES

FIG. 1A shows X-ray powder diffraction (XRD) patterns of 7 nm diameter MnO nanocrystals exhibiting the highly crystalline peaks that can be matched to the series of Bragg reflections corresponding to the standard and phase pure cubic rock salt structure of MnO. FIG. 1B shows the indexed selected area electron diffraction patterns (SAED) of the MnO nanocrystals formed by the methods of the invention and having the XRD patterns shown in FIG. 1A.

FIG. 2A shows a TEM of MnO nanoparticles of 6-7 nm. (50 nm scale). FIG. 2B shows a TEM of MnO nanoparticles of 14 nm. (70 nm scale). FIG. 2C shows a TEM of MnO nanoparticles of 16 nm. (125 nm scale). FIG. 2D shows a TEM of MnO nanoparticles of 20 nm. (150 nm scale). FIG. 2E shows a TEM of 16 nm MnO nanoparticles having cubic structure. (30 nm scale). FIG. 2F shows that quality superlattice structures are formed from the MnO nanoparticles synthesized according to the present methods and viewed by TEM. (100 nm scale).

FIG. 3A shows a TEM of uniformly sized 6-7 nm $Mn_3O_4$ nanocrystals, which were oxidized naturally in air. (100 nm scale). FIG. 3B shows the XRD analysis of the $Mn_3O_4$ nanoparticles of FIG. 3A, prepared by the present methods. FIG. 3C shows the indexed SAED analysis of the $Mn_3O_4$ nanoparticles analyzed in FIG. 3B.

FIG. 4A shows the results of a Super-conducting Quantum Interference Device (SQUID) analysis of magnitization versus temperature of the MnO nanoparticles. SQUIDs are used to measure the magnetic properties of materials at low temperature. FIGS. 4B-4E (2K, 5K, 20K and 30K, respectively) show hysteresis studies of the MnO nanoparticles at different temperatures. FIG. 4F shows a SQUID analysis of magnitization susceptibility versus temperature of the $Mn_3O_4$ nanoparticles. FIGS. 4G-4L (2K, 5K, 10K, 20K, 40K and 50K, respectively) show hysteresis studies of the 14 nm $Mn_3O_4$ nanoparticles at different temperatures.

FIGS. 5A (100 nm scale) and 5B (80 nm scale) show TEM analyses of ZnO nanorods (2-3 nm×30-40 nm) produced by the present methods. FIGS. 5C and 5D show a SAED analysis of the ZnO nanorods (2-3 nm×30-40 nm) produced by the methods. FIG. 5E shows an Ultraviolet-Visible Spectrum (UV-vis) of the ZnO nanorods produced by the present methods. The UV-vis shows the absorption profile in this part of the electromagnetic spectrum, thus elucidating the nanocrystals' interaction with light.

FIG. 6A shows the average diameter of MnO nanocrystals as a function of growth over time at 100° C. FIG. 6B shows the data of FIG. 6A replotted as the particle diameter cubed versus the growth time, in accordance with the LSW model as described in Example 1.

FIG. 7A shows a TEM of the FeO nanoparticles at 300 nm scale; FIG. 7B shows a TEM of the FeO nanoparticles at 200 nm scale; FIG. 7C shows a TEM of the FeO nanoparticles at 100 nm scale; FIG. 7D shows a TEM of the FeO nanoparticles at 500 nm scale; and FIG. 7E shows an XRD of the 13 nm FeO nanoparticles produced by the present methods.

FIG. 8A shows an XRD of the ZnO nanorods; and FIG. 8B shows a TEM of the ZnO nanorods (100 nm scale).

FIG. 9A shows the results of XRD analyses of 2 nm, 4 nm and 6 nm $Cu_2O$ nanoparticles produced by the methods of the present invention. FIGS. 9B-9E show TEM images of monodisperse $Cu_2O$ nanoparticles at various magnifications, namely at scales of 75 nm, 150 nm, 50 nm and 20 nm, respectively. FIGS. 9F and 9G show TEM images of a $CU_2O$ nanocrystal superlattice (10 nm scale and 15 nm scale, respectively).

DETAILED DESCRIPTION OF THE INVENTION

Figure 1A:
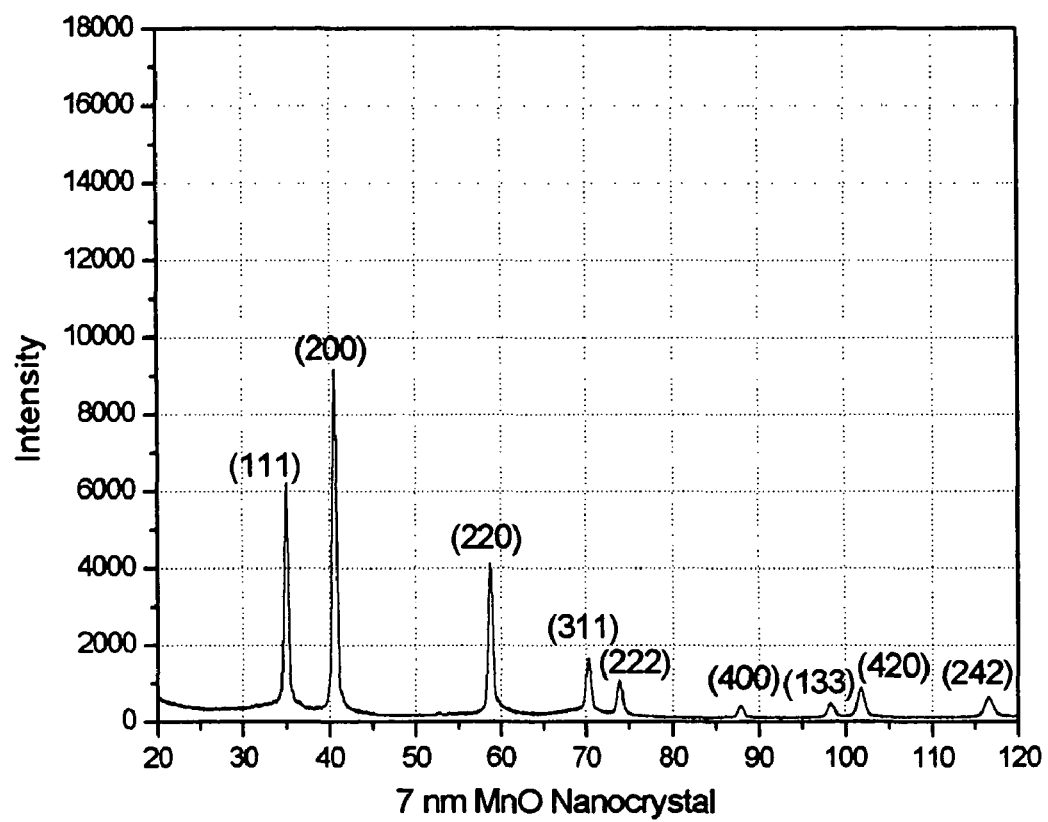
FIGS. 1A and 1B show the crystalline characteristics of MnO nanocrystals prepared according to the present invention.

The present invention relates to methods of preparing nanoparticles (also referred to as nanocrystals herein) having size dependent nanocrystallite properties, including uniform size, monodispersity and stability over time, particularly in air and in nonpolar solvents. Magnetism is a further property possessed by a number of the nanoparticles of the present invention. This invention provides new synthetic routes to a prepare homologous sized series of monodisperse nanocrystals, which are monodisperse in terms of size, shape, internal structure and surface chemistry. In addition, the invention provides nanoparticles formed by the methods for use in a variety of different applications as described herein. As understood by the skilled practitioner, the term "nanocrystal" refers specifically to a crystalline nanoparticle, comprising an inorganic core of a single crystal of nanometer dimensions. The present invention encompasses both crystalline and non-crystalline metal oxide nanoparticles. The methods of the invention are particularly advantageous for producing nanoparticle products that are crystalline.

Optical, electrical and magnetic studies of well-defined nanocrystal samples reveal the unique size-dependent properties of materials in this intermediate, nanometer size regime between molecular species and bulk solid. The present invention encompasses a newly-developed transition metal oxide system to produce nanostructured materials by virtue of a concerted synthetic, spectroscopic, and structural investigation. Methods for the preparation and systematic characterization of high quality nanocrystalline systems are provided. To distinguish true size dependent evolution from simple sample inhomogeneities and defects, a series of homologous samples spanning the size range of interest were produced as is described herein. When samples are nearly monodispersed, the ensemble average of the properties observed is representative of the properties of each individual crystallite. Thus, samples have been systematically synthesized and characterized using a combination of chemical and structural probes. By using generally-known procedures in the art, the structure and properties of these mesoscopic structures have been described with a precision that is comparable to many conventional macromolecules. When the individual nanocrystals and their properties are characterized and controlled, such nanocrystal building blocks are tailored into fundamentally new materials.

One embodiment of this invention embraces a non-aqueous method for the synthesis of metal based nanoparticles, in particular, transition metal oxide nanoparticles. Suitable metal-based nanoparticles include, without limitation, zinc (Zn), iron (Fe), manganese (Mn), cobalt (Co), ruthenium (Ru), copper (Cu), scandium (Sc), titanium (Ti), vanadium (V), chromium (Cr), molybdenum (Mo), yttrium (Y), zirconium (Zr), hafnium (Hf), or nickel (Ni) metal-based nanoparticles, and mixtures thereof. Advantageously, these nanoparticles are capped with organic ligands (e.g., alkyl chain capping groups) and are highly dispersible and stable in non-polar solvents. Illustrative, yet nonlimiting, metal oxides prepared by the present methods include manganese oxide (MnO), iron oxide (FeO) and zinc oxide (ZnO), as well as more highly oxidized forms of one or more of these metal oxide nanoparticles.

In accordance with the invention, the nanoparticles produced by the methods are relatively monodisperse, or uniform in size. Accordingly, the monodisperse nanoparticles of the invention are within less than 10% root mean square deviation (rms) diameter for spherical nanoparticles and less than 10% rms length or width for nanoparticle cubes and rods. The nanoparticles are also of the same shape—either all spheres, or cubes, or rods. The nanoparticles that can be made using the present methods include, but are not limited to nanorods, nanospheres, nanocubes, nanotriangles, nanobipods, nanotripods and nanotetrapods. The size, e.g., diameter, of the nanoparticles produced in accordance with the present invention can range from between about 2 nm and about 50 nm, or from about 3 nm to about 25 nm, or from about 6 nm to about 20 nm. Nanoparticle size can be achieved by controlling reaction parameters and/or conditions, as necessary or desired. For example, and as understood by the skilled practitioner, reaction parameters and/or conditions that may be controlled to achieve nanoparticles of different sizes include temperature, temperature heating and cooling rates, concentration of products, including solvent, ligand and metal precursor, heating and cooling times, and in particular, the time allowed for nanocrystal growth and the ratio of organic ligand to precursor. The nanoparticles generated according to the present methods are stable indefinitely under $N_2$ and are stable in air for periods of several months.

A unique feature and advantage of the present methods is the use of simple metal acetate precursors to prepare ligand-capped transition metal nanoparticles, e.g., MnO, FeO and ZnO, which are safer and more environmentally benign than are nanoparticles prepared from metal carbonyl materials. Other advantages afforded by the synthetic procedures for fabricating metal oxide nanoparticles according to the present invention include the following. First, the method is simple and reproducible, with typical yields of over 80%. Second, highly crystalline and monodisperse nanoparticles are obtained directly from the method without further size selection. A beneficial aspect of the present methods is that monodisperse nanoparticles are generated through its practice without a need for further manipulation, selection, or size-selective precipitations based on size. Such direct production of useful and high quality nanoparticles is another advantage afforded by the present invention. Third, particle size can be easily and fractionally increased by the present methods, thus allowing kinetic studies. Without intending to be bound by theory, the thermodynamics of the methods of the present invention and the reactions therein result in a separation of crystal nucleation from nanocrystal growth. Thus, all nanocrystals start to grow at the same time, spontaneously and homogeneously, resulting directly in substantially monodispersed and stable nanoparticles of uniform size. In one embodiment, the metal acetate precursor is anhydrous.

The methods of the present invention provide the formation of virtually uniform sized nanoparticles having useful properties, such as light reflecting and absorbing properties for use in preventative or therapeutic products and formulations to prevent, reduce, retard, ameliorate, or eliminate photodamage and/or photoaging in a human or animal due to exposure to sunlight, such as in sunscreen formulations or compositions, suntan lotions or formulations and sunblock formulations or compositions. The nanoparticles also can have magnetic properties, which enhance their use in magnetic recording media, and read and write heads, as well as in a number of imaging and optical and electrical methods and devices. As but one example, the nanoparticles find use in the area of electrical field deposition technology for thin films, and in laser technology for laser materials.

In addition, the nanoparticles according to the present invention are uniform in phase (crystal structure) and are coated with a surface passivating layer of organic molecules. The outer organic layer or coating, uniform size and composition allow the nanoparticles to cross the blood brain barrier, thus affording materials for formulating into biomedically-related useful therapeutic and/or preventive compositions, e.g., drugs and small molecules, for medical, dental and pharmaceutical uses. Such compositions can address a need in medicine and related arts to access medically and biologically important areas that are presently difficult to access. In medical or pharmaceutical formulations, the nanoparticles comprise compositions, which typically further include a pharmaceutically or physiologically acceptable carrier, diluent, vehicle, or excipient, such as physiologically sterile saline, or other physiologically acceptable injectable aqueous liquids, and the like.

The above-mentioned properties of the nanoparticles prepared by the methods of this invention, e.g., organic coating and the like, provide further utilities for these materials in many types of commercially useful products such as cosmetics, foodstuffs, such as food powders, polymers, plastics, paints, industrial product formulations, etc. Cosmetics may include, without limitation, makeups, skin and body care products, such as topically-applied skin and body care products, soaps, powders, lotions, creams, ointments, conditioners, shampoos, fragrances, sunscreens, sunblocks, suntanning lotions, deodorants, deodorizers, hair colors and dyes. Topically applied and/or used products and product formulations are advantageously prepared. The optical and biochemical properties of zinc oxide nanoparticles can impart special features to a variety of cosmetic preparations for care of the hair and skin. In powders and creams ZnO nanoparticles can protect the skin by absorbing ultraviolet radiation that can lead to photoaging and skin damage; in burn ointments ZnO nanoparticles can aid healing.

As a particular yet nonlimiting example, zinc oxide nanoparticles find utility in numerous applications in various industries. Some of all of these utilities also apply to others of the metal oxide nanoparticles according to this invention. For example, zinc oxide nanoparticles are useful in the rubber industry, such as in the particular areas of activation, acceleration, biochemical activity, dielectric strength, heat stabilization, latex gelation, light stabilization, pigmentation, reinforcement, rubber-metal bonding and tack retention. In addition, metal oxides, in particular zinc oxide, is useful in aspects of the plastics industry; in adhesives, mastics and sealants; in lubricants, such as in extreme-pressure lubricants, seizure-resistant lubricants, and greases; in photocopying processes, in which the presence of ZnO nanoparticles may result in increased photoconductivity and semiconductor properties by special heat and/or doping treatments (addition of foreign elements). Also, ZnO nanoparticles may be greatly modified in optical properties to increase the absorption of light rays in the visible region, a process known as sensitization, which is generally carried out by addition to certain dyes, which are absorbed on the surface of ZnO nanoparticles. Other useful aspects of metal oxide nanoparticles, such as ZnO nanoparticles of the present invention, include anti-corrosive properties in metal protective coatings, cigarette filters to remove selected ingredients from tobacco smoke; sulfur removal from certain fluids and gases, such as industrial flue gases; foods and food packaging materials, e.g., incorporation into the varnish linings of metal containers to prevent discoloration from food; flame retardants; ferromagnetic materials for electronic, television, radio, and telecommunication applications; batteries, fuel cells, photocells, thermoelements; components in silicate compositions to form waterproof, fireproof refractory materials, as a fungistat in fungicides to increase their effectiveness in certain formulations; and as a component of Portland cement involved in retardation of setting and hardening (to reduce the rate of heat evolution) and in improvement in whiteness and final strength of the cement product.

In one embodiment, the present invention generally embraces a method of preparing monodisperse and stable metal oxide nanoparticles non-hydrolytically. The method comprises mixing a metal acetate precursor with a non-aqueous organic solvent comprising at least one organic stabilizer, or organic stabilizing ligand, to form a reaction mixture; heating the mixture at a temperature of greater than about 100° C., or at a temperature of from about 150° C. to about 450° C., or at a temperature of from about 150° C. to about 400° C., or at a temperature of from about 200° C. to about 380° C., or at a temperature of from about 250° C. to about 360° C., or at a temperature of from about 320° C. to about 350° C., for a time sufficient to allow the formation of metal oxide nanoparticles in organic solution, e.g., about 45 minutes to 1 hour, or about 1 hour. The reaction mixture is heated to the desired elevated temperature over a time period of from about 10 minutes to about 30 minutes, or from about 10 minutes to about 15 minutes, and the reaction is maintained at the elevated temperature for about 1 hour. The nanoparticles are then extracted into a hydrocarbon solvent under a cooler temperature, e.g., about 100° C. or less, typically at room temperature, e.g., from about 25° C. to about 60° C., by precipitation in a polar organic solvent, such as alcohols or ketones, also commonly referred to as flocculating agents or flocculents. In one embodiment, the metal acetate precursor is anhydrous.

In a related aspect of the method, particles of different diameters can be obtained by first subjecting the organic solution to the elevated temperature as described, which results in obtaining a specific nanoparticle diameter, e.g., from about 4 nm to about 10 nm. This is followed by subjecting the organic solution comprising the nanoparticles to a second lower temperature of from about 100° C. to about 150° C., for a period of from about 5 minutes to about 60 minutes. At the second lowered temperature, nanoparticles of larger specific diameters, e.g., from about 10 nm to about 40 nm, are obtained. Accordingly, nanocrystals with increased diameter, e.g., as determined by TEM, can be obtained over time at the lower temperature. In one embodiment, the second lower temperature is about 100° C.

An advantage of the methods of the invention is that the resulting metal oxide nanocrystals are coated with an organic material, e.g., an organic ligand, also referred to as ligand capping. The organic coating consists of organic molecules that act as capping agents for the surface, which is beneficial for their subsequent uses in a variety of applications, such as, for example, pharmaceutical compositions, cosmetics, and the like. Moreover, the transition metal oxide nanocrystals formed by the methods of the present invention are safer and more environmentally benign than their metal carbonyl counterparts.

Without wishing to be bound by theory, in accordance with this invention, the reaction of a transition metal acetate in the organic solvent is believed to proceed via thermal decomposition of the acetate to a metal oxide-oleic acid complex, with the formation of $CO_2$ and acetone by-products, aided by the elevated temperature.

In accordance with the methods of this invention, the metal acetate precursor can include, without limitation, zinc (Zn) acetate, iron (Fe) acetate, manganese (Mn) acetate, cobalt (Co) acetate, ruthenium (Ru), copper (Cu) acetate, scandium (Sc) acetate, titanium (Ti) acetate, vanadium (V) acetate, chromium (Cr) acetate, chromium acetate dimer, molybdenum (Mo) acetate, molybdenum acetate dimer, yttrium (Y) acetate, zirconium (Zr) acetate, hafnium (Hf) acetate, nickel (Ni) acetate, or mixtures thereof. In further accordance with the invention, the metal acetate precursor is mixed with an organic solvent, which comprises at least one organic stabilizing ligand, which can have surfactant properties. In one embodiment, the metal acetate precursor is anhydrous.

In general, the organic solvent used in the present methods is typically unreactive with respect to the formation of the nanoparticles, and has a boiling point of from about 150° C. to about 400° C. Thus, as would be appreciated by the skilled practitioner, any suitable solvent having a boiling point at the elevated temperatures as described herein and good solubility of the metal acetate precursor starting materials can be used. For example, other solvents include mineral oil, paraffin wax and polyethylene glycol. Alkylamine and ether (e.g., phenylether or n-dioctylether) solvents are used; an exemplary solvent for use is a trialkylamine. Trialkylphosphines can also be used. Trialkylamine solvents for use in the present methods have the formula $[CH_3(CH_2)_n]_3N$, where n is an integer ranging from 4 to 12. Typically trioctylamine, having the formula $[CH_3(CH_2)_7]_3N$, is used. In contrast to other methods, trialkylamines function as solvent in the methods of the present invention, rather than serving as both solvent and stabilizing ligand. Moreover, in the present methods, the solvent trialkylamines do not interfere with the reaction chemistry that leads to the formation of monodisperse, uniform nanoparticles. Thus, in general, the solvents per se are not directly involved in the formation of nanocrystals in the present methods.

The organic solvent employed in the methods comprises one or more organic stabilizing agent or organic ligand. The one or more organic stabilizing ligands may also function as stabilizing agents. Suitable organic stabilizing ligands for use in the methods of this invention can be any long chain alkyl with one or more carboxylic acid functional group(s). These ligands typically have the formula $C_xH_y[CO_2H]$, for integers x, y, and z that yield real saturated or unsaturated hydrocarbon chain carboxylic acid molecules, wherein x is an integer ranging from 6 to 30; z is an integer ranging from 1 to 3; and y is an integer ranging from 8 to 59. An example of such a carboxylic acid molecule is oleic acid of formula $C_{17}H_{33}CO_2H$. Organic ligands can include, for example, long chain organic compounds expressed in the form R—X, in which "R" comprises either a straight or branched hydrocarbon or fluorocarbon chain having from 6 to 25 carbon atoms or 8 to 22 carbon atoms; and "X" comprises a moiety ("X") which provides specific chemical attachment to the nanoparticle surface. Illustrative active groups include, without limitation, sulfonate (—$SO_2OH$), sulfinate (—OOH), phosphinate (—POOH), phosphorate (—$OPO(OH)_2$), carboxylate, and thiol. Accordingly the resulting stabilizers include sulfonic acids (R—$SO_2OH$), sulfinic acids (R—OOH), phosphonic acids ($R_2POOH$), phosphoric acids (R—$PO(OH)_2$), carboxylic acids (R—OOH), thiols (R—SH), and mixtures thereof. In one embodiment, the organic stabilizer is a carboxylic acid. In a specific embodiment, the organic stabilizer is oleic acid.

Oleic acid is known in the art as a surfactant stabilizer of colloids and has been used to protect iron nanoparticles. Oleic acid comprises a chain of 18 carbon atoms and is about 20 angstroms in length; it is not aliphatic and contains one double bond. The relatively long chain of oleic acid provides a major steric barrier to counteract the strong magnetic interaction between the particles. Oleic acid is advantageously used because it is inexpensive and easily available from natural sources, such as olive oil. Similar long chain carboxylic acids, such as erucic acid and linoleic acid, (e.g., any long chain organic acid with between 6 and 22 carbon atoms may be used alone or in combination) can also be used, in addition to, or instead of, oleic acid. Thus, oleic acid and oleylamine ligands surround the resulting nanoparticles; these ligands can be replaced, or added to, by other aliphatic acids and primary amines, as necessary or desired.

With regard to the method in the above-described embodiment, a typical reaction involves the mixing of metal acetate and organic solvent containing at least one organic stabilizing agent as described above. The resulting mixture is heated rapidly, for a period of from about 10 minutes to about 30 minutes. In one embodiment, the mixture is heated for a period of from about 10 minutes to about 15 minutes. As a particular example, for a solution of manganese acetate, there is a color change to black during the rapid heating period. Thereafter, the solution is maintained at the elevated temperature for at least about 45 minutes, or about 1 hour, and typically under $N_2$ flow, to yield uniform MnO nanocrystals. The method produces yields up to 80%. The nanocrystals are extracted at a lower temperature, e.g., from about 25° C. to about 60° C., into a hydrocarbon solvent, such as an alkane, including, but not limited to pentane, hexane, heptane, octane and dodecane, in particular, hexane, by precipitation in a polar organic solvent such as alcohols, e.g., methanol, ethanol, propanol, and butanol, or ketones, also referred to as flocculating agents (or flocculents). This is followed by centrifugation and redispersion in a hydrocarbon solvent, such as those mentioned above, e.g., hexane. (See, Example 1). Ethanol is a suitable precipitating agent. The nanocrystals resulting from the method are characterized using transmission electron microscopy (TEM) and X-ray powder diffraction (XRD), e.g., as described in Example 1 and shown in FIGS. 1A and 1B and FIGS. 2A-D for MnO nanocrystal formation.

In another embodiment, the nanoparticles produced by the methods of the invention can be deposited onto a solid surface following precipitation and dispersion. The deposited nanoparticle dispersion is dried; drying is conveniently performed at room temperature. Thus, in accordance with this embodiment, monodisperse particle thin films are provided, such as can be used for the many aspects as described herein, e.g., ultra-high density recording media. Suitable solid surfaces or flat substrates include, without limitation, $SiO_2$, Si, glass or carbon, for the preparation of thin films. This is especially useful for magnetic metal particles, which are surrounded by protective ligands, and which produce magnetic particle thin films. Annealing of the particle dispersion to the thin film can comprise temperatures of from about 500° C. to about 600° C. and produces mirror-like thin films; such films can have controlled coercivities, e.g., of from about 500 Oe to about 6500 Oe.

In another embodiment related to the specific transition metal oxide, manganese oxide (MnO), monodisperse and uniform nanocrystals of 7 nm in length were synthesized by thermal decomposition of manganese acetate in the presence of oleic acid at high temperature. (See Example 1). The method of this embodiment involves mixing manganese acetate precursor, e.g., at room temperature (e.g., 25-60° C.), with an organic solvent including at least one organic stabilizing ligand as described herein, e.g., a sulfonic acid, a sulfuric acid, a phosphonic acid, a phosphoric acid, a carboxylic acid, or a thiol, to form a reaction mixture in a non-aqueous environment. Suitable organic stabilizing ligands are carboxylic acids, such as oleic acid. Exemplary organic solvents include, without limitation, trialkylamines, such as trioctylamine or trimethylamine-N-oxide. The mixture is then heated to a temperature of from about 300° C. to about 350° C., and maintained at the elevated temperature for a time sufficient to allow the formation of monodisperse manganese oxide nanoparticles in organic solution and decomposition of the manganese acetate. In one embodiment, the time sufficient is from about 45 minutes to about 1 hour. In another embodiment, the time sufficient is about 1 hour. In one embodiment, the mixture is heated at about 320° C. In an exemplary aspect, after about 1 hour at the high temperature, the organic solution is cooled to a temperature lower than the reaction temperature, i.e., to about 100° C., which results in a gradual increase in crystal size. The manganese oxide nanoparticles are then extracted into a hydrocarbon solvent, e.g., an alkane such as hexane, by precipitation in alcohol, e.g., ethanol, followed by centrifugation and redispersion. The resulting extracted monodisperse manganese oxide (MnO) nanoparticles have a uniform size, e.g., from about 6 nm to about 20 nm, or from about 12 nm to about 20 nm, or from about 6 nm to about 7 nm, and are monodisperse and stable to oxidation over time. In addition, the resulting manganese oxide nanoparticles are ligand-capped due to the organic solvent components, thus resulting in an organic outside coating. In one embodiment, the manganese acetate precursor is anhydrous.

In a related embodiment, the above-described monodisperse MnO nanoparticles are further oxidized to obtain $Mn_3O_4$ nanoparticles. The oxidation comprises exposing the manganese oxide particles to air or chemical oxidation to obtain further oxidized $Mn_3O_4$ nanoparticles. For chemical oxidation, the manganese oxide particles can be exposed to trimethylamine-N-oxide to obtain ligand-capped $Mn_3O_4$ nanoparticles. (See, e.g., Example 1). The resulting $Mn_3O_4$ nanoparticles are also monodisperse and uniform in size and can comprise a nanocrystal size of from about 3 nm to about 20 nm, e.g., about 7 nm.

$Mn_3O_4$ has applications in its pure form as one of the raw materials in the manufacture of professional grade ferrites, which find use in electronic industries. Manganese oxides are also appealing for use in lithium-ion cells, as manganese is inexpensive and environmentally benign. Other uses for $Mn_3O_4$ produced in accordance with the methods of this invention include electrode materials for rechargeable lithium batteries; corrosion inhibiting pigments for epoxy-polyamide and epoxy-ester-based primers and top coatings; starting material for the manufacture of soft magnetic materials such as manganese zinc ferrite, which is useful for magnetic cores in transformers for power supplies; and in the manufacture of welding rods and fluxes.

Exchange spring magnets, which are composed of a two phased distribution of hard- and soft-magnetic grains, have potential application as permanent magnets. An $Fe_3O_4/Mn_3O_4$ superlattice is a strong candidate for such types of magnets. The hard-magnetic grains provide the high anisotropy and coercive fields, while the soft magnetic grains enhance the magnetic moments. The soft grains are pinned to the hard-magnet grains at the interfaces by the exchange interaction, while the center of the soft-magnet grains can rotate in a reversed magnetic field. Such magnets are characterized by enhanced remnant magnetization and reversible demagnetization curves, since the soft grains will rotate back into alignment with the hard grains when the applied field is removed. A superlattice, which consists of a series of repeatedly stacked layers with a substantially enhanced interface effect, is an ideal system for the interface studies. In accordance with the methods presented herein, the preparation of a $Fe_3O_4/Mn_3O_4$ superlattice, or a superlattice thin film, is encompassed, because the $Fe_3O_4$ and $Mn_3O_4$ components have very different magnetic anisotropies and coupling strengths. In such superlattices or thin films, the $Mn_3O_4$ component may significantly improve the performance of ferromagnetism due to its spring exchange or couple exchange. Also, $Mn_3O_4$ nanoparticles formed according to the methods described herein can be used in magnetoresistive materials, e.g., colossal magnetoresistive materials. For example, magnetoresistive oxide thin films comprising, for example, $Mn_3O_4$ can be made using electrical field deposition technology.

In another embodiment, the present invention encompasses a method for forming monodisperse, uniformly sized, and stable nanoparticles of iron oxide (FeO). The method involves mixing iron acetate precursor, e.g., Fe(II)acetate, with an organic solvent, e.g., at room temperature (e.g., 25-60° C.), to form a reaction mixture, which is non-aqueous. The organic solvent includes at least one organic stabilizing ligand, e.g., sulfonic acid, sulfuric acid, phosphonic acid, phosphoric acid, carboxylic acid, or thiol. Suitable organic stabilizing ligands include carboxylic acids, such as oleic acid. Organic solvents including trialkylamines, e.g., trioctylamine or trimethylamine-N-oxide, are suitable for use in the present methods. The mixture is then heated to a temperature of from about 200° C. to about 260° C., preferably, about 250° C., and maintained at the elevated temperature for a timer period of from about 45 minutes to about 1 hour, i.e., a time sufficient to allow the formation of monodisperse iron oxide nanoparticles in organic solution and decomposition of the iron acetate. The iron oxide nanoparticles are then extracted into a hydrocarbon solvent, e.g., an alkane such as hexane, by precipitation in non-polar solvent, such a alcohol, e.g., ethanol, centrifugation and redispersion. The resulting extracted monodisperse iron oxide (MnO) nanoparticles have a uniform size, e.g., about 3 to about 20 nm, or from about 12 to about 20 nm, or 7 nm, and are stable to oxidation over time. The resulting iron oxide nanoparticles are further ligand-capped, thus resulting in an organic outside coating, which provides the aforementioned advantages for a use in pharmaceutical, medically-related, or cosmetic compositions, as well as one or more of the above-described industrial applications, as but a few illustrative examples. In one embodiment, the iron acetate precursor is anhydrous.

In an embodiment related to another transition metal oxide, the present invention embraces a method for forming monodisperse, uniform and stable nanoparticles of zinc oxide (ZnO). The method of this embodiment involves mixing zinc acetate precursor, e.g., at room temperature (e.g., 25-60° C.), with an organic solvent, e.g., a trialkylamine, including at least one organic stabilizing ligand, e.g., a sulfonic acid, a sulfuric acid, a phosphonic acid, a phosphoric acid, a carboxylic acid, or a thiol, to form a reaction mixture in a non-aqueous organic solution. Suitable organic stabilizing ligands include carboxylic acids, such as, for example, oleic acid. Other suitable organic solvents include trialkylamines, such as trioctylamine or trimethylamine-N-oxide. The mixture is then heated to a temperature of from about 320° C. to about 400° C., preferably, about 360° C., and maintained at the elevated temperature for a time period of from about 45 minutes to about an hour, i.e., a time sufficient to allow the formation of monodisperse zinc oxide nanoparticles in organic solution and decomposition of the zinc acetate. The zinc oxide nanoparticles are then extracted into a hydrocarbon solvent, e.g., an alkane such as hexane, at a temperature lower than that of the heating temperature, e.g., 100° C., by precipitation in a polar organic solvent such as an alcohol, e.g., ethanol, or flocculating agent (or flocculent), followed by centrifugation and redispersion. The resulting extracted monodisperse zinc oxide (ZnO) nanoparticles have a uniform size, and are stable to oxidation over time. The resulting zinc oxide nanoparticles are further ligand-capped due to the organic solvent components, thus resulting in an organic outside coating. In one embodiment, the zinc acetate precursor is anhydrous.

In a related embodiment, the above method is employed for the formation of zinc oxide nanorods, which are uniform in size, e.g., 2-3 nm×30-40 nm, and can be used in a variety of applications as described below. In accordance with the above-described method using anhydrous zinc acetate starting material, both spherical nanoparticles and nanorods (i.e., rods with diameters of 2-10 nm and aspect ratios in the range of 1:5 and up to 1:40) can be prepared. Without being bound by theory, this is due to the asymmetric crystal structure of zinc oxide. For the generation of spheric nanoparticles, the zinc acetate:surfactant ratio is 1:3 or greater; for the generation of nanorod nanoparticles, the zinc acetate:surfactant ratio is less than 1:2. The preparation of rods or spheres of zinc oxide depends on the reaction conditions, including choice of ligand and/or organic solvents, such as trioctylamine for rods and 1-hexadecanol or 1-octadecene for spheres.

An application for ZnO nanoparticles prepared according to the methods of the present invention include serving as a material for the emission of ultra-violet light, i.e., as a substitute for GaN, a well-known UV laser material. ZnO may also be used for optoelectronic applications in the short wavelength range (green, blue, UV). In fact, the high exciton binding energy in ZnO (about 60 meV vs. 25 meV for GaN) would allow for excitonic transitions even at room temperature, which could mean a higher radiative recombination efficiency for spontaneous emission, as well as a lower threshold voltage for laser emission. ZnO has several fundamental advantages over the use of GaN: (1) the free exciton of ZnO is bound with 60 meV, much higher than that of GaN (21-25 meV); (2) ZnO has a native substrate; (3) wet chemical processing of ZnO is possible; and (4) ZnO is more resistant to radiation damage, for example, compared with Si or GaAs, which are poor performers for radiation damage. ZnO epitaxy layers can also serve as very suitable materials for photonic devices in the ultraviolet region. The use of semiconductor quantum well structure as a low-threshold optical gain medium represents a sizable advancement in semiconductor laser technology. There is a need in the art to find materials and ways to deposit high-quality c-axis oriented thin films at modest substrate temperatures; ZnO nanoparticles produced according to the present methods can address this need. In particular, electrical field deposition technology can be used to produce thin films comprising ZnO nanoparticles, including ZnO nanorods, according to the present invention.

In another embodiment, the present invention encompasses compositions comprising the above-described metal oxide nanocrystals for use in cosmetic formulations and compositions. Such cosmetic formulations and compositions include, without limitation, makeups, skin and body care products, such as topically-applied skin and body care products, powders, lotions, creams, ointments, conditioners, shampoos, fragrances, sunblocks, sunscreens, suntanning lotions, deodorants, deodorizers, and hair colors and dyes. Topically-applied products and product formulations are advantageous. Nonlimiting examples of skin care formulations that may contain the nanoparticles of the invention are found, for example, in U.S. Pat. No. 6,168,798 to O'Halloran, and U.S. Pat. No. 5,885,596 to P. Parab.

In another embodiment, the present invention encompasses pharmaceutical and medical formulations and compositions comprising the above-described metal oxide nanocrystals. The outer organic coating, which is comprised of organic molecules that act as capping agents for the surface of the nanoparticles of the invention, endow the nanoparticles with the beneficial and clinically relevant property of crossing the blood/brain barrier. Such pharmaceutical and medical formulations and compositions typically include a physiologically or pharmaceutically acceptable carrier, diluent, excipient, or vehicle, typically comprising a suitable liquid or solution such as sterile physiological saline or other physiologically acceptable injectable aqueous liquids.

For injectable administration, compositions comprising the nanoparticles can be prepared in sterile solution or suspension, or resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients, diluents, vehicles, or carriers suitable for use include water, phosphate buffered saline (pH 7.4), 0.15M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

EXAMPLES

The examples described below are provided to illustrate the present invention and are not included for the purpose of limiting the invention.

Example 1

An example of the synthesis procedure to produce metal oxide nanocrystals according to the present invention is provided. In this Example, the formation of MnO nanoparticles is described. To carry out this reaction, 4 mmol of dry manganese acetate ($Mn(CO_2CH_3)_2$, Aldrich) was added to a mixture containing 15 ml of trioctylamine and 3 g of oleic acid (12 mmol) at room temperature. The resulting mixture was heated rapidly to 320° C. over 10 to 15 minutes; during this time, the solution gradually changed to black. The solution was maintained at 320° C. for 1 hour under $N_2$ flow to yield uniform MnO nanocrystals with yields of up to 80%. The nanocrystals were cooled to room temperature, 25-60° C., and extracted into hexane by precipitation with ethanol in an amount between 5-200% volume of the original volume in the reaction vessel. As understood by the skilled practitioner, the extraction temperature was, in general, a temperature cooler than the reaction/heating temperature. In some instances, a temperature of less than 200° C. was used, for example, 100° C. Next, the extracted, precipitated material was centrifuged for 5-100 minutes at about 3000-6000 rpm and redispersed into hexane solvent.

The resulting nanocrystals were characterized using transmission electron microscopy (TEM), (JEOL, 100cx, acc. 100 kV) and X-ray powder diffraction (XRD, Scintag $X_2$). TEM samples were prepared by placing a drop of a dilute hexane dispersion of nanocrystals on the surface of a 400 mesh copper grid backer with Formvar and were dried in a vacuum chamber at 80° C. for 1 hour. XRD samples were prepared by drying a dispersion of nanocrystals on a piece of Si (100) wafer. The XRD spectrum (FIG. 1A) exhibited the highly crystalline peaks that could be matched to the series of Bragg reflections corresponding to the standard and phase pure cubic rock salt structure of MnO (Fm3m, a=4.442 angstroms). The particle size, calculated from the Debye-Scherrer equation, was 6.8 nm, confirmed by average 7 nm diameters in the TEM. Nanocrystal assembly from hexane solutions into closed packed arrays was also observed, thus demonstrating the uniformity of the particle size and retention of the oleic acid capping group.

Figure 1B:
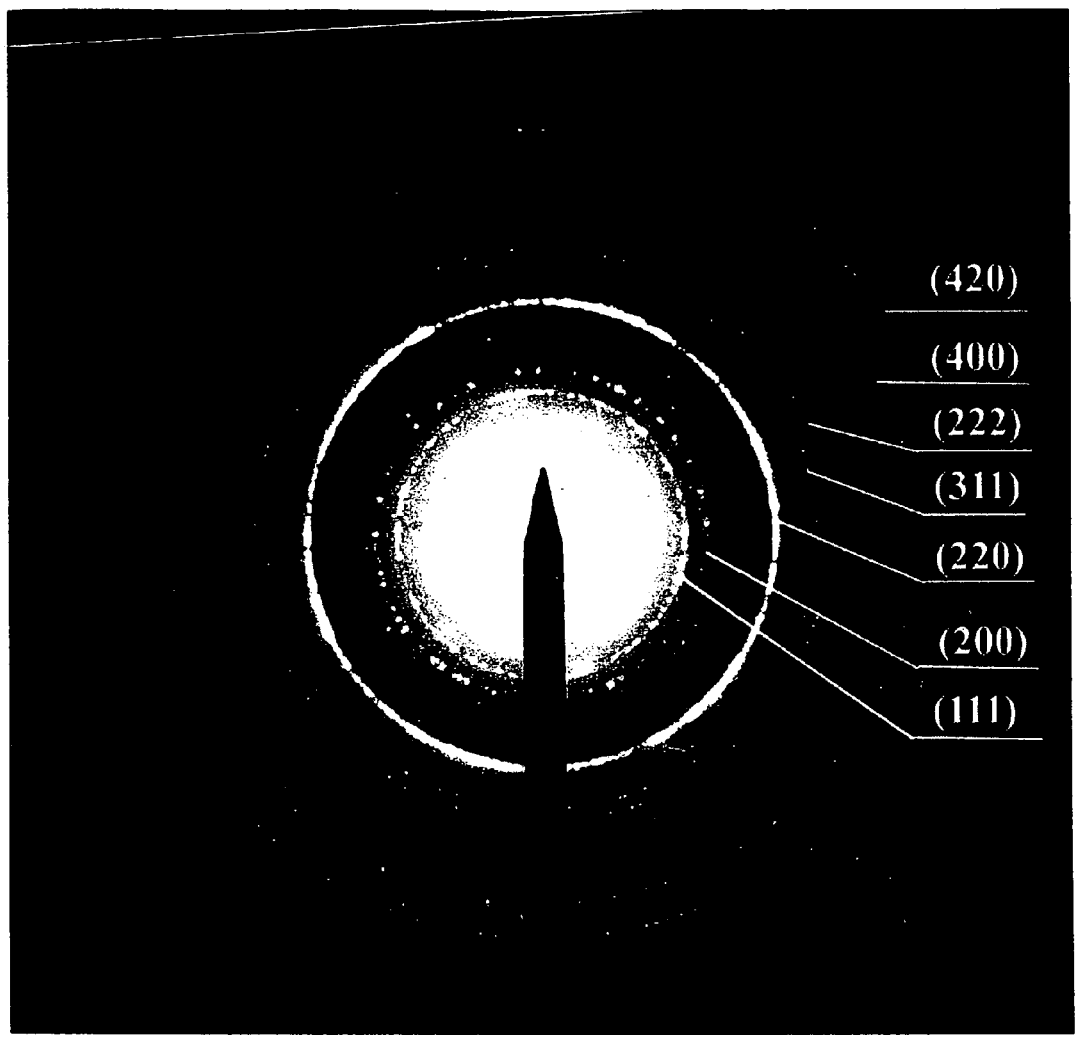
Figure 2A:
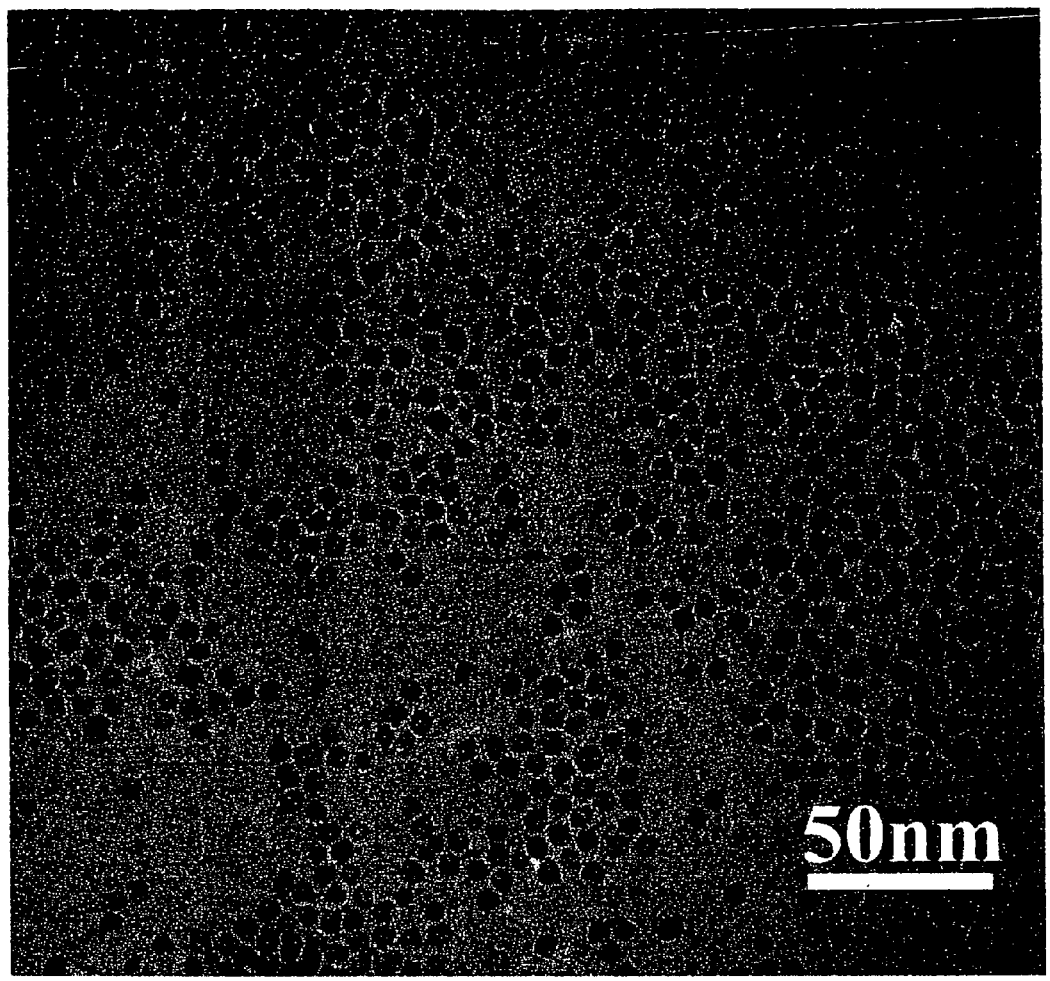
FIGS. 2A-2F show transmission electron micrographs (TEM) of monodispersed nanoparticles of MnO prepared as described according to the present methods.
Figure 2B:
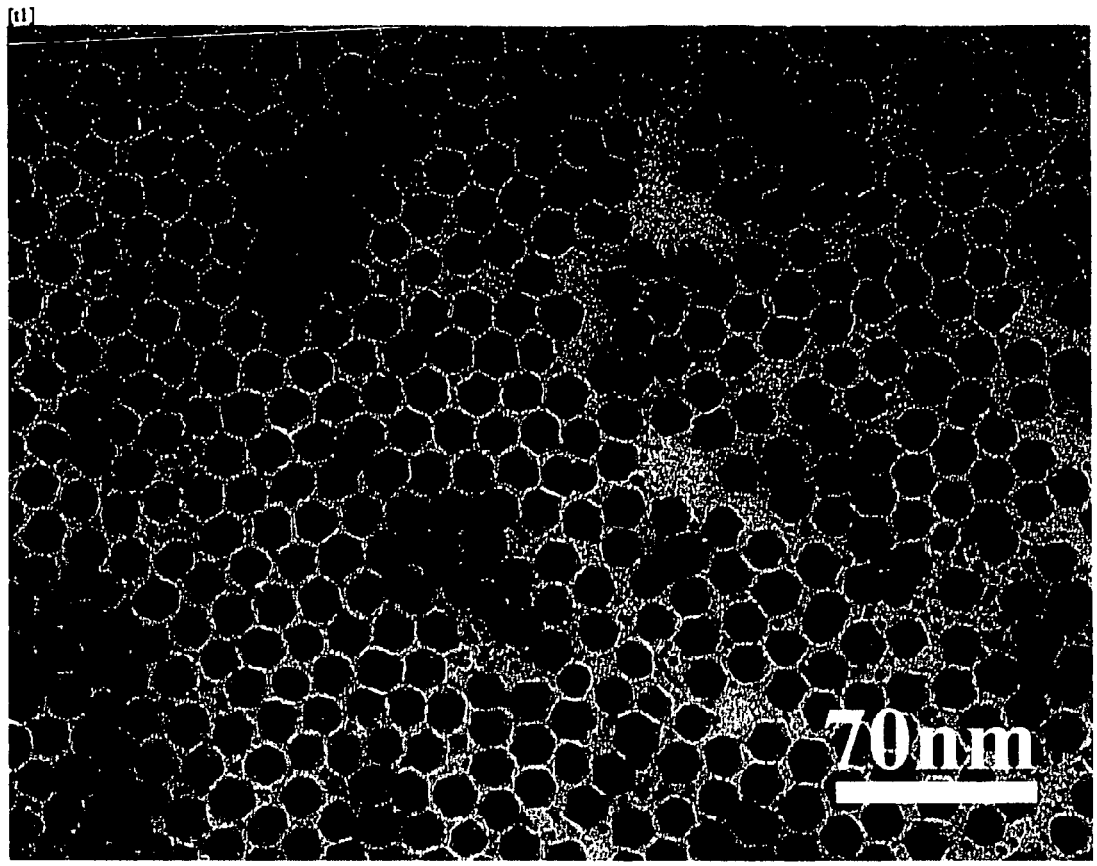
Figure 2C:
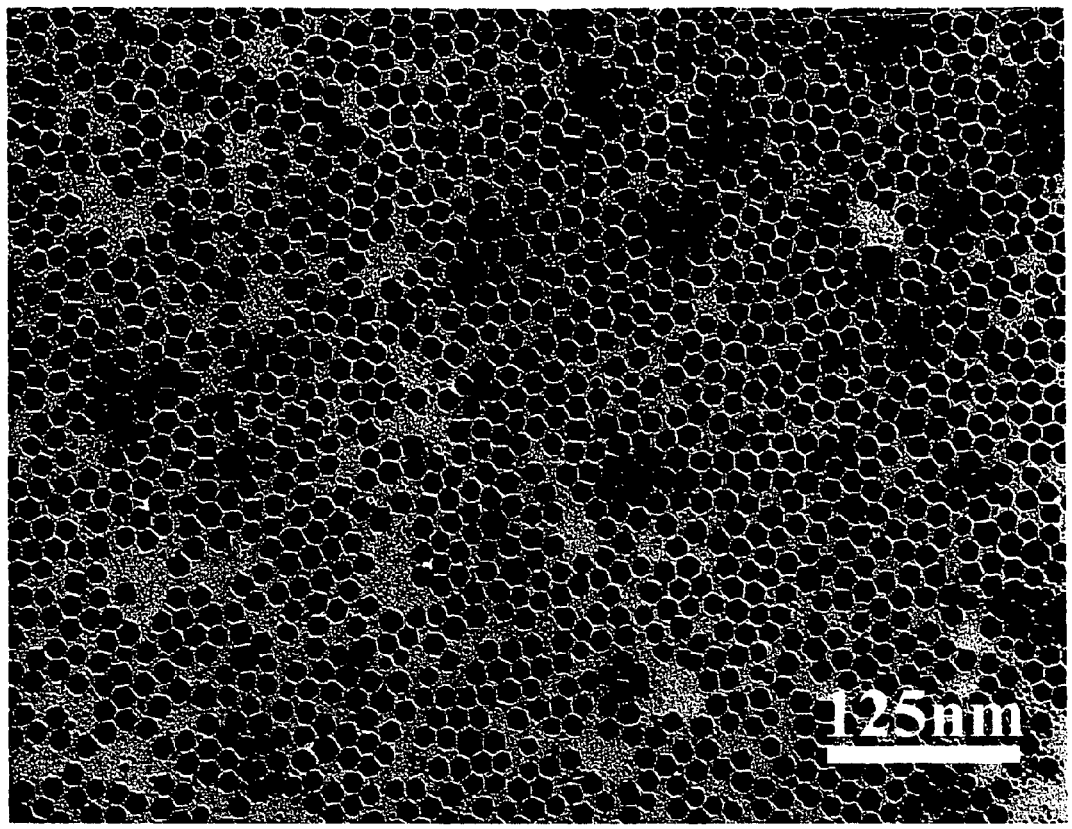
Figure 2D:
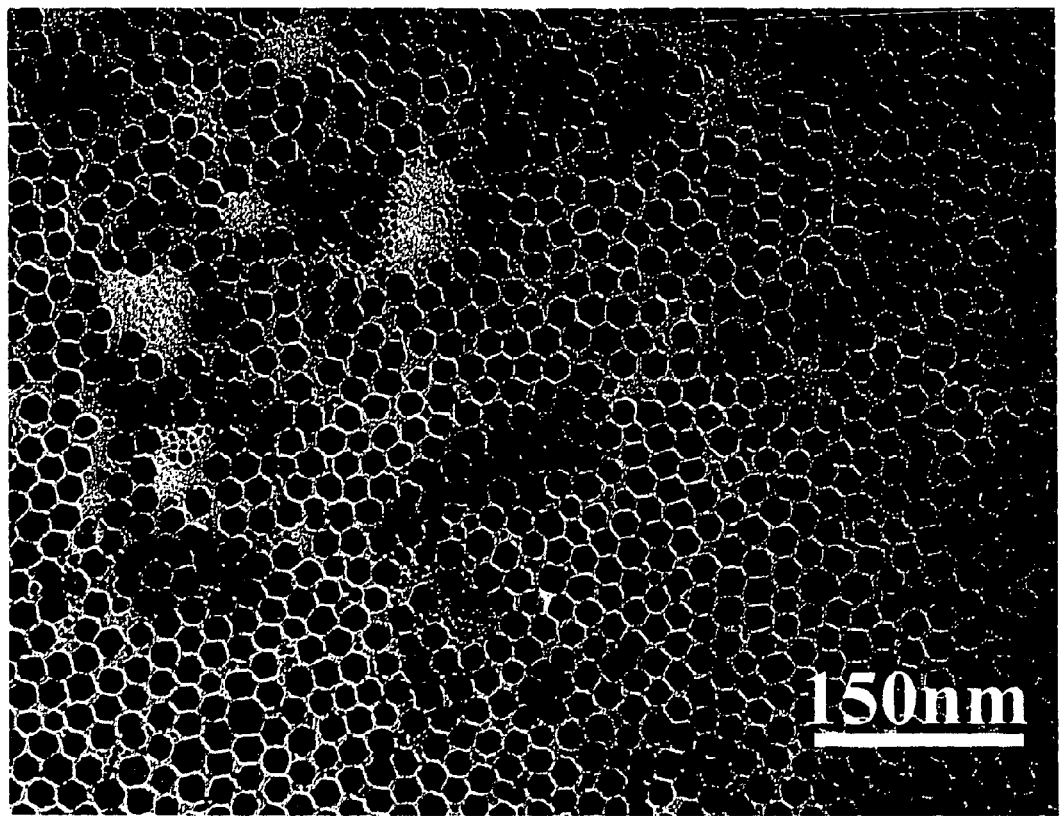
Figure 2E:
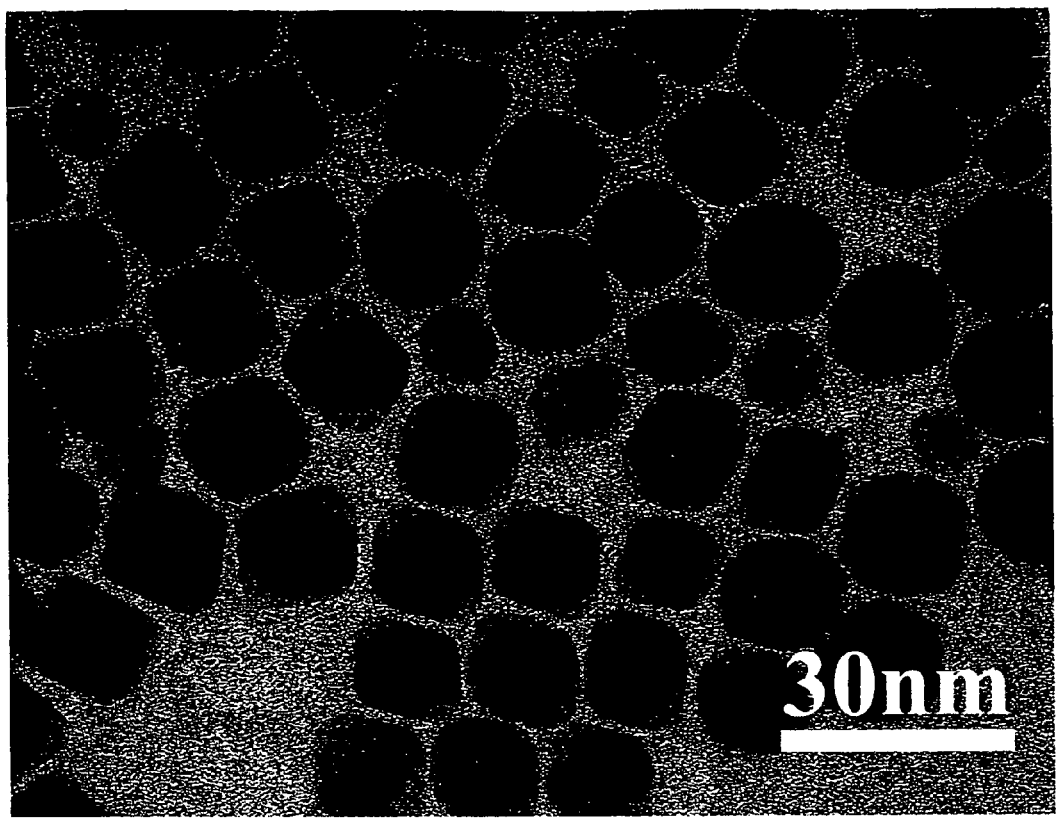
Figure 2F:
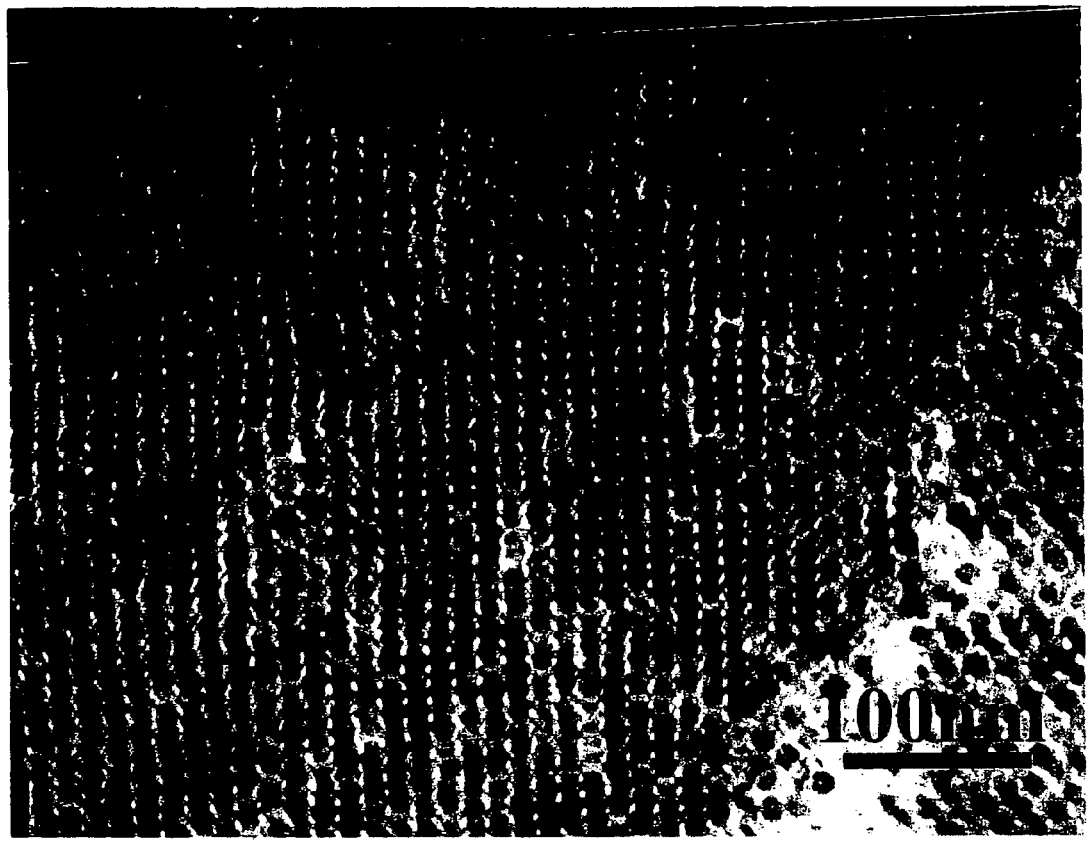
Figure 6A:
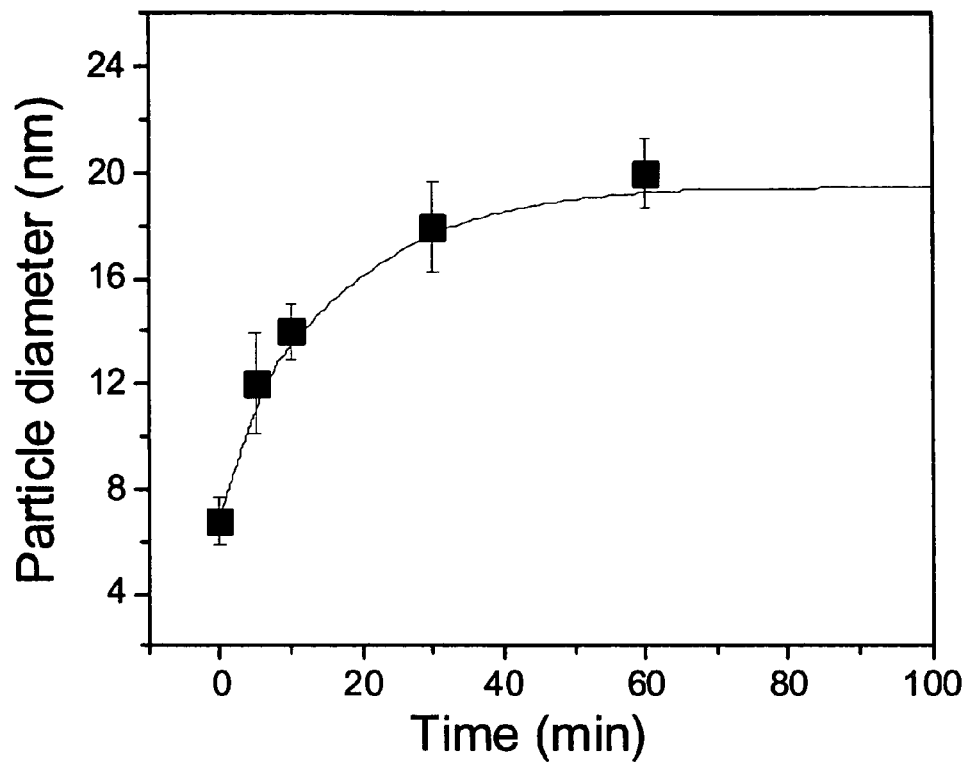
FIGS. 6A and 6B relate to evaluations of particle size of MnO nanocrystals prepared according to the methods of the present invention.

Controlling evaporation conditions, e.g., by using a closed system at room temperature and allowing for diffusion to remove the solvent over periods of from 1-10 hours, allowed for the formation of a three-dimensional close-packed superlattice assembly of 14 nm MnO nanocrystals (FIG. 2B). Selected area electron diffraction patterns (SAED) of all samples indicated a highly crystalline rock salt structure, in good agreement with XRD (FIG. 1B). Monodisperse MnO nanoparticles of from about 12-20 nm in size were prepared as described above, and an annealing step was further performed after the temperature was kept at 320° C. for 1 hour by carefully cooling the resulting solution to 100° C. (FIGS. 2A-2D). Nanocrystals with increasing diameter gradually grew at the lower temperature. Selected area electron diffraction patterns confirmed the MnO structure. Particle size was determined and cross-referenced by XRD Debye-Scherrer analysis and TEM. An increase in cubic faceting of the nanocrystals was observed with an increase in size. (FIG. 2E). The average increase in size of the MnO nanocrystals was followed using TEM with time to prepare samples with average diameters of 12, 14, 18 and 20 nm after 5, 10, 30 and 60 minutes, respectively. (FIG. 6A).

A quantitative assessment of the growth kinetics of transition metal oxide nanocrystals was performed using the Lifshitz-Slyozov-Wagner (LSW) model. (G. Oskam et al., 2003, *J. Phys. Chem. B*, 107:1734; I. M. Lifshitz et al., 1961, *J.*

Figure 6B:
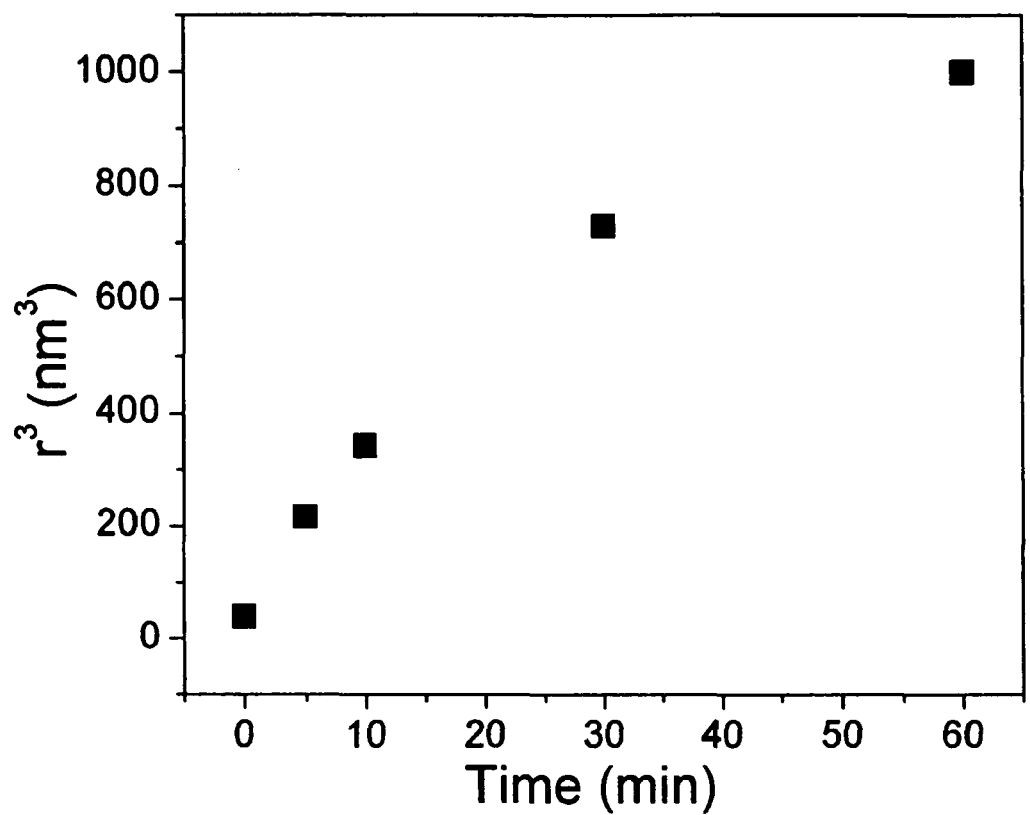
Figure 7A:
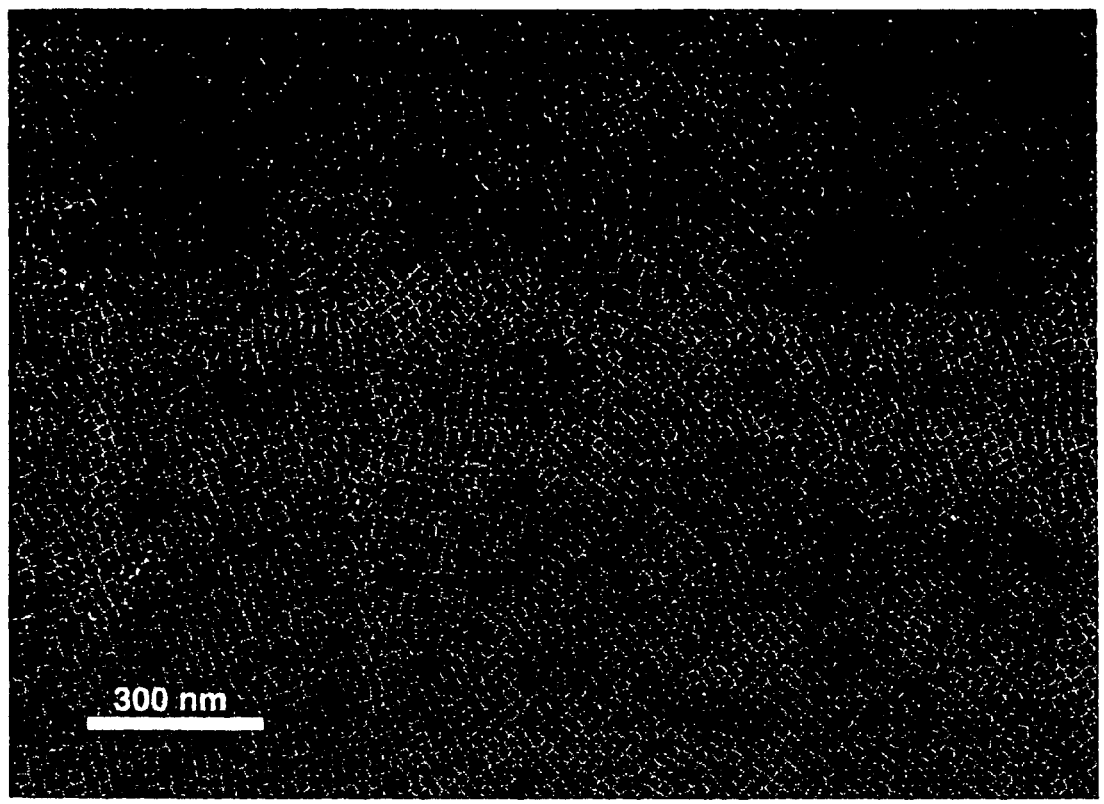
FIGS. 7A-7E relate to the characteristics of FeOm (13 nm) nanoparticles produced according to the methods of this invention. More particularly.
Figure 7B:
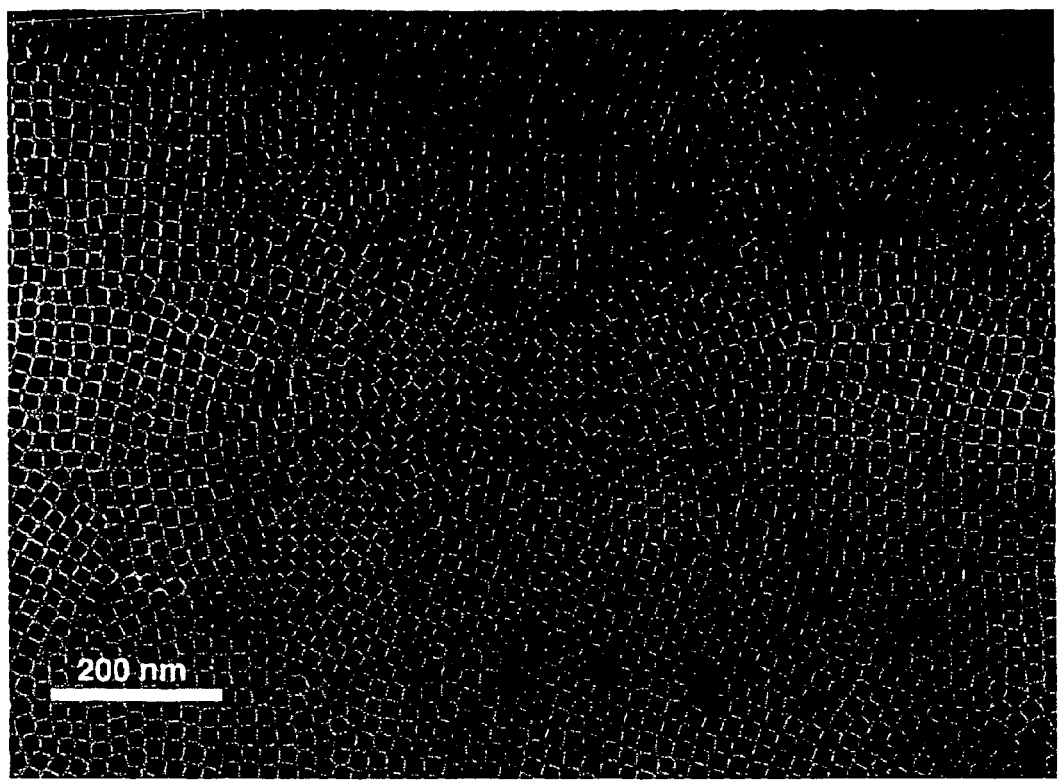
Figure 7C:
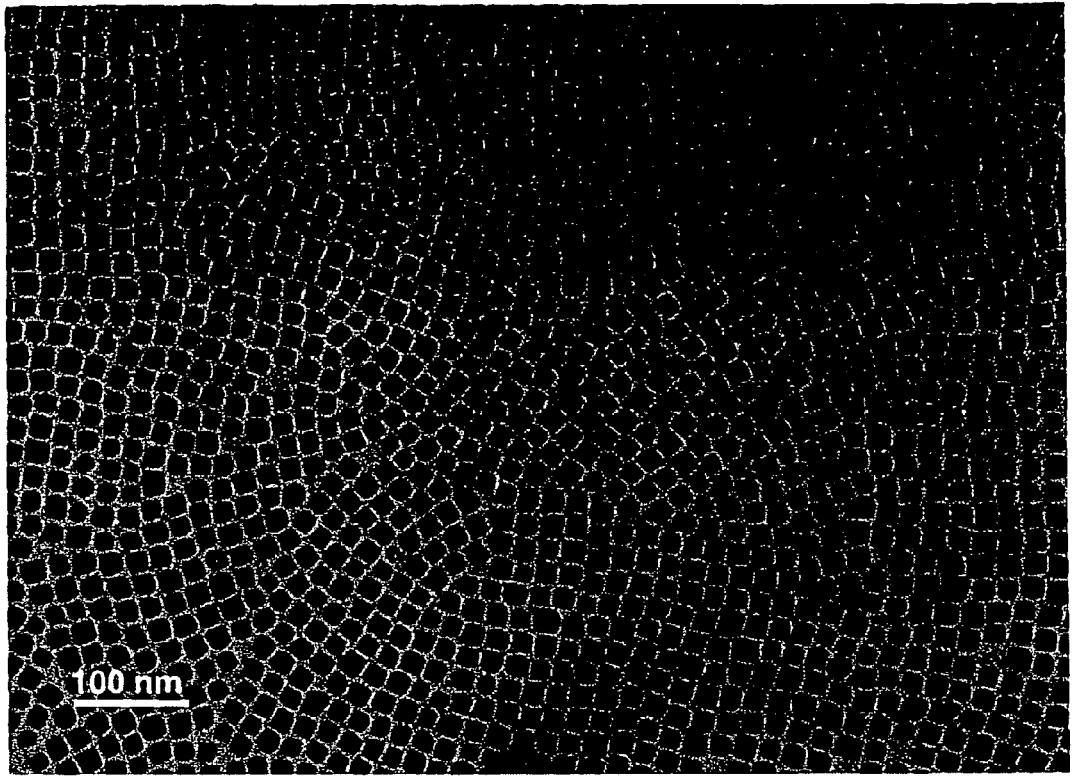
Figure 7D:
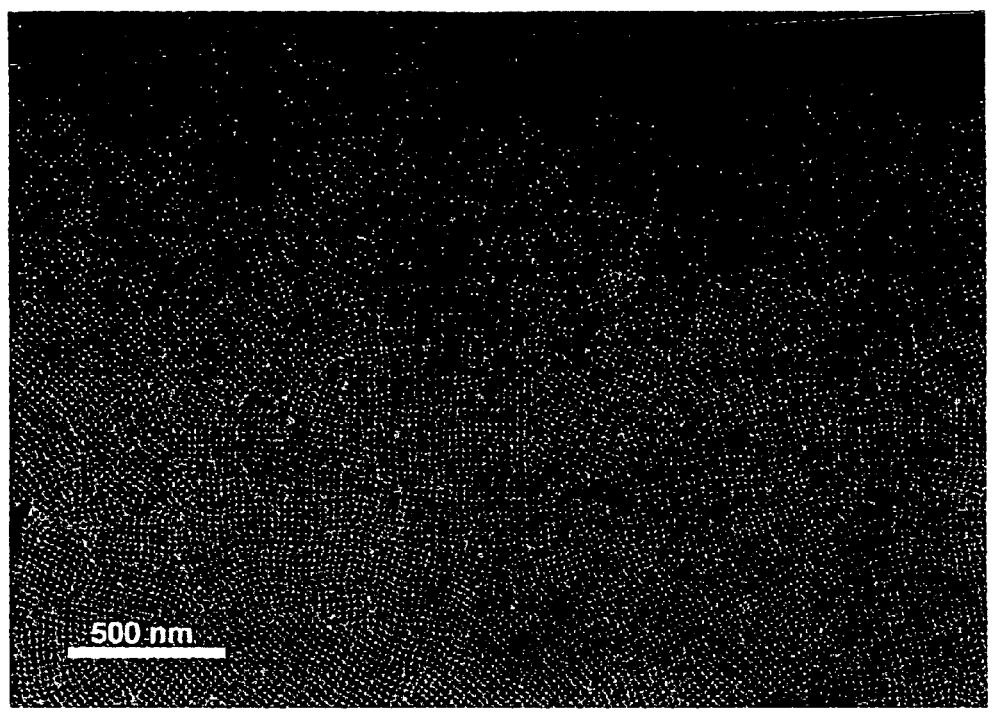
Figure 7E:
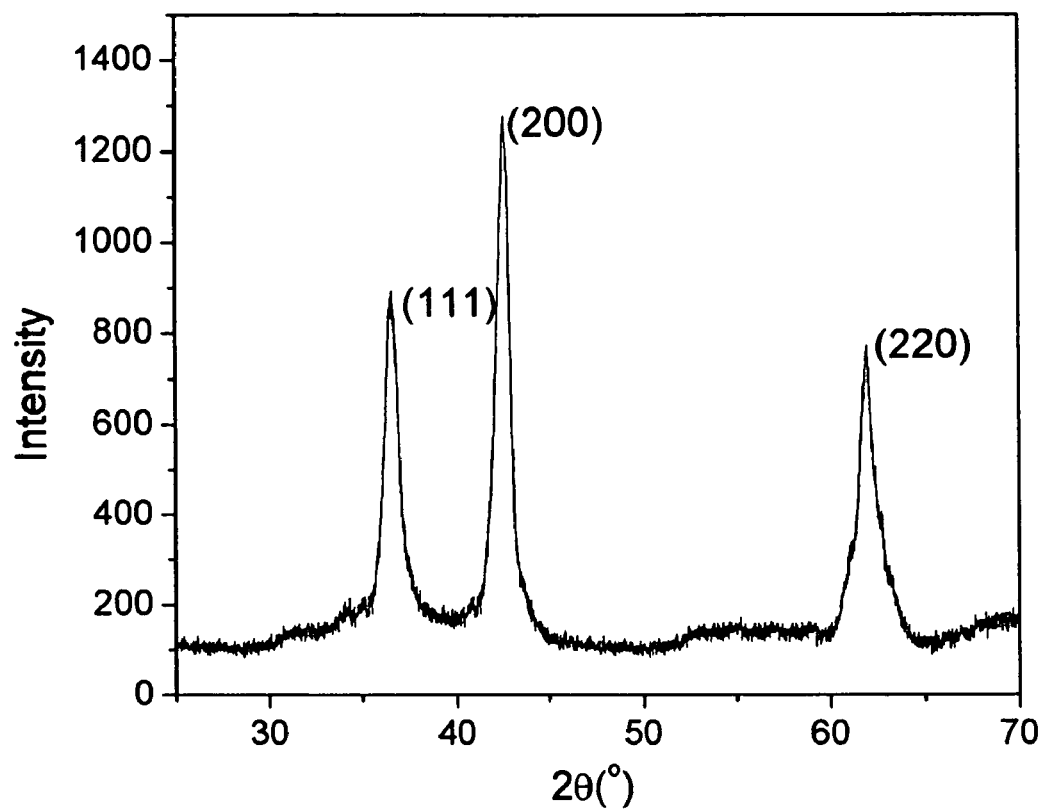
Figure 8A:
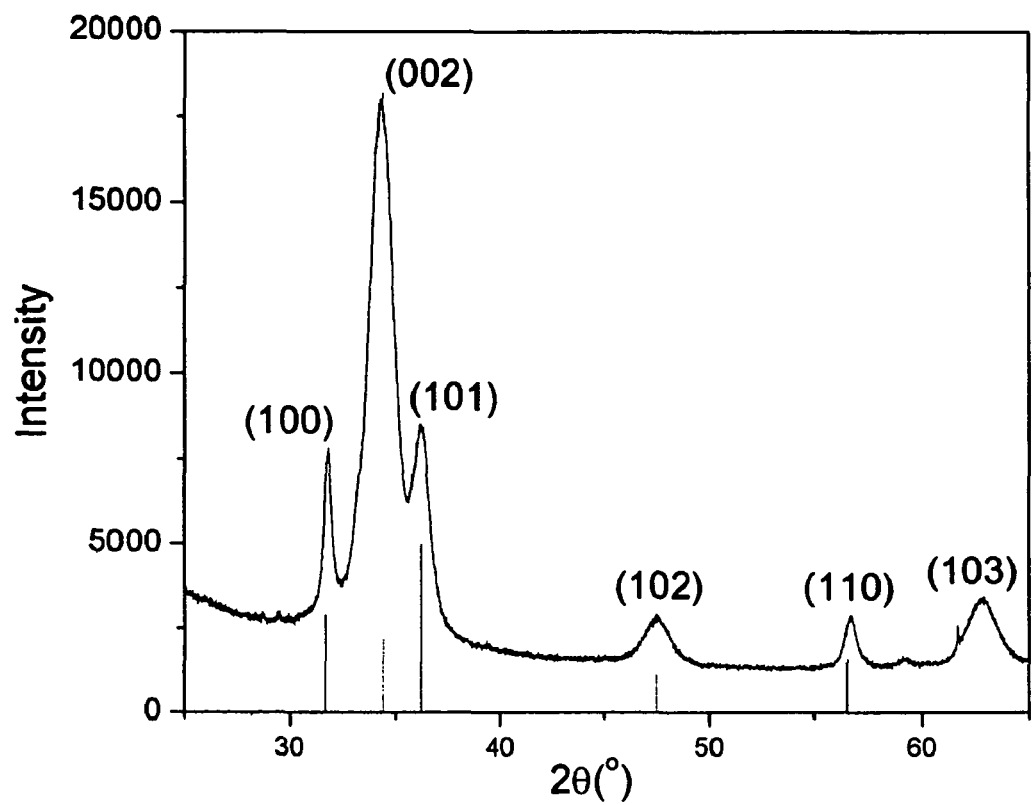
FIGS. 8A and 8B further relate to zinc oxide (ZnO) nanoparticles in the form of nanorods produced according to the methods of the present invention.
Figure 8B:
Figure 9A:
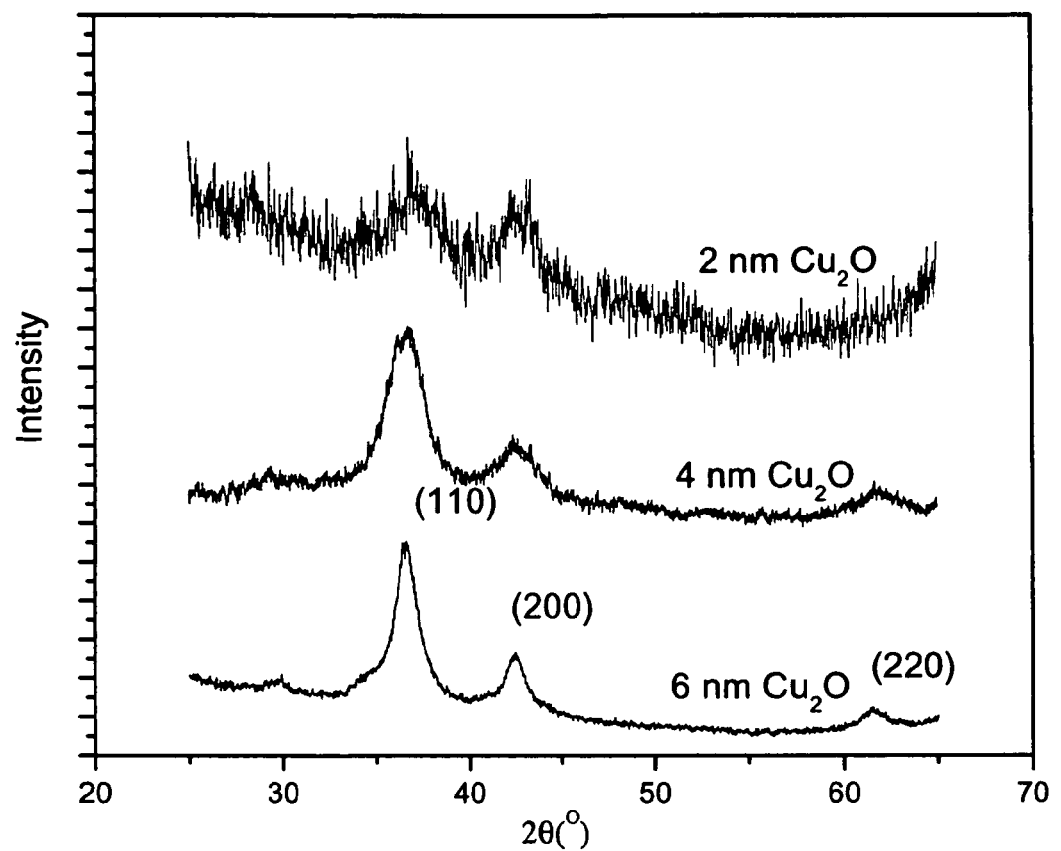
FIGS. 9A-9G relate to copper oxide ($Cu_2O$) nanoparticles produced according to the methods of the present invention.
Figure 9B:
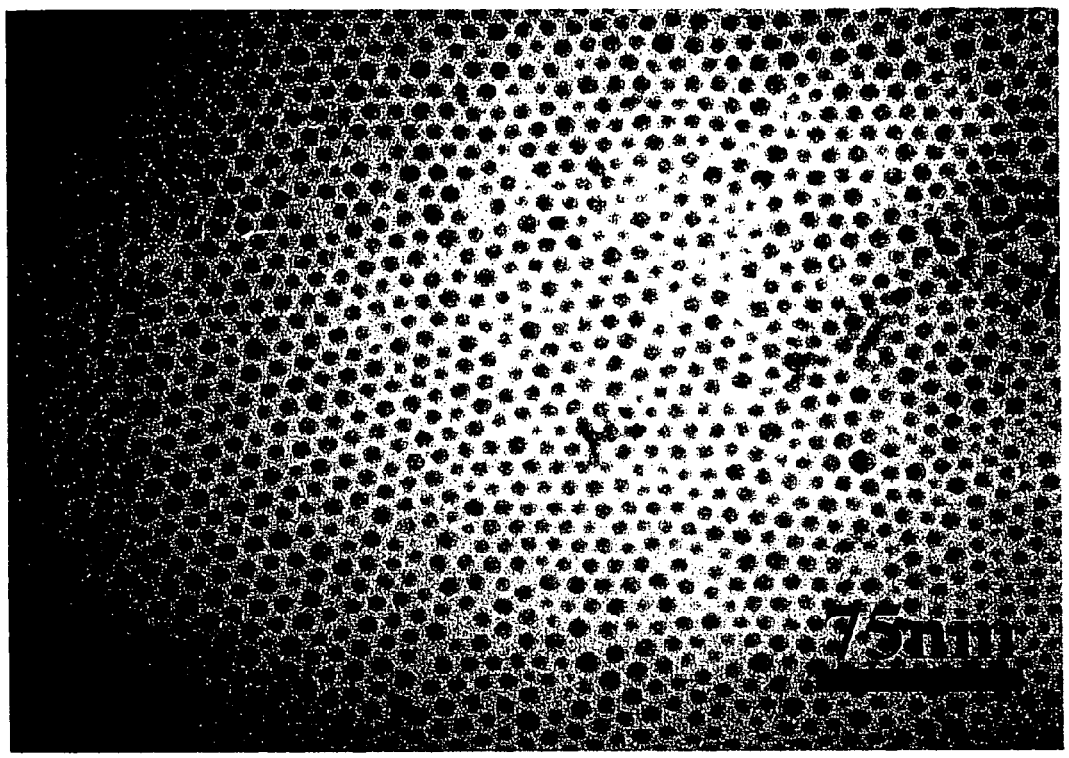
Figure 9C:
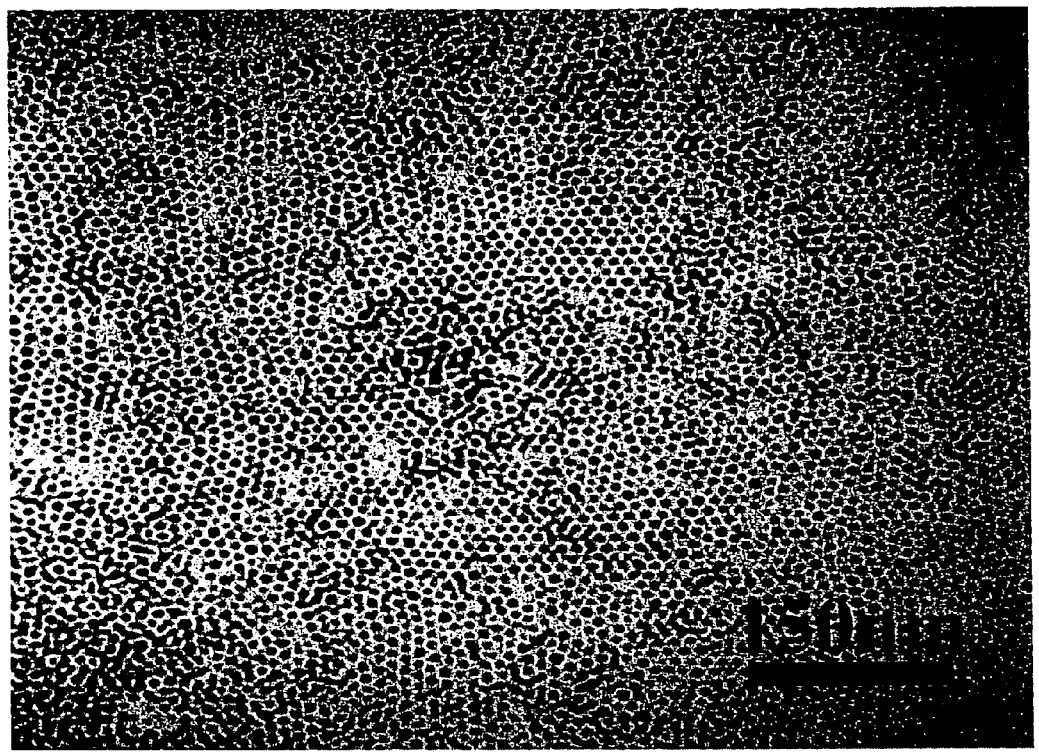
Figure 9D:
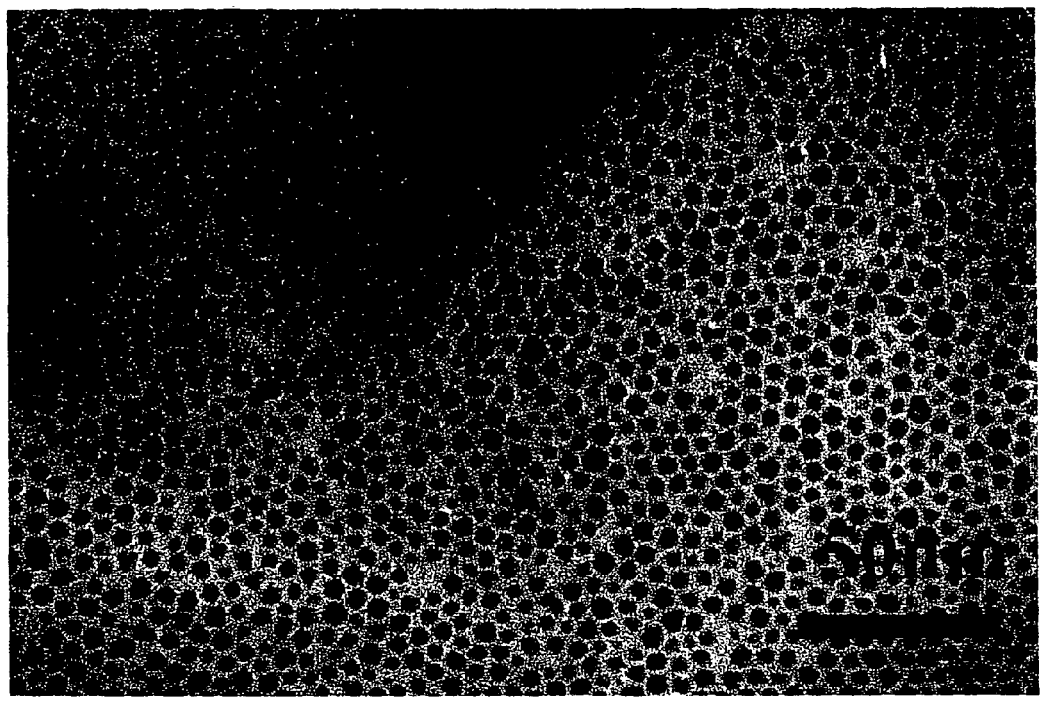
Figure 9E:
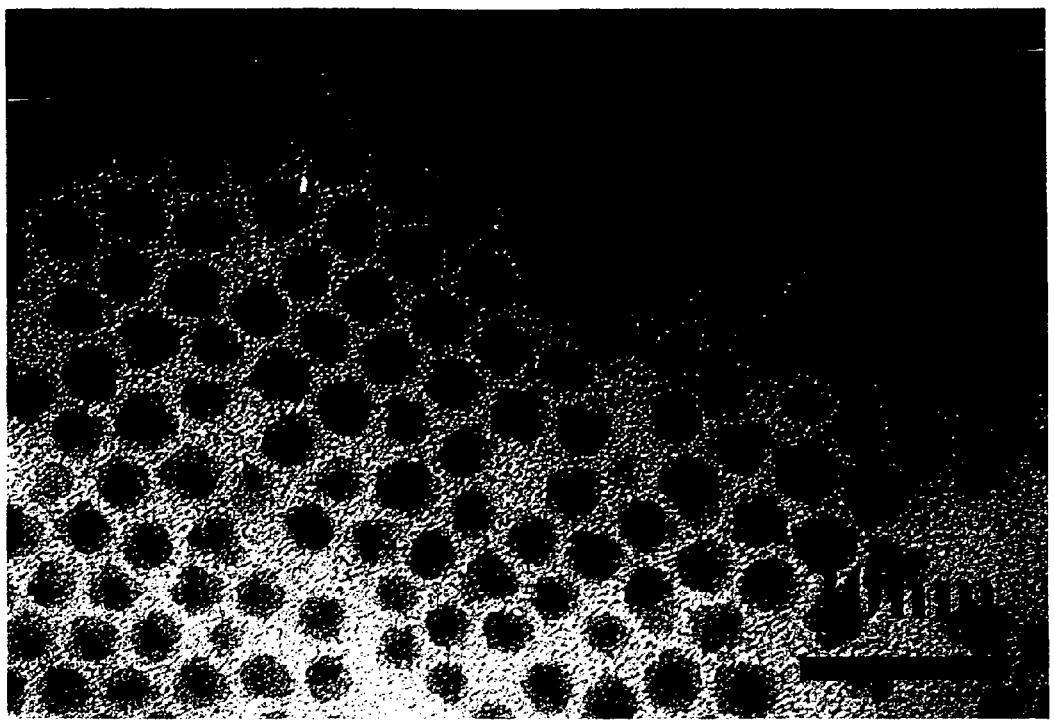
Figure 9F:
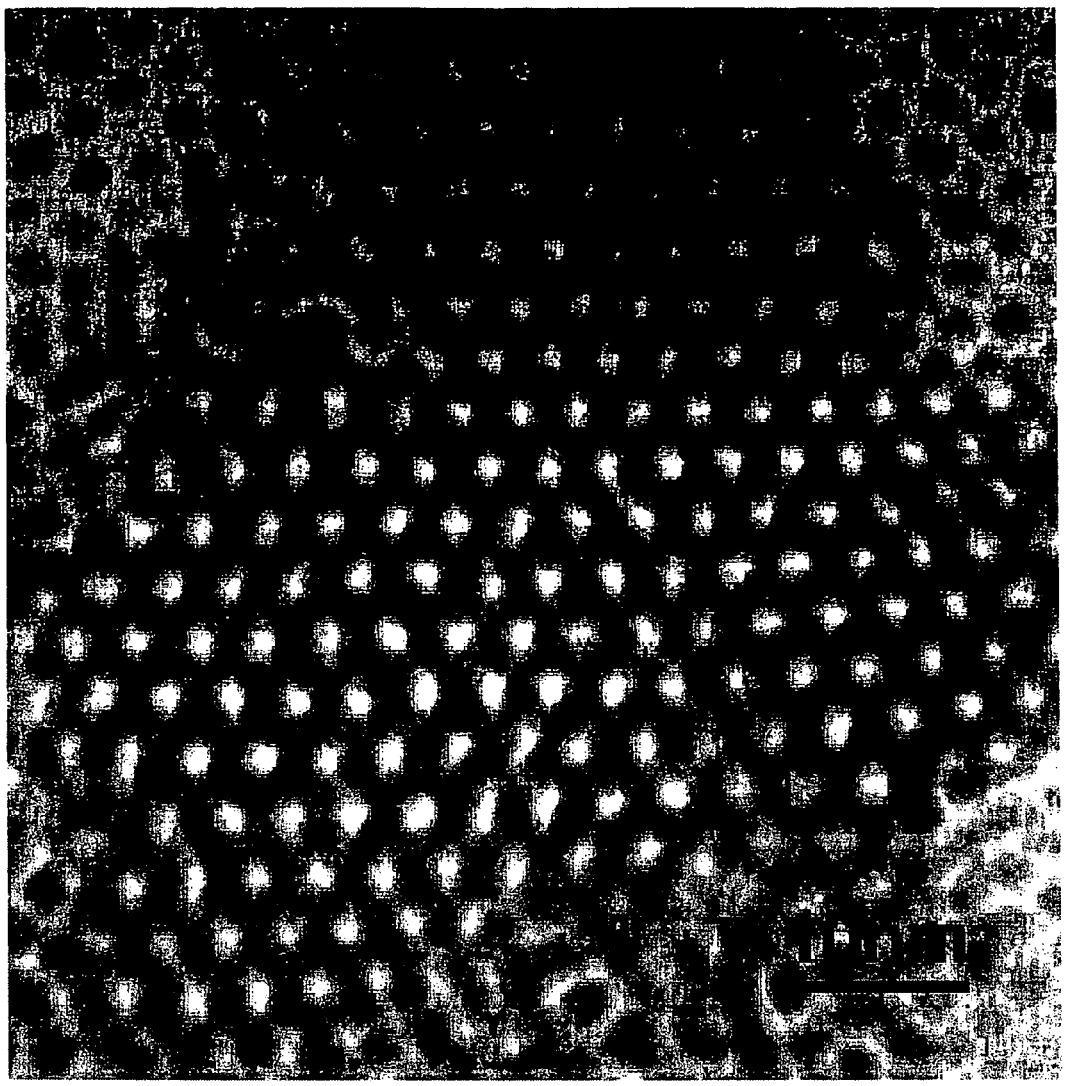
Figure 9G:
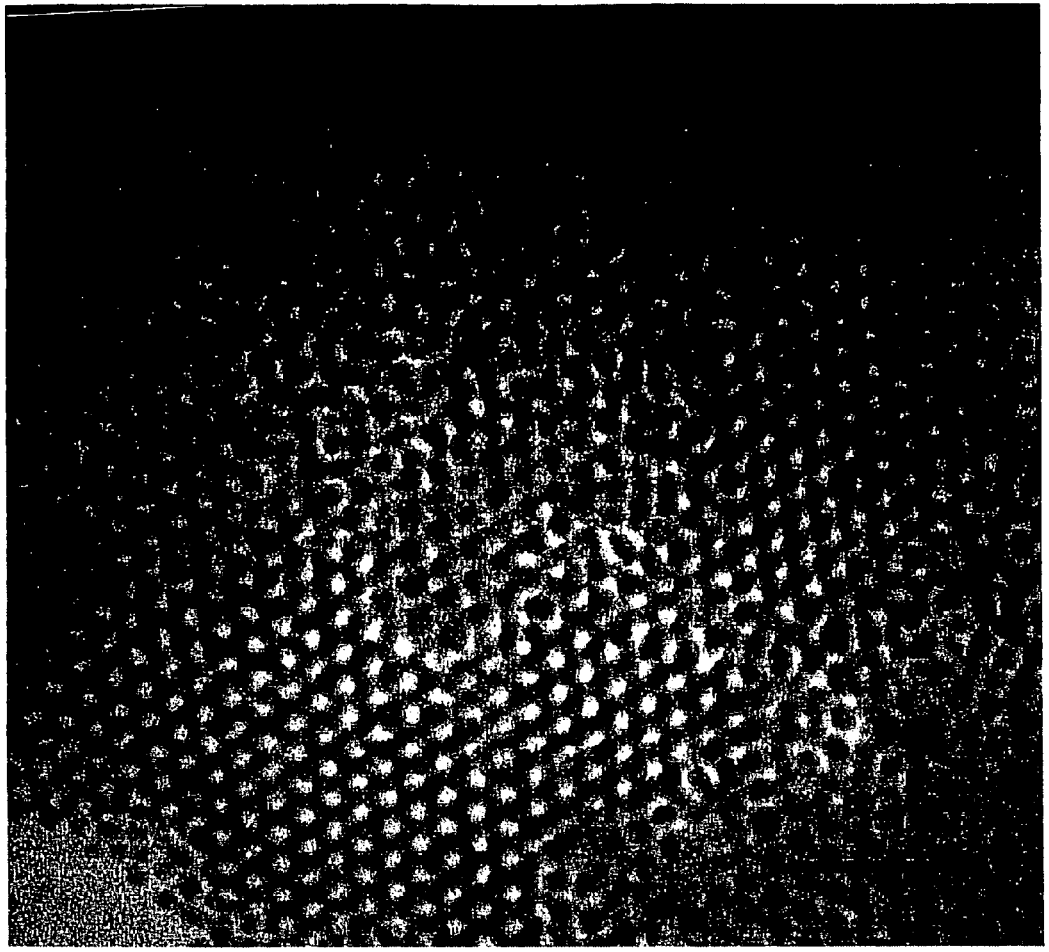

*Phys. Chem. Solids*, 19:35; C. Z. Wagner, 1961, *Elektrochem.*, 65:581). Particle growth is driven by the dependence of the solubility of a solid phase on the particle size according to the Gibbs-Thomson equation. (X. Peng et al., 1998, *J. Am. Chem. Soc.*, 120:5343). Assuming that the particles are spherical, the solubility, $c_r$, of a particle with radius r is given by the following equation:

$$c_r = c_\infty \exp\frac{(2\gamma V_m\ 1)}{(RT\ r)} \quad (1)$$

where $c_\infty$ is the solubility at a flat surface, $\gamma$ is the surface energy of the solid, $V_m$ is the molar volume, R is the gas constant, and T is the temperature. For the case where $(2\gamma V_m/rRT)<1$ such that the exponential term in equation 1 can be linearized, and assuming that the growth rate is determined by diffusion of the solute from the smaller particles to the larger particles, the following rate law is obtained (G. Oskam et al., 2003, *J. Phys. Chem. B*, 107:1734; I. M. Lifshitz et al., 1961, *J. Phys. Chem. Solids*, 19:35; C. Z. Wagner, 1961, *Elektrochem.*, 65:581):

$$r_3 - r_0^3 = \frac{8\gamma D V_m^2 c_\infty}{9RT} t \quad (2)$$

where r is the particle radius at time t and $r_0$ is the particle radius at time zero. (X. Peng et al., 1998, *J. Am. Chem. Soc.*, 120:5343). FIG. 6B shows the cube of the particle radius plotted versus time. It can be inferred from the roughly linear dependence that the increase in particle size is dominated by diffusion-limited growth at this temperature. The intercept at t=0 corresponds to the particle size (7 nm) of the as-prepared sample.

Figure 3A:
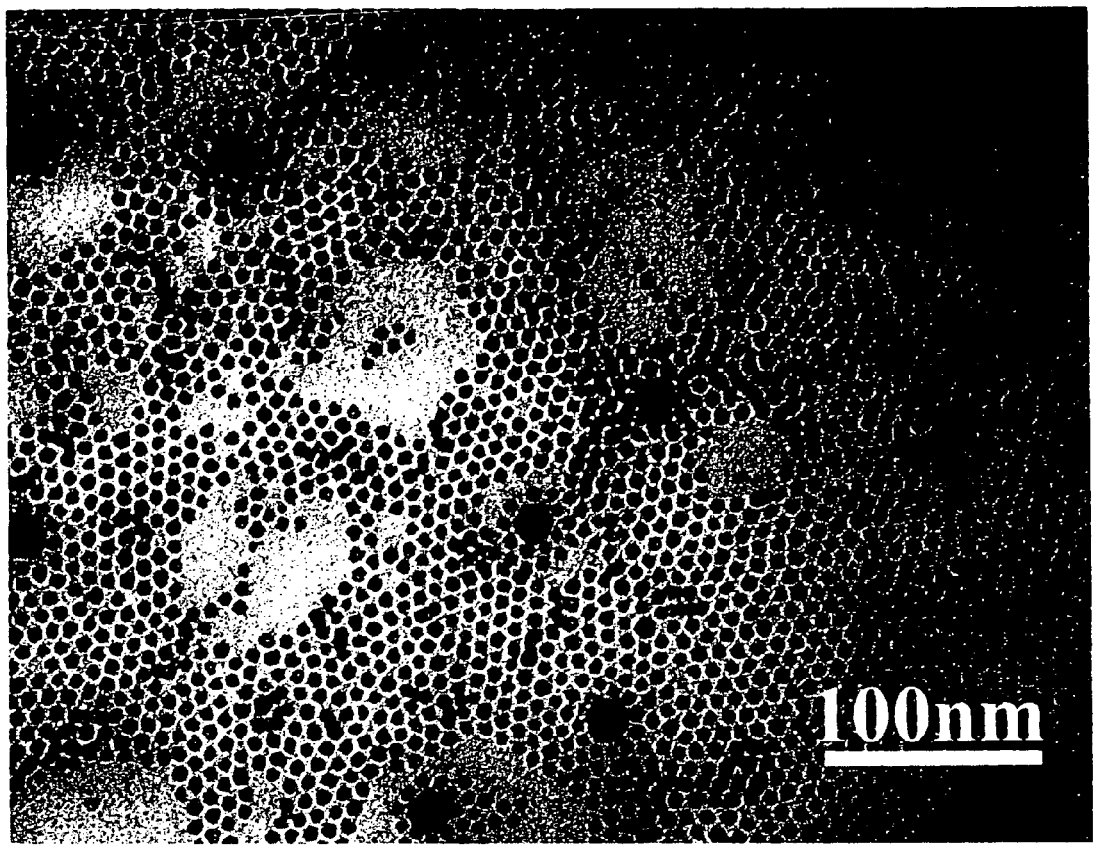
FIGS. 3A-3C show properties of $Mn_3O_4$ nanocrystals prepared according to the present methods by further oxidation of MnO.
Figure 3B:
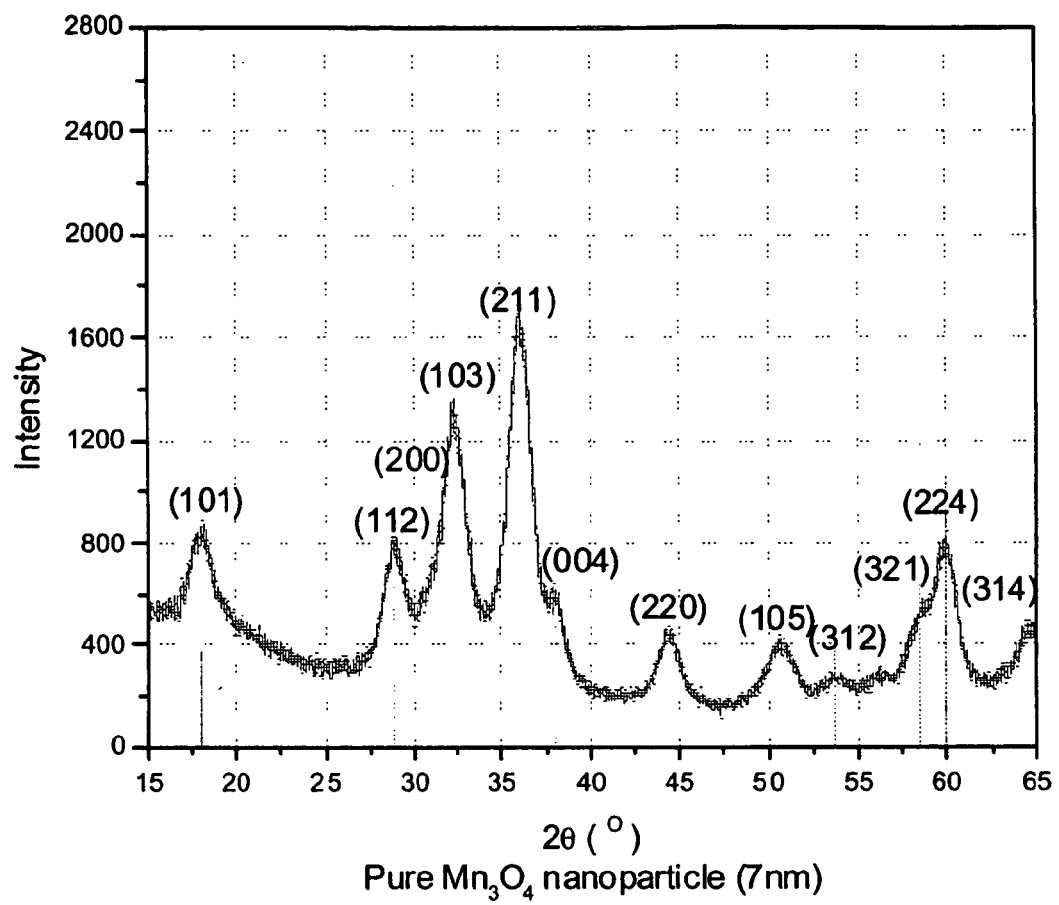
Figure 3C:
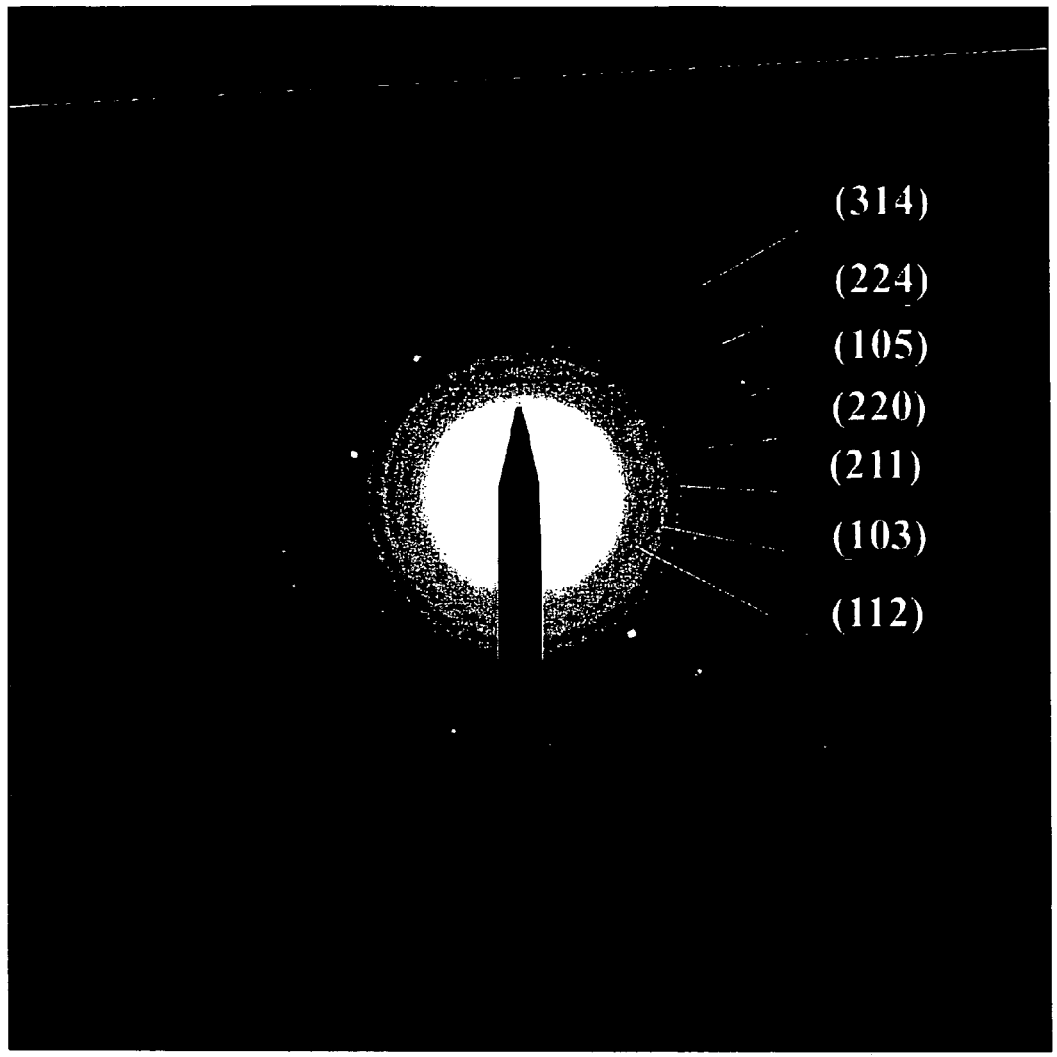
Figure 4A:
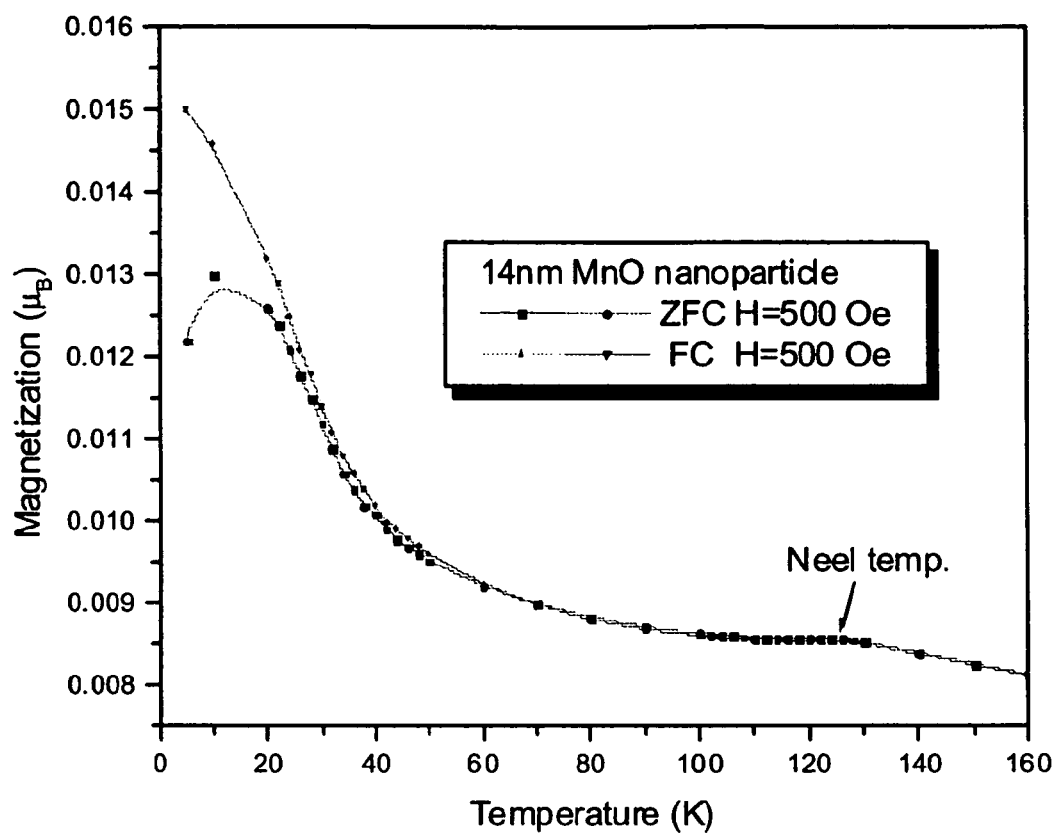
FIGS. 4A-4E depict the results of magnetic studies performed on MnO nanoparticles produced by the methods of the present invention. More specifically these figures depict analyses of the magnetic properties of the 14 nm MnO nanoparticles.
Figure 4B:
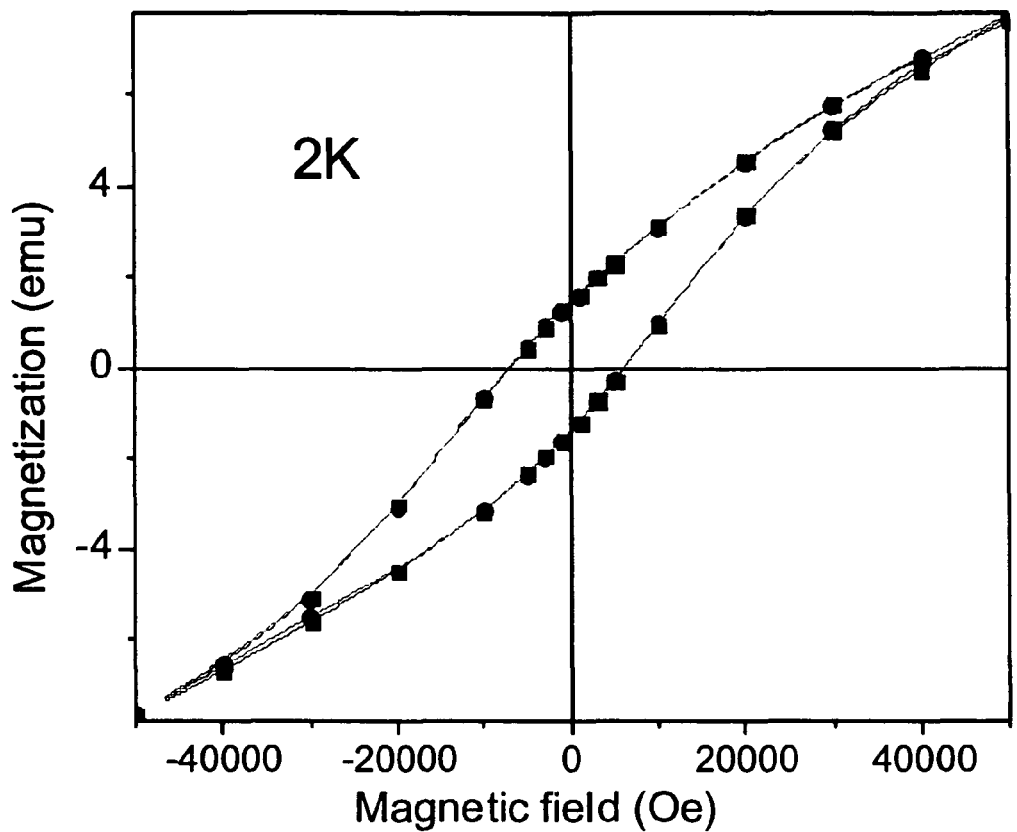
Figure 4C:
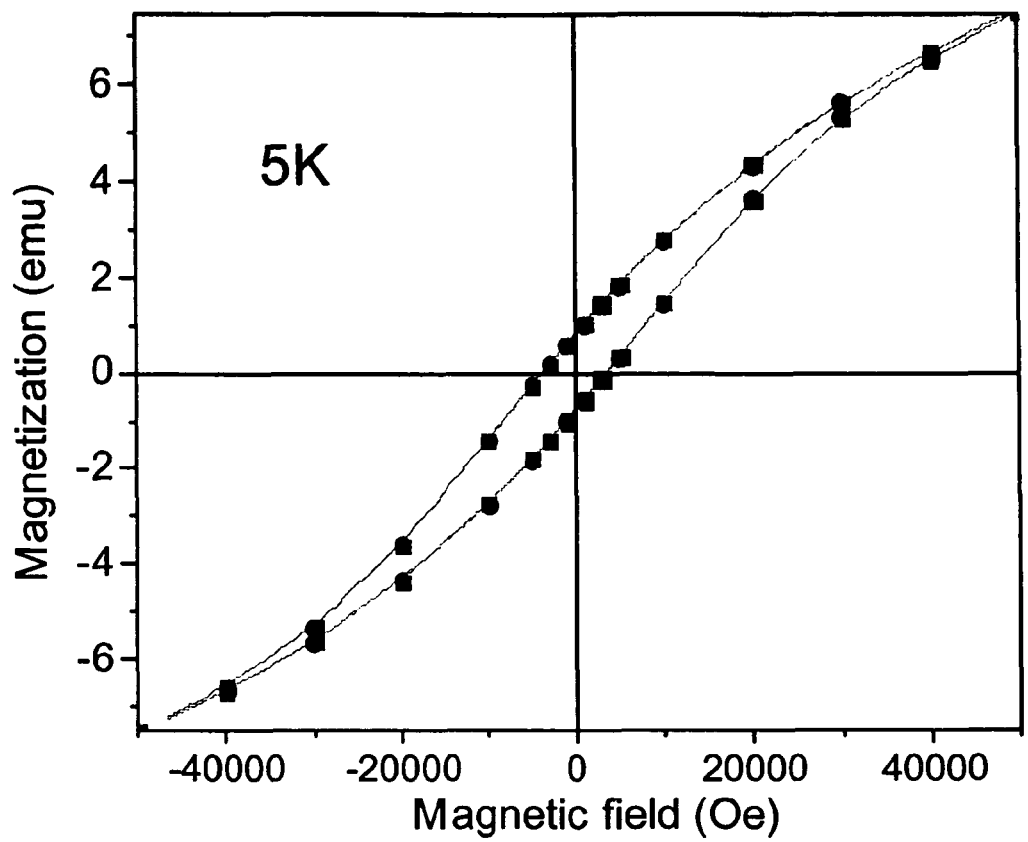
Figure 4D:
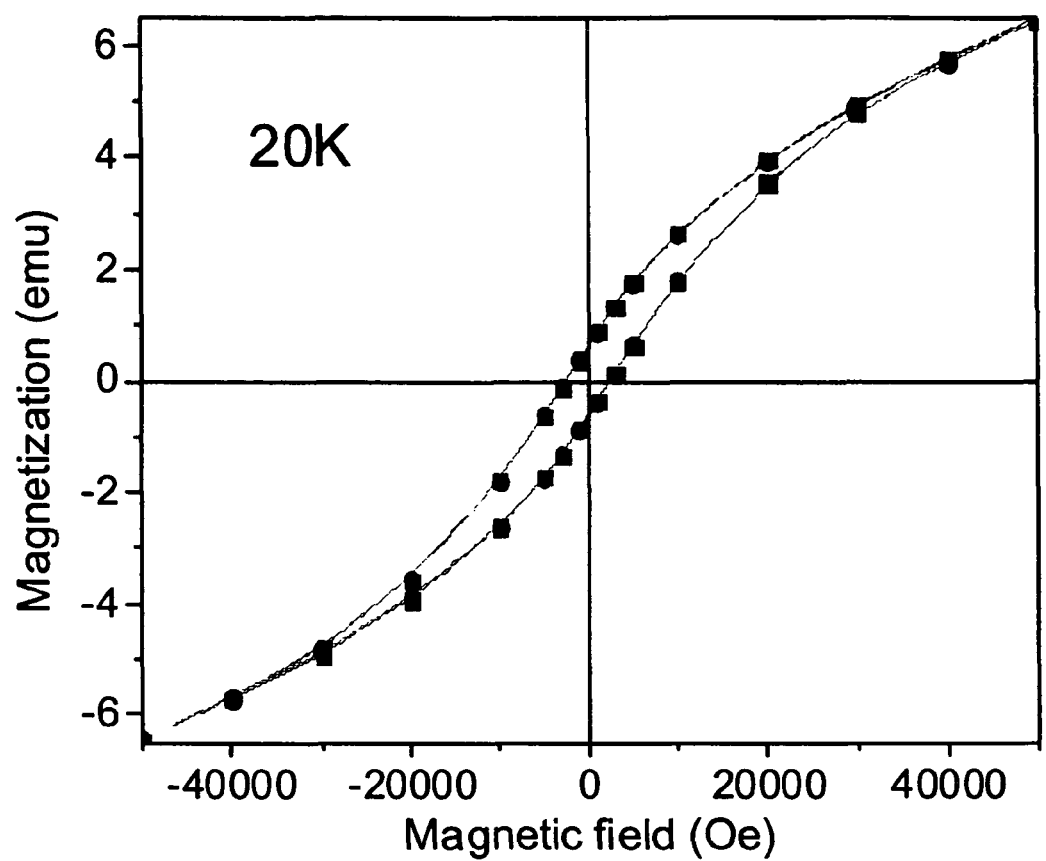
Figure 4E:
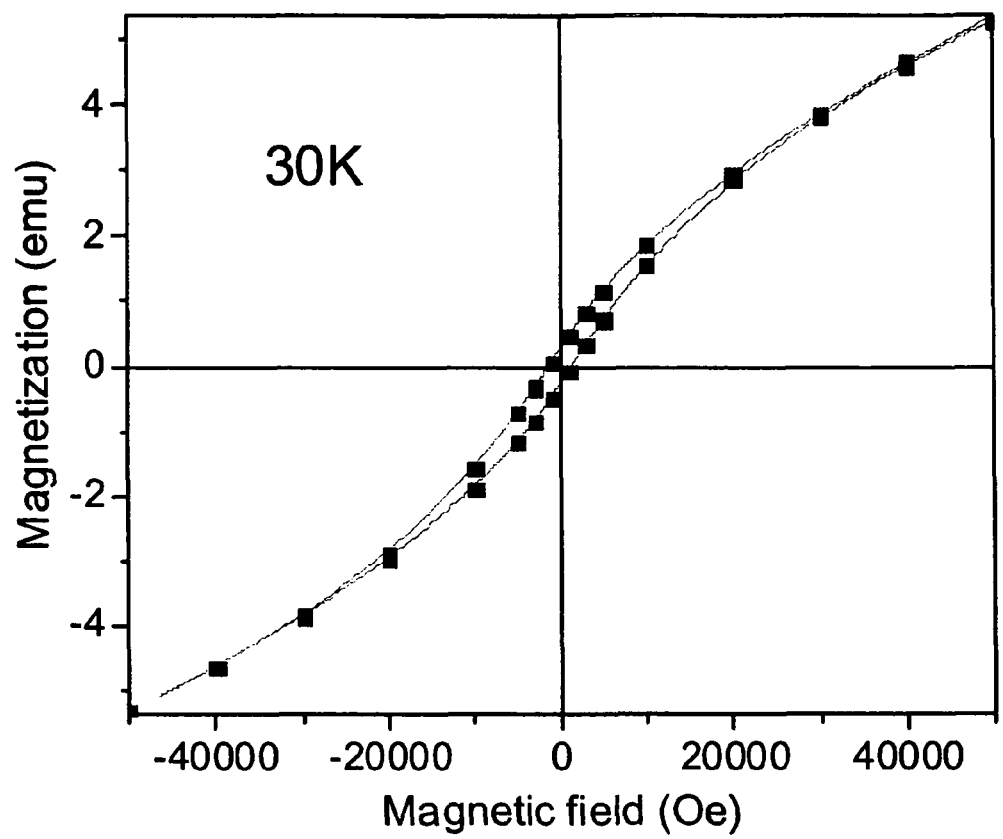
Figure 4F:
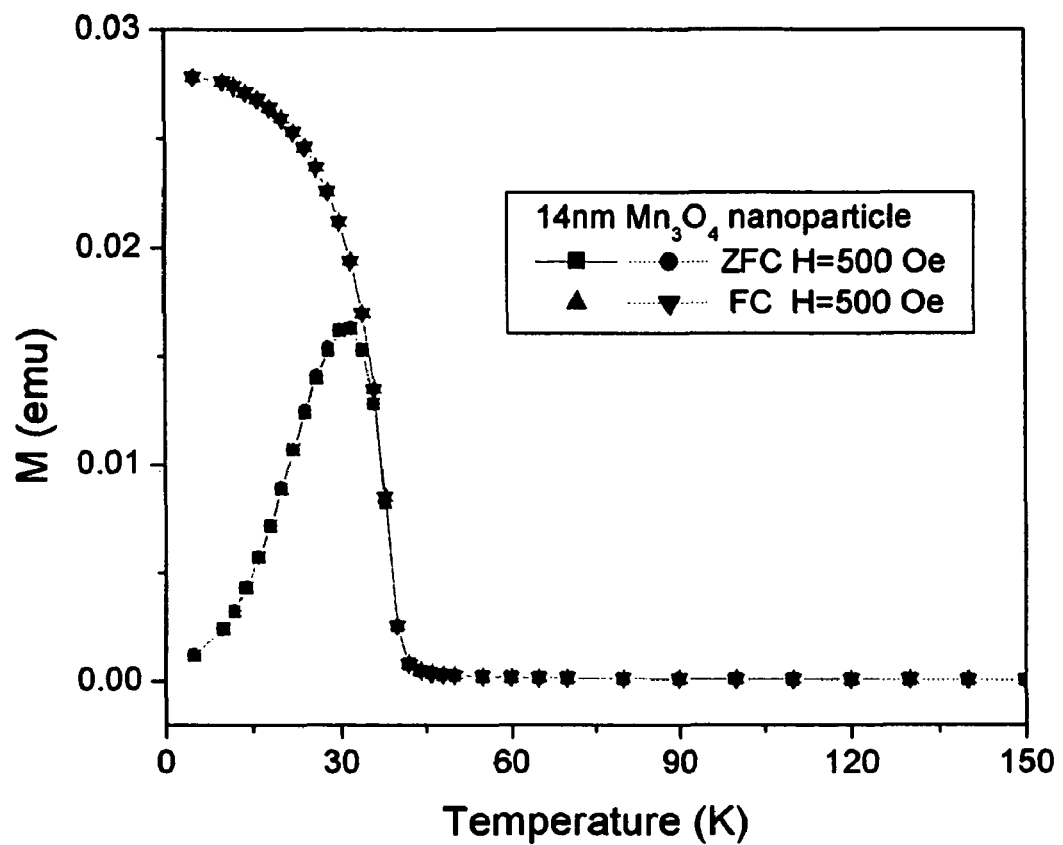
FIGS. 4F-4L depict analyses of the magnetic properties of $Mn_3O_4$ nanoparticles.
Figure 4G:
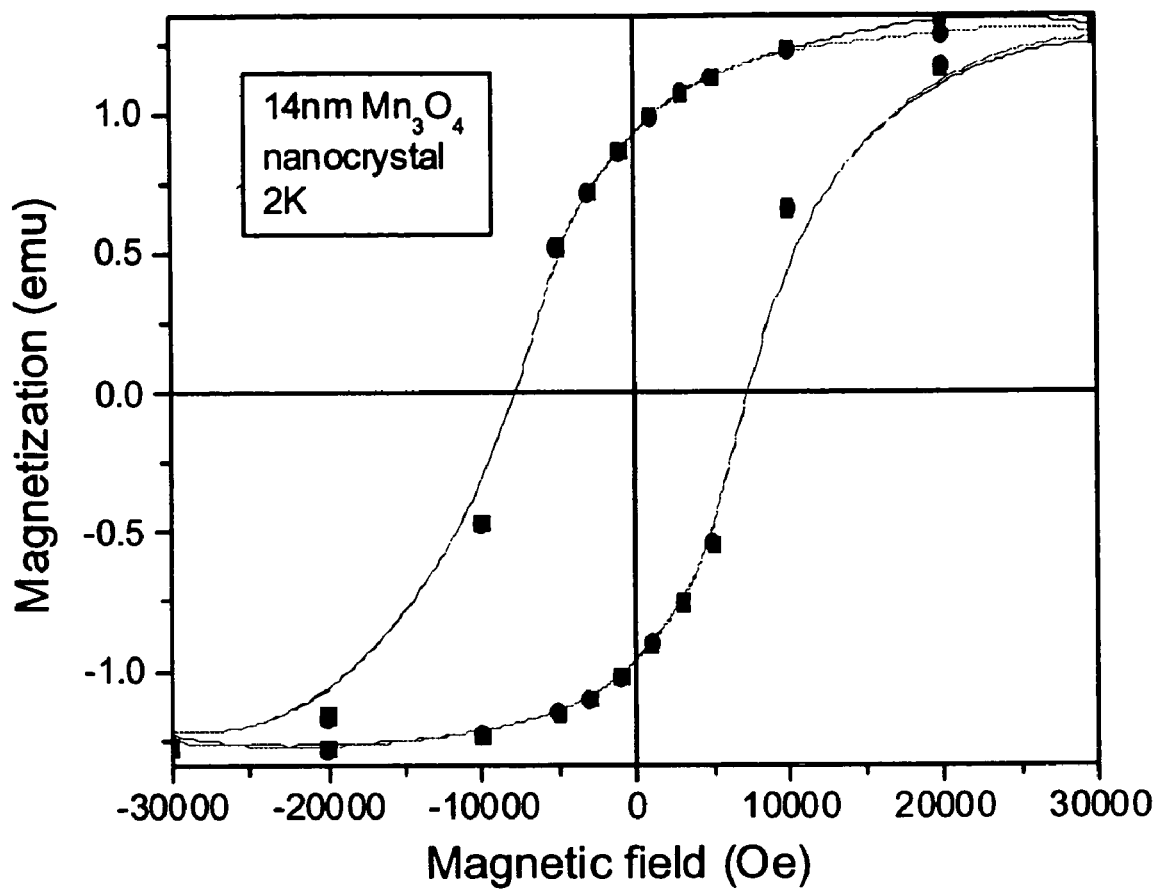
Figure 4H:
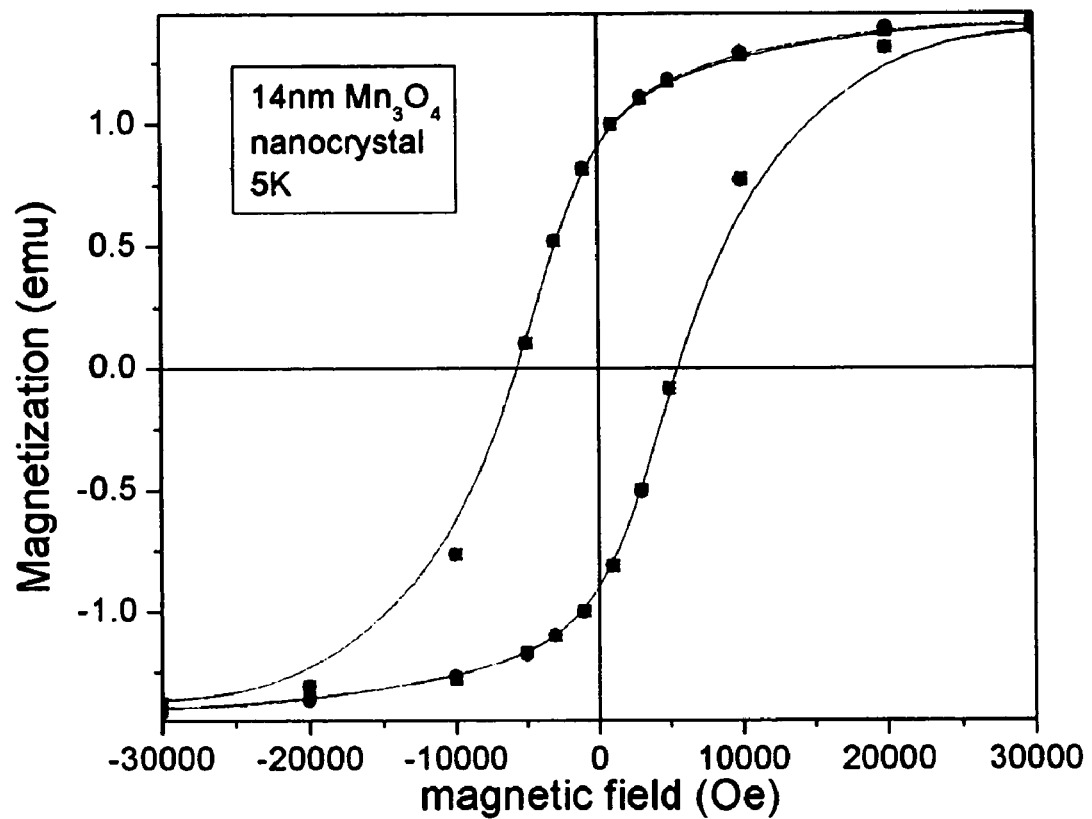
Figure 4I:
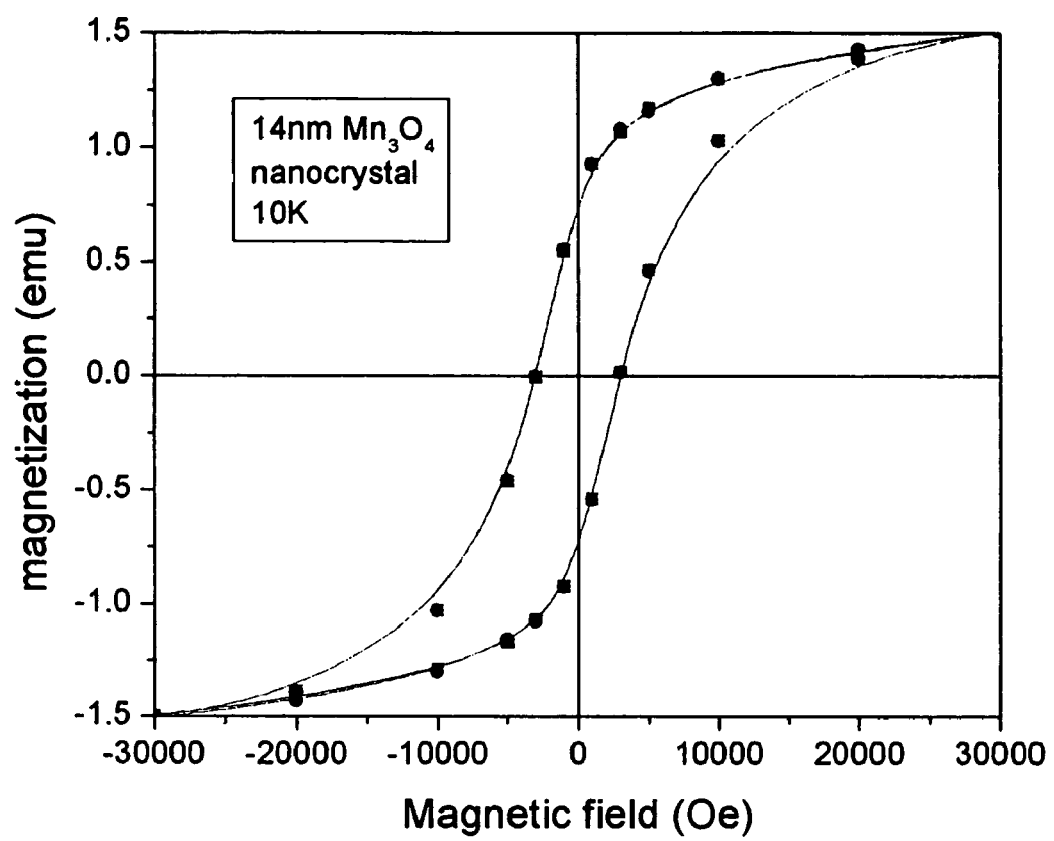
Figure 4J:
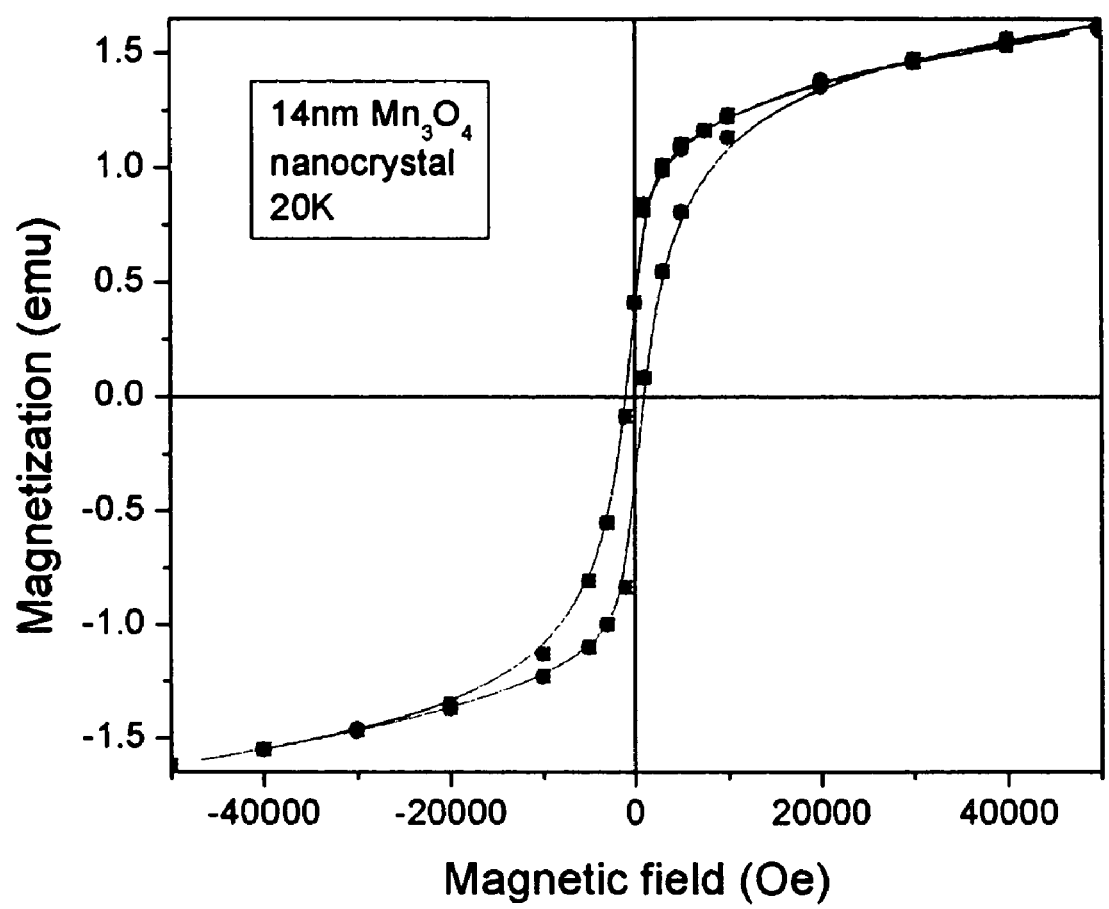
Figure 4K:
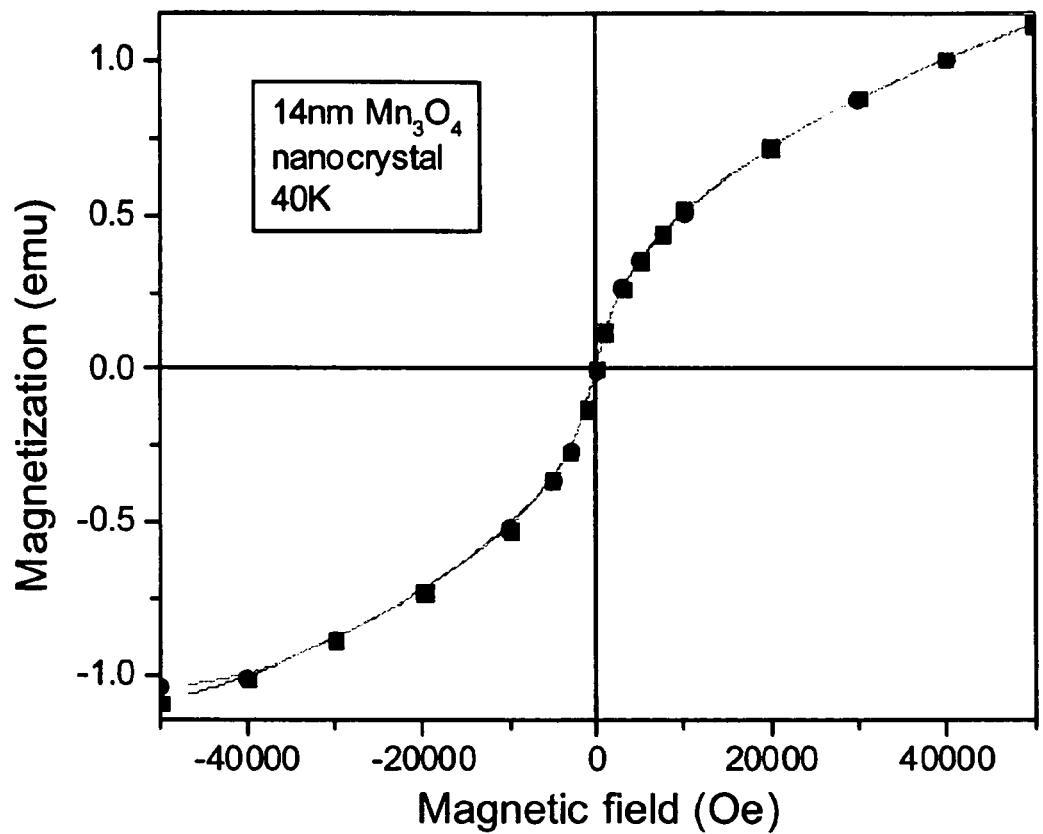
Figure 4L:
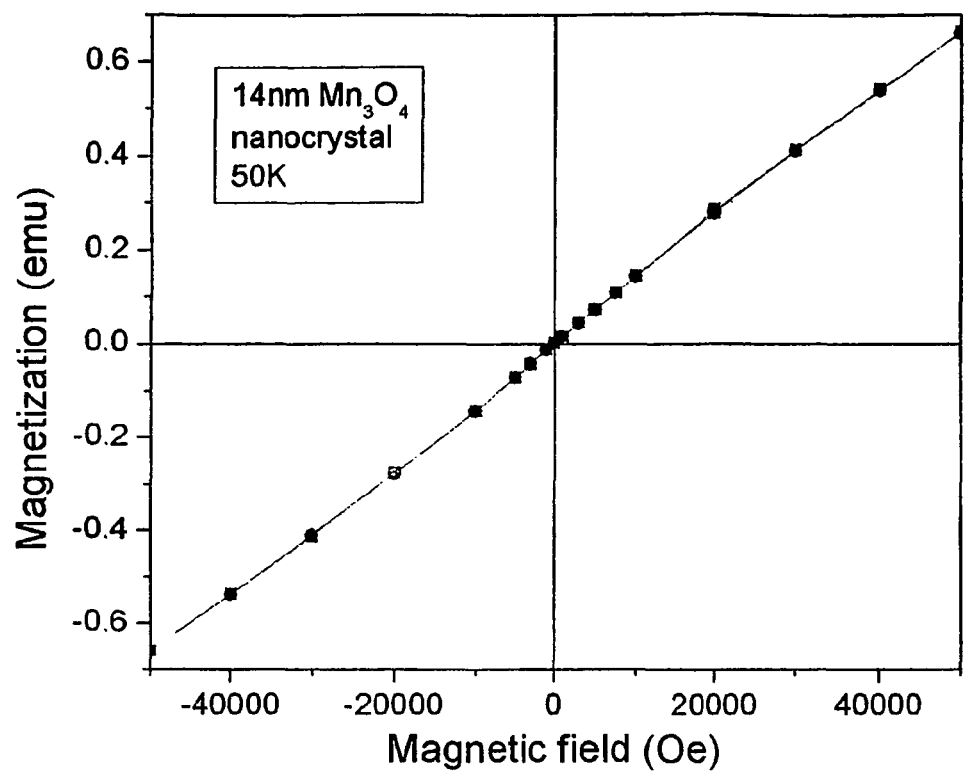
Figure 5A:
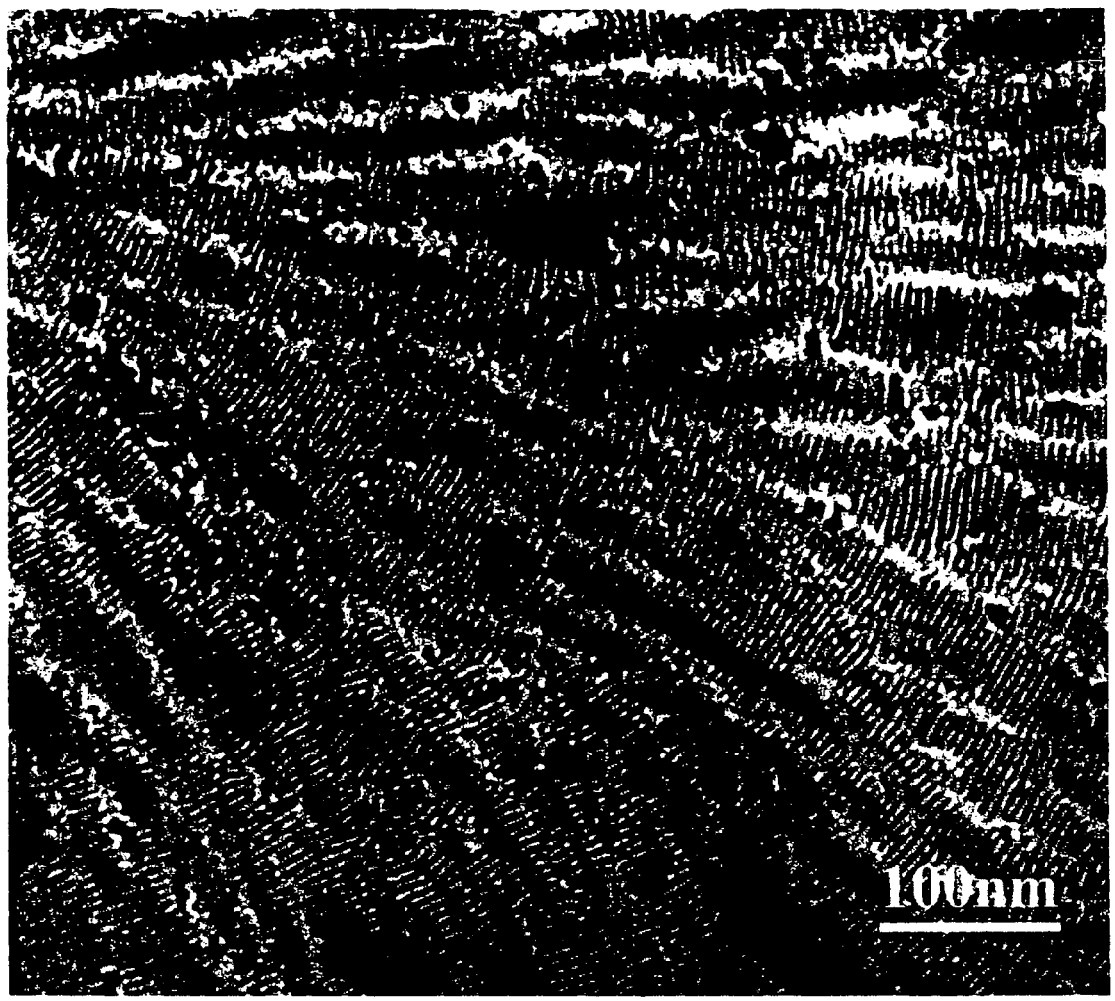
FIGS. 5A-5E show characteristics of ZnO nanoparticles synthesized by the methods of the present invention.
Figure 5B:
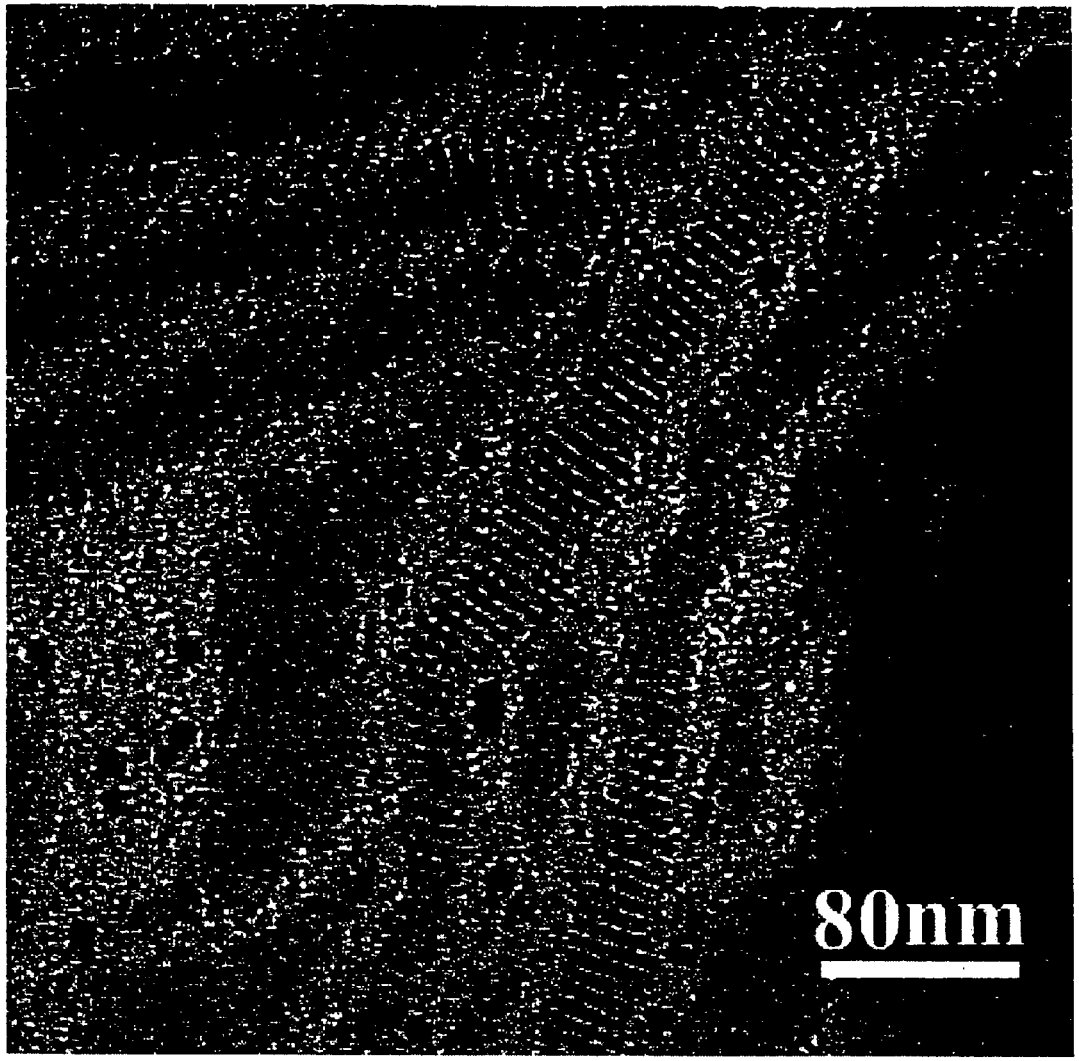
Figure 5C:
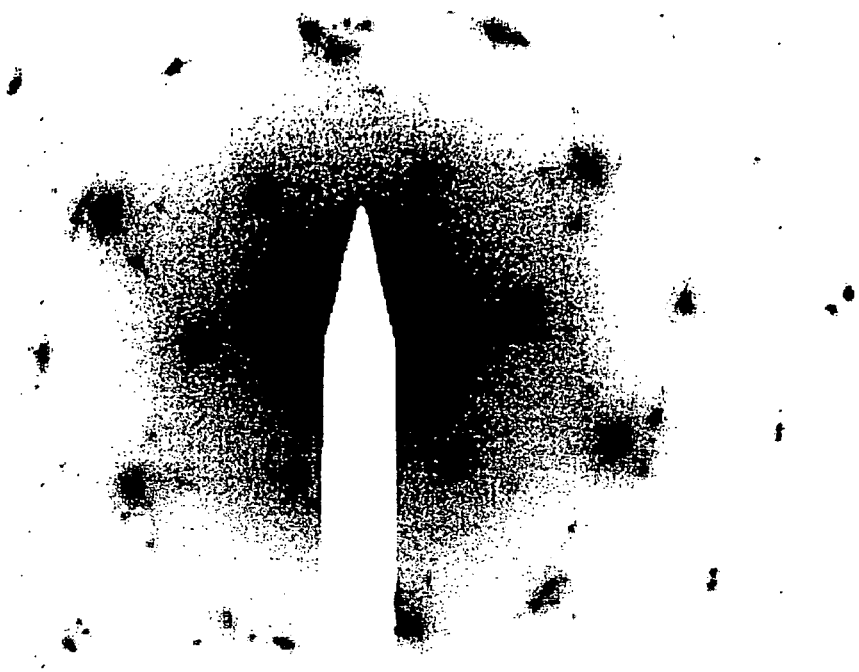
Figure 5D:
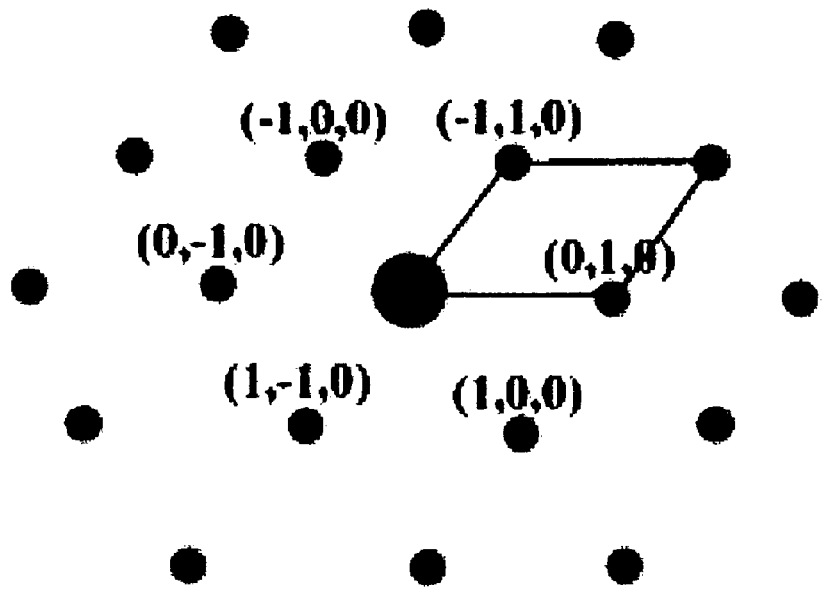
Figure 5E:
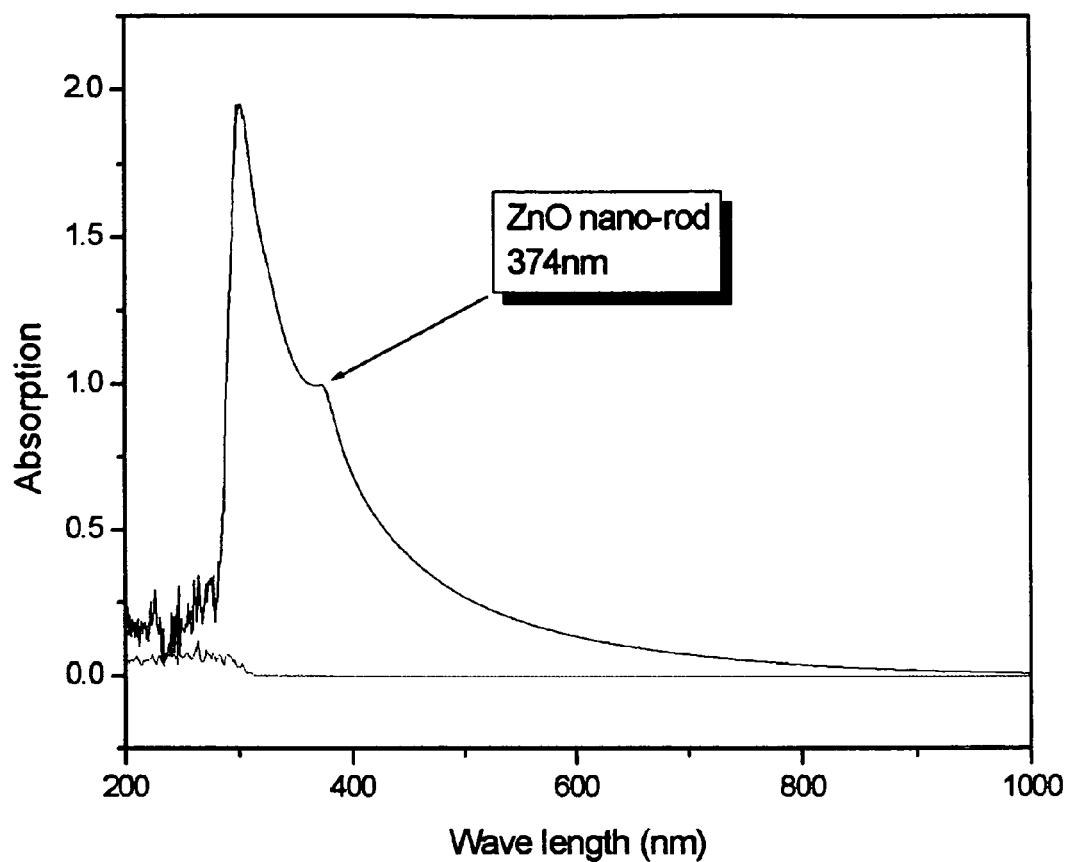

To extend the above experimental procedure to a wider range of binary transition metal oxides, chemical oxidation of 7 nm MnO nanocrystals with trimethylamine-N-oxide, $[CH_3]_3NO$, formed uniform and ligand-capped 7 nm nanocrystals of $Mn_3O_4$ (hausmannite structure, /4// amd, a=5.762 angstroms, c=9.470 angstroms), as characterized by TEM and XRD. (FIGS. 3A-3C). (See, e.g., T. Hyeon et al., 2001, *J. Am. Chem. Soc.*, 123:12798). In this aspect, stoichiometric ratios were in the range of 2-6 times the molar ratio of oxidant: metal precursor, e.g., 1 $Mn(CH_3CO_2)_2$:4$[CH_3]_3NO$. In addition, highly uniform preparations of ligand-capped nanocrystals of FeO (Wurstite structure, Fm3m) of 14 nm in size were formed using the method as described for MnO, by substituting Fe(II) acetate as the precursor. Following this method, magnetic measurements showed that the as-synthesized MnO and $Mn_3O_4$ nanoparticles were superparamagnetic at room temperature, as determined on a superconducting quantum interference device (SQUID) with typical fields and temperatures of 2-3000 K. (FIGS. 4A-4E, MnO; FIGS. 4C-4I, $Mn_3O_4$). (See, e.g., M. Yin and S. O'Brien, 2003, *J. Am. Chem. Soc.*, 125:10180-10181).

Example 2

This Example describes the formation of FeO nanoparticles prepared using the new synthesis according to the present invention. This method affords better control of the oxidation states of iron. In the method, dehydrated iron acetate (i.e., $Fe^{2+}$ salt) was used as the iron precursor and monodispersed, metastable wustite phase FeO nanocrystals were synthesized. In the reaction, dry iron acetate was mixed with trioctylamine organic solvent (10-20 mL) containing oleic acid as surfactant/stabilizing ligand (2-5 mL), and the mixture was heated over 10 to 15 minutes to a temperature of 250° C. The reaction was kept at this temperature for 1 hour under $N_2$. Thereafter, the FeO nanoparticles were cooled to 100° C., and were extracted into hexane by precipitation with ethanol, followed by centrifugation and redispersion in hexane as described hereinabove. The resulting nanocrystals were characterized using TEM (JEOL, 100cx, acc. 100 kV) and X-ray powder diffraction (XRD, Scintag $X_2$), as described in Example 1. Further oxidized forms of iron oxide, e.g., $Fe_2O_3$ and $Fe_3O_4$, nanoparticles were prepared using oxidizing agents in the synthetic process. Trimethylamine N-oxide is one example of an oxidizing agent that can be used in this example. Other oxidants include pyridine N-oxide ($C_5H_5NO$), phenyl sulfoxide ($C_{12}H_{10}SO$) and dimethyl sulfoxide ($[CH_3]_2SO$). After the FeO particles were prepared, the solution was cooled to room temperature, and then oxidants were added. Thereafter, the temperature was again raised to 200-300° C. and the FeO nanoparticles were oxidized to a higher oxidation status, i.e., $Fe_3O_4$ or $Fe_2O_3$. Both forms of iron oxide have superior magnetic properties.

Example 3

This Example describes the formation of $Cu_2O$ nanoparticles prepared using the synthesis methods according to the present invention. This method affords better control of the formation of $Cu_2O$ and further oxidation to CuO nanoparticles. Using the method of the invention, rated copper acetate was used as the copper precursor and monodispersed, metastable cuprite phase $Cu_2O$ nanocrystals (2 nm to 50 nm) were synthesized. The copper acetate starting material was mixed with a trioctylamine organic solvent containing oleic acid and was heated to 280° C. over a 10 to 15 minute time period. The reaction was maintained at the high temperature for about 1 hour under $N_2$. The reaction vessel was cooled to room temperature, and copper oxide nanocrystals were extracted into hexane by precipitation with ethanol, followed by centrifugation and redispersion in hexane as described above. The resulting $Cu_2O$ nanoparticles were analyzed by XRD and TEM as shown in FIGS. 9A-9G. Further oxidized CuO nanoparticles could also be prepared by further oxidation of $Cu_2O$ nanoparticles by using the oxidants described in Example 2. Such copper oxide nanoparticles are suitable for use as material comprising solar batteries, for example.

Copper Oxide Nanocrystals: Inorganic nanocrystals are a benchmark model for nanotechnology, given that the tunability of optical properties, and the stabilization of specific phases are uniquely possible at the nanoscale. As discussed herein, copper (I) oxide ($Cu_2O$) is a metal-oxide semiconductor with promising applications in solar energy conversion and catalysis. To understand the Cu/$Cu_2O$/CuO system at the nanoscale, the invention provides a method for preparing highly uniform monodisperse nanocrystals of $Cu_2O$. The synthetic procedure serves to demonstrate our development of a generalized method for the synthesis of transition metal oxide nanocrystals, which involves thermal decomposition of metal acetate-surfactant complexes in hot organic solvents. In this case Cu nanocrystals are formed and are subsequently oxidized to form highly crystalline copper (I) oxide, $Cu_2O$. Interestingly, the transformation of Cu nanocrystals to $Cu_2O$ can induce crystal twinning. This invention is based on a surprising discovery that the copper (I) oxide phase is well-stabilized at this lengthscale.

Copper (I) oxide ($Cu_2O$) is a p-type metal-oxide semiconductor with promising applications in solar energy conversion and catalysis. (1-4, wherein the numbers in parenthesis for Example 3 refer to references as set forth below herein). There is much interest in $Cu_2O$, also called cuprous oxide, due to its rich excitonic structure. The large excitonic binding energy (140 meV) allows the observation of a well-defined series of excitonic features in the absorption and luminescence spectrum at low temperature, (5,6) yet studying quantum confinement effects or modifying the behavior of the direct forbidden band gap is challenging. (7,8) It is also a useful compound to study the influence of electron-correlation effects on the electronic structure of transition metal compounds in general, and the high $T_c$ superconductors in particular. (2) Although the absorption characteristics of the various exciton series for copper (I) oxide have been studied. (5,9-13) Most samples have been limited to bulk, micro sized or nanopowders. The invention provides for a procedure by which discrete, monodisperse and uniform nanocrystals of pure copper are extracted from solution, which can be completely oxidized to $Cu_2O$. $Cu_2O$ is a prospective candidate for low-cost photovoltaic applications due to its high optical absorption coefficient, lower band gap energy (2.2 eV), and simplicity of preparation, scalability, the non-toxic nature, the abundance and the economics of the material. Further opportunities in catalysis could be realized through the preparation of self-assembled nanostructures and stabilization of specific phases of copper oxide. Therefore, it is of interest to prepare high quality, monodisperse copper oxide nanocrystals, to examine their structure and characterize their optical properties. An investigation and understanding of size effects in such a system is of interest due to the possibility of tuning its opto-electronic properties. Substantial effort has been devoted to the $Cu/Cu_2O/CuO$ system in the 1-500 nanometer range. (14-18) The approach of the present invention involves thermal decomposition of copper (I) acetate at high temperature, in the presence of a surfactant. This results in highly monodisperse and crystalline nanoparticles of $Cu_2O$, with a mean particle size tunable from 3.6±0.8 nm to 10.7±0.7 nm (based upon the stoichiometric ratio of surfactant to copper precursor). Evidence of $Cu^{2+}$ in the XPS and optical characterization of the nanocrystals suggested the existence of a thin layer of CuO at the nanocrystal-ligand interface.

Crystals of a finite size assume a modified morphology and/or crystal structure in order that the atoms, especially those at the surface, can adopt the most stable equilibrium configuration of minimal energy. (2) Consequently, some materials, which are not stable in bulk and do not exist in ambient atmosphere, may become substantially more stable at the nanoscale. This is due to the large contribution of surface energy which can stabilize the origin of unique phases. (19-21) Bulk $Cu_2O$, with a cuprite structure, absorbs oxygen from the air and can readily convert to CuO at room temperature. (2)

Figure 11:
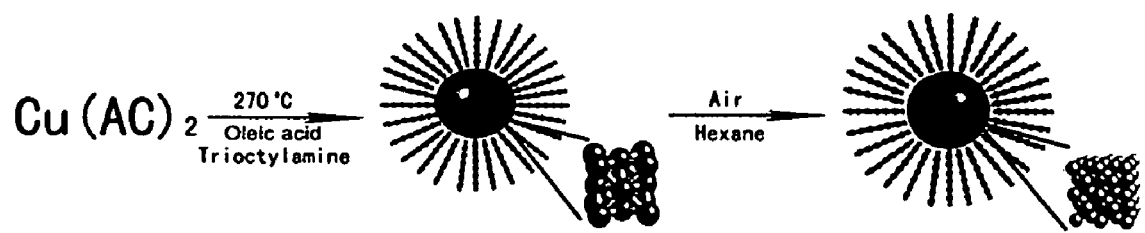
FIG. 11 illustrates a synthetic procedure for $Cu_2O$ nanocrystals.

The synthetic procedure used for the $Cu/Cu_2O/CuO$ system serves to illustrate our development of a generalized method for the synthesis of transition metal oxide nanocrystals, which involves metal acetates as the precursors and thermal decomposition of metal acetate-surfactant complex in a hot organic solvent. (23,24) In some places herein and elsewhere this method is termed "TDMA" (thermal decomposition of metal acetates). The method is effective for the synthesis of 1st row transition metal and transition metal oxide nanocrystals (FIG. 11). (25) The method of the invention insures the preparation of highly uniform, monodisperse nanocrystals of $Cu_2O$ in high yield (typically >50-60% wrt conversion of precursor). Synthesis of transition metal oxide nanocrystals by choosing their acetates as precursors is simple and relatively safe. (23,24) The experiments performed show that generally, the standard deviation of the size of nanocrystals prepared with solvent degassing (to remove $O_2$) is less than 5%, without further size selection. The as-synthesized nanocrystals have a capping coordination sphere of oleic acid, which stablilizes them in solution, prevents aggregation and allows them to form close packed superlattice structures following evaporation of the solvent.

Figure 10:
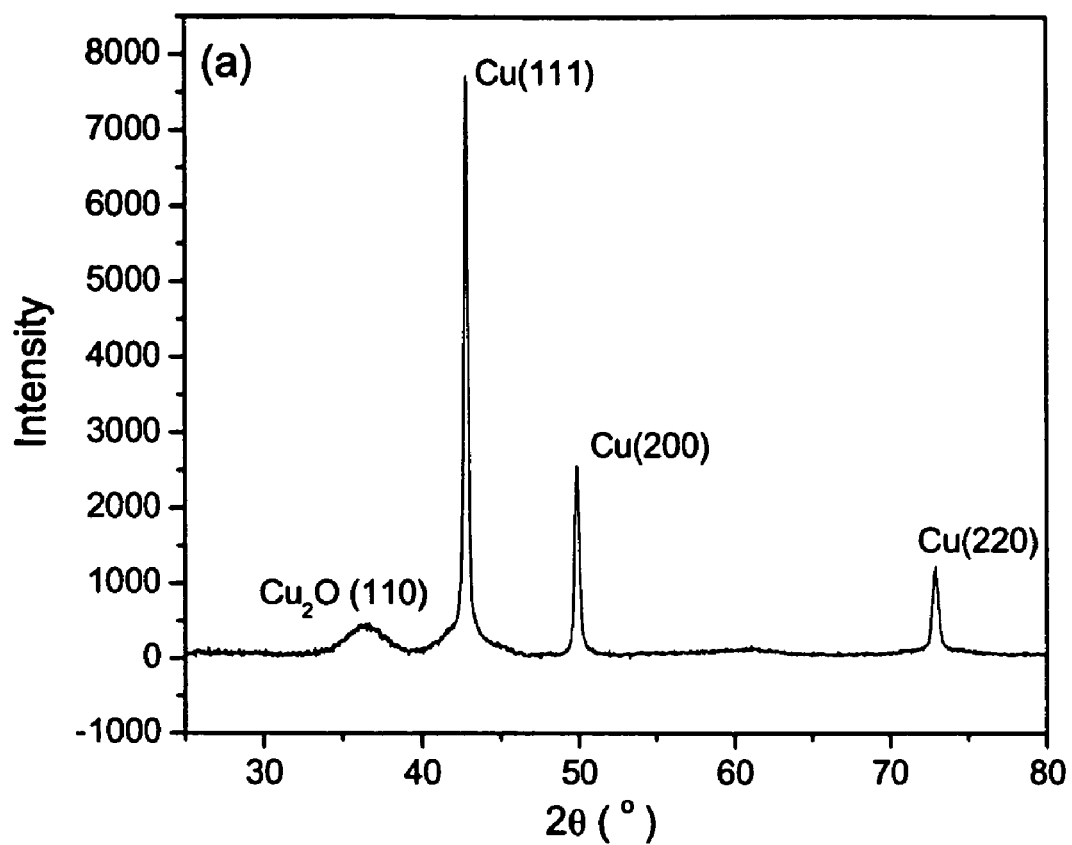
FIGS. 10A-10B illustrate (FIG. 10A) X-ray powder diffraction patterns of 5 nm fcc Cu nanocrystals, 10 minutes after synthesis and extraction from solution and (FIG. 10B) X-ray powder diffraction patterns of 5 nm cuprite $Cu_2O$ nanocrystals, sample prepared after oxidation.
Figure 10:
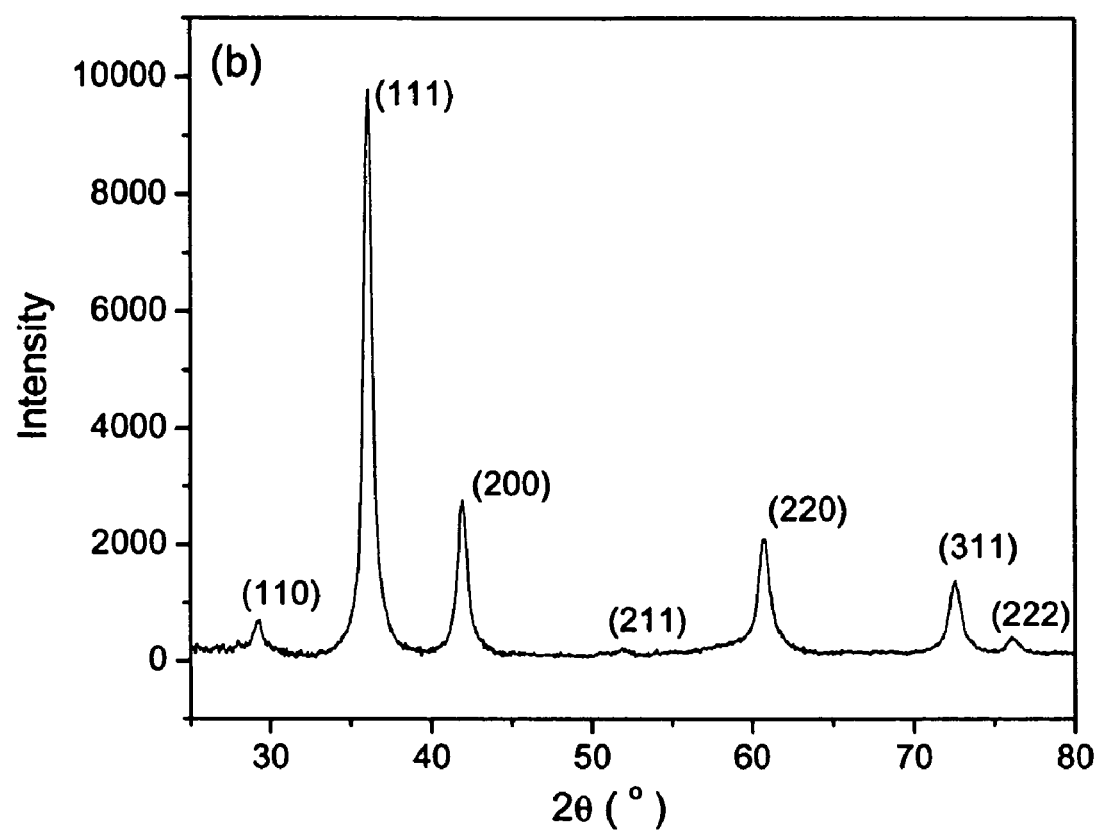
Figure 16:
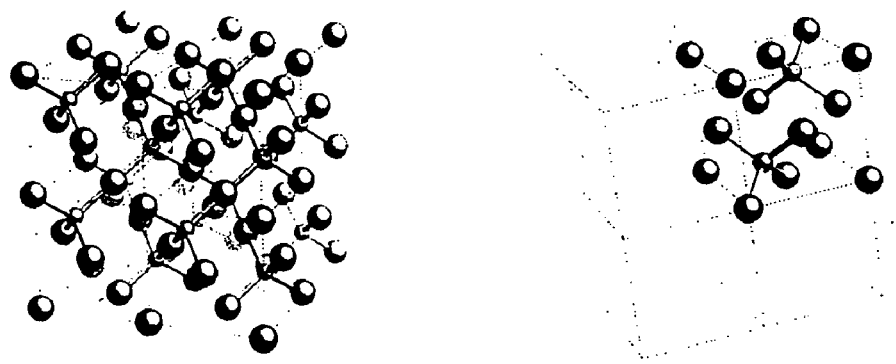
FIG. 16 shows a stick and ball model of the crystal structure of cuprite $Cu_2O$.

In order to obtain evidence that the nanoparticles formed in situ are initially pure copper nanocrystals, X-ray powder diffraction was performed immediately after sample preparation. The peaks in the XRD could be indexed to the fcc structure of metal copper (Fm-3m, a=3.615, JCPDF# 85-1326) (FIG. 10A). Only a very small peak of $Cu_2O$ (110) was detected (and was also observed to grow slightly during XRD measurement), ascribed to nanocrystal oxidation post synthesis. After precipitation, if the nanoparticles are dissolved in hexane and exposed to air, the color of the nanoparticle solution turns to dark green, commensurate with oxidation to $Cu_2O$. XRD of this nanocrystal sample show that all of the peaks match well with Bragg reflections of the standard cubic cuprite structure (Pn-3m, a=4.258 Å, JCPDF # 78-2076) as shown in FIG. 10B. The process of full oxidation from Cu to $Cu_2O$ nanocrystals can take up to a few hours depending on the conditions and particle size but in all cases transformation to $Cu_2O$ is complete, in contrast to previous reports. (17) The crystal structure of $Cu_2O$ is cuprite, which is composed of 8 cubes, as shown in s-FIG. 16. In each cube, Cu atoms occupy all the fcc positions and two oxygen atoms occupy two diagonal tetrahedral interstices. The oxidation can be qualitatively interpreted as an oxygen diffusion and lattice expansion process. When Cu nanocrystals are exposed to air, electrons are transferred from Cu atoms to oxygen and the oxygen anions produced diffuse in the tetrahedral interstices. As a result, the crystal structure and material changes from fcc Cu to cuprite $Cu_2O$ with a corresponding lattice expansion (see FIGS. 12-15). Cu and $Cu_2O$ share the high-symmetry cubic structure, while CuO is a low-symmetry monoclinic structure. The oxidation transition to $Cu_2O$ is accomplished by oxygen atoms' diffusion into tetrahedral interstices and lattice expansion. However, there is a considerable energetic difference between the fcc structure (Cu) and monoclinic structure (CuO), as atom rearrangement and lattice/unit cell reconstruction is required, which may help to explain why the transformation to crystalline CuO does not occur in these nanocrystals. Detailed structural analysis presented here reveals the presence of $Cu^{2+}$ ions predominately at the surface, attributed to a thin layer of amorphous CuO which may also serve as a kinetic stabilization with respect to further oxidation. The results presented here are consistent with other observations of $Cu_2O$ stability at the nanoscale. (22)

Figure 12A:
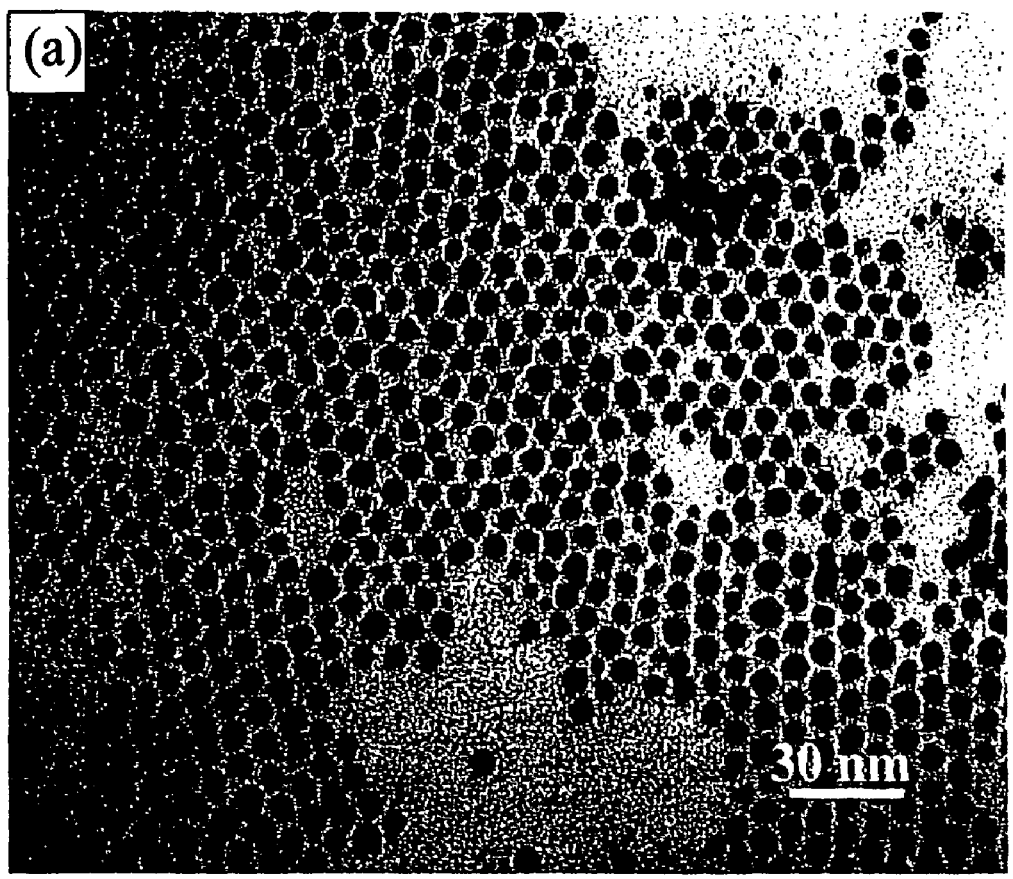
FIGS. 12A-12C show transmission electron micrograph (TEM) of self-assembled 6 nm diameter $Cu_2O$ Nanocrystals (FIG. 12A); TEM image showing a larger area view of a close-packed superlattice of 6 nm $Cu_2O$ nanocrystals (FIG. 12B) and high resolution image showing the single crystal and high crystallinity (FIG. 12C).
Figure 12B:
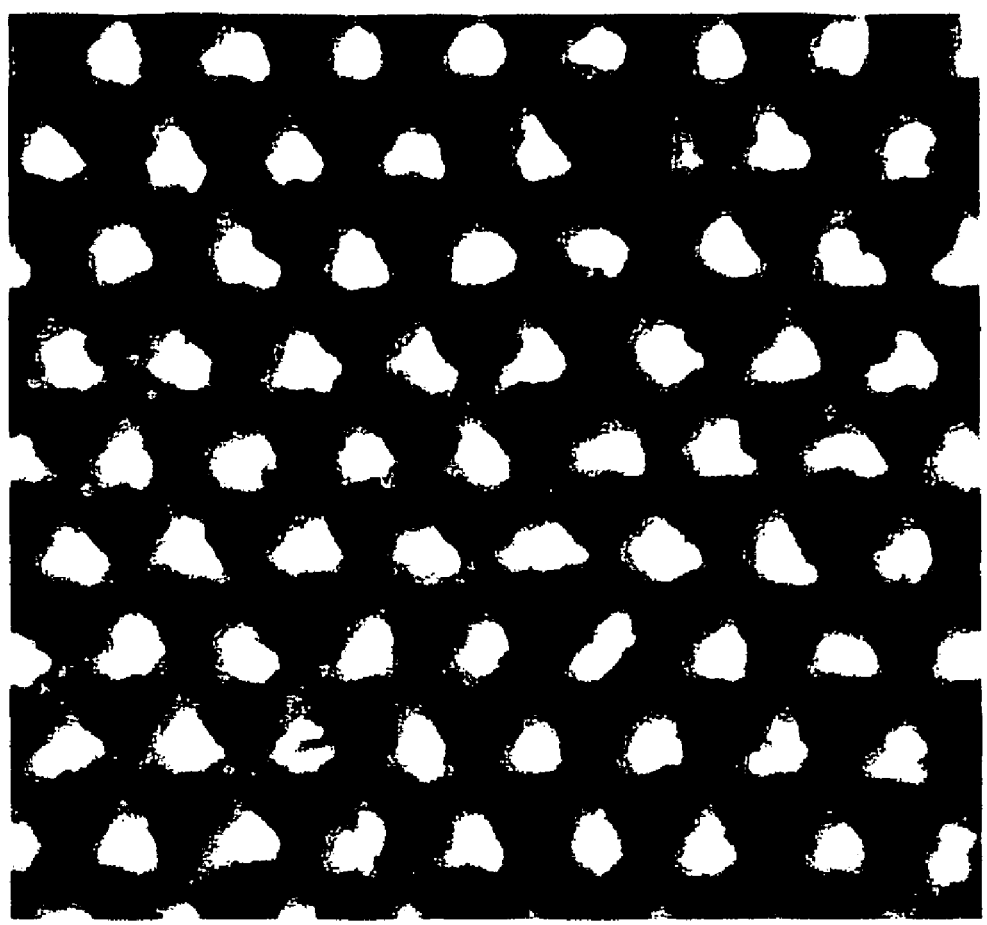
Figure 12C:
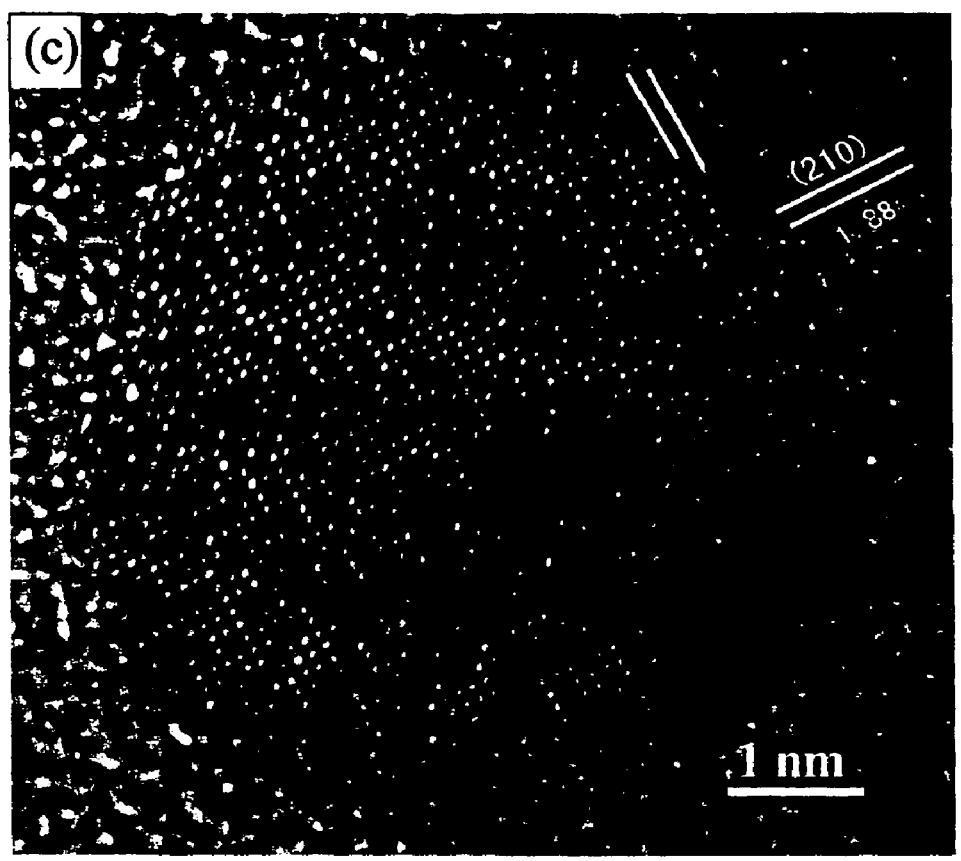
Figure 12D:
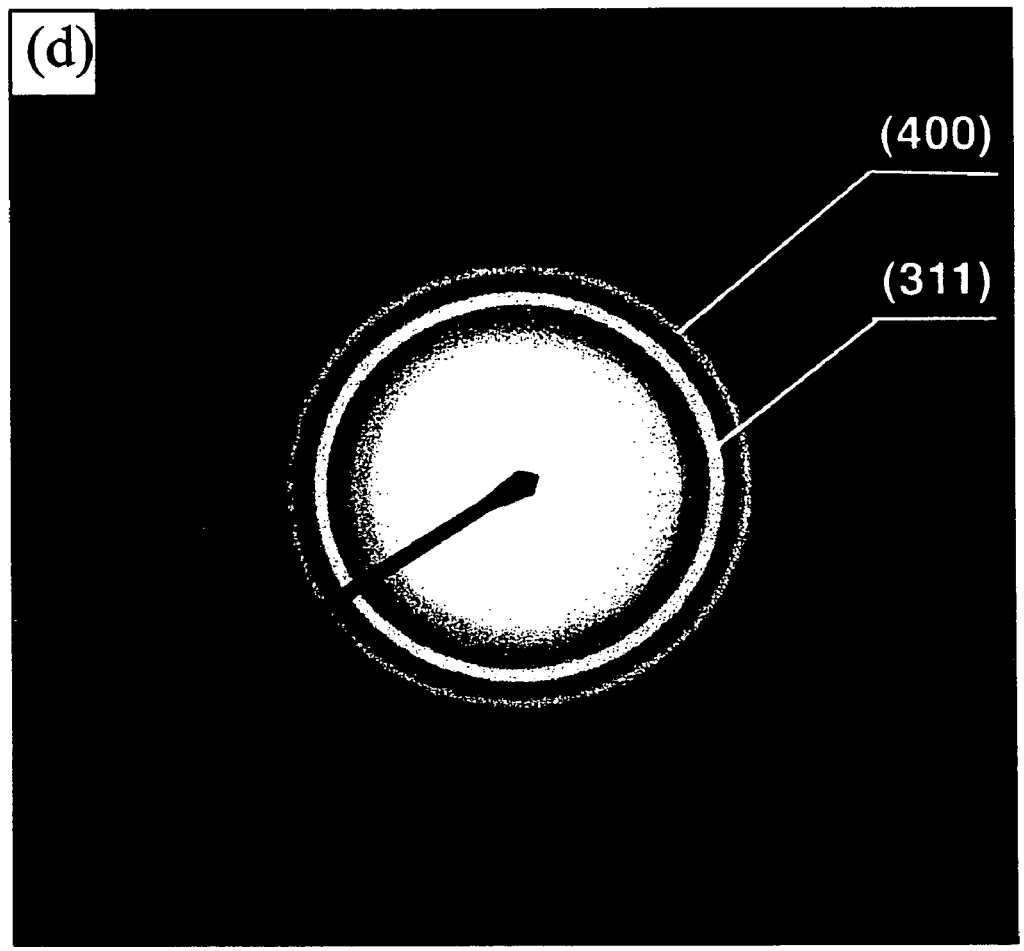
FIG. 12D shows a selected area electron diffraction pattern of $Cu_2O$ nancrystals.
Figure 13:
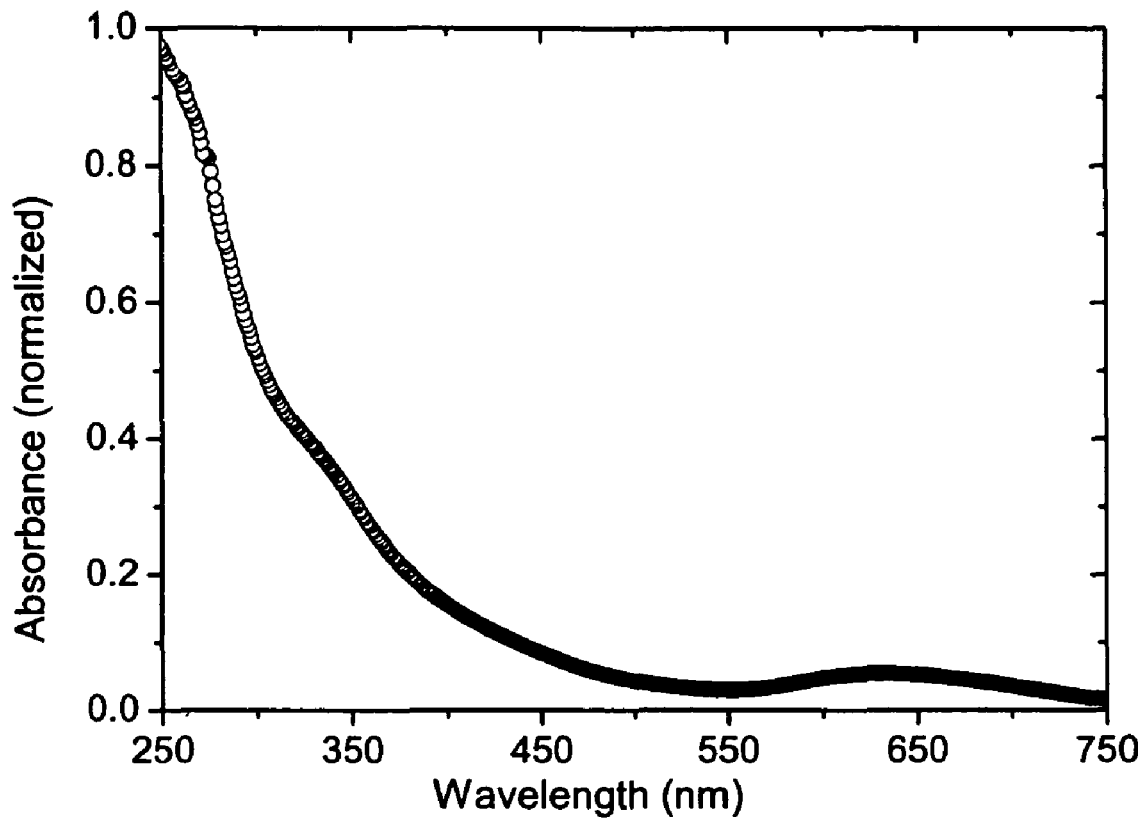
FIG. 13 shows UV-vis spectrum of as-prepared $Cu_2O$ nanocrystals in hexane at 298 K.
Figure 14A:
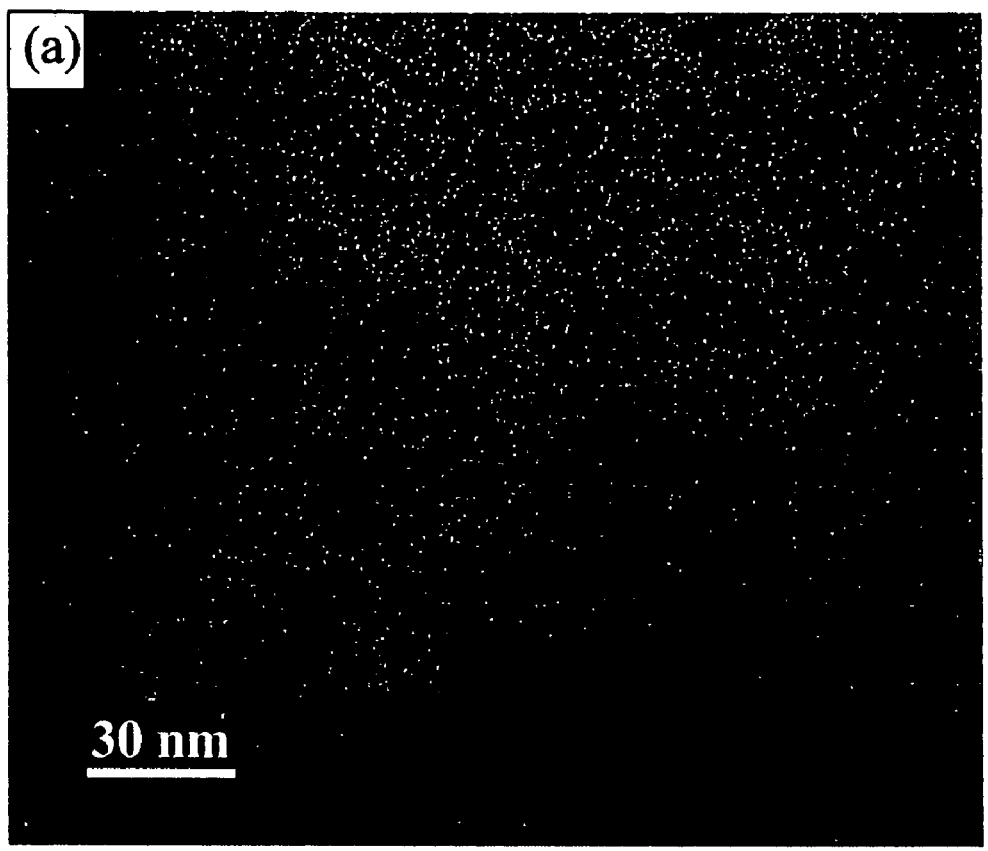
FIGS. 14A-14B show transmission electron micrograph of 5.1±0.5 nm diameter Cu nanocrystal (FIG. 14A) and corresponding 6.1±0.9 nm diameter $Cu_2O$ nanocrystal (FIG. 14B), showing a 19.6% volume increase after oxidation; insert: Selected area electron diffraction pattern.
Figure 14B:
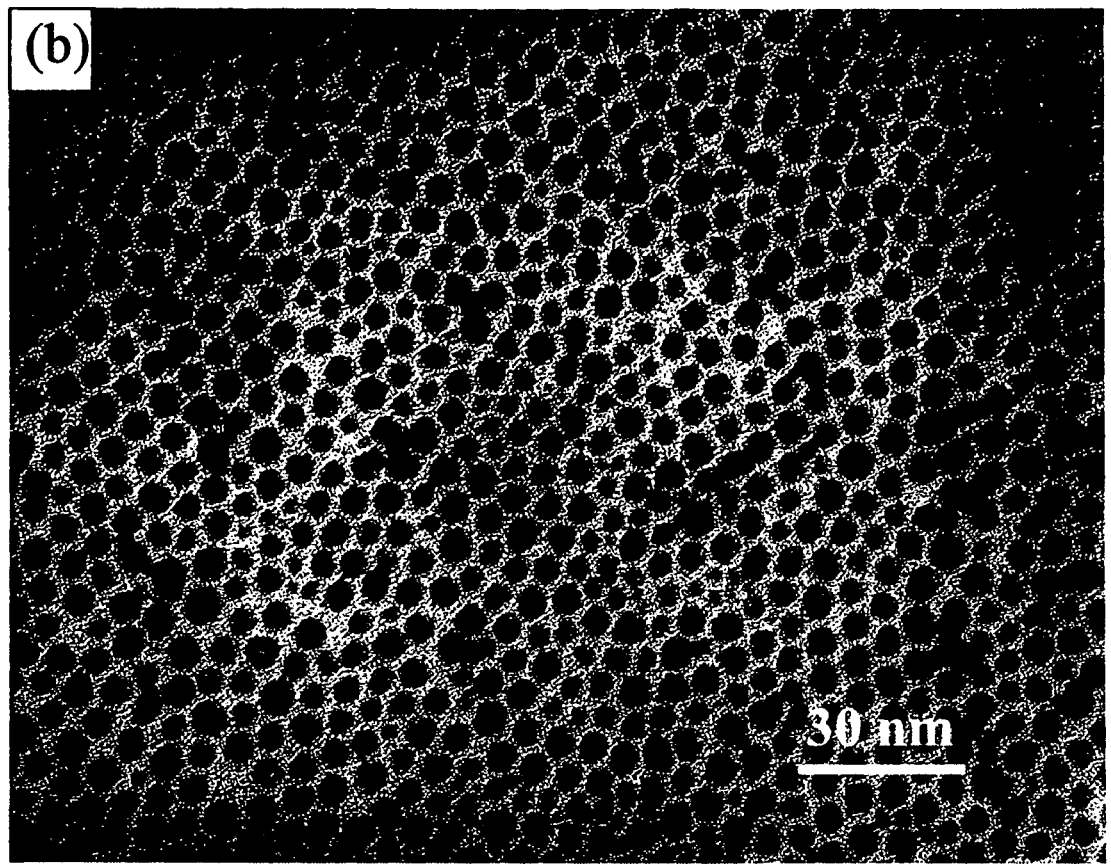
Figure 15:
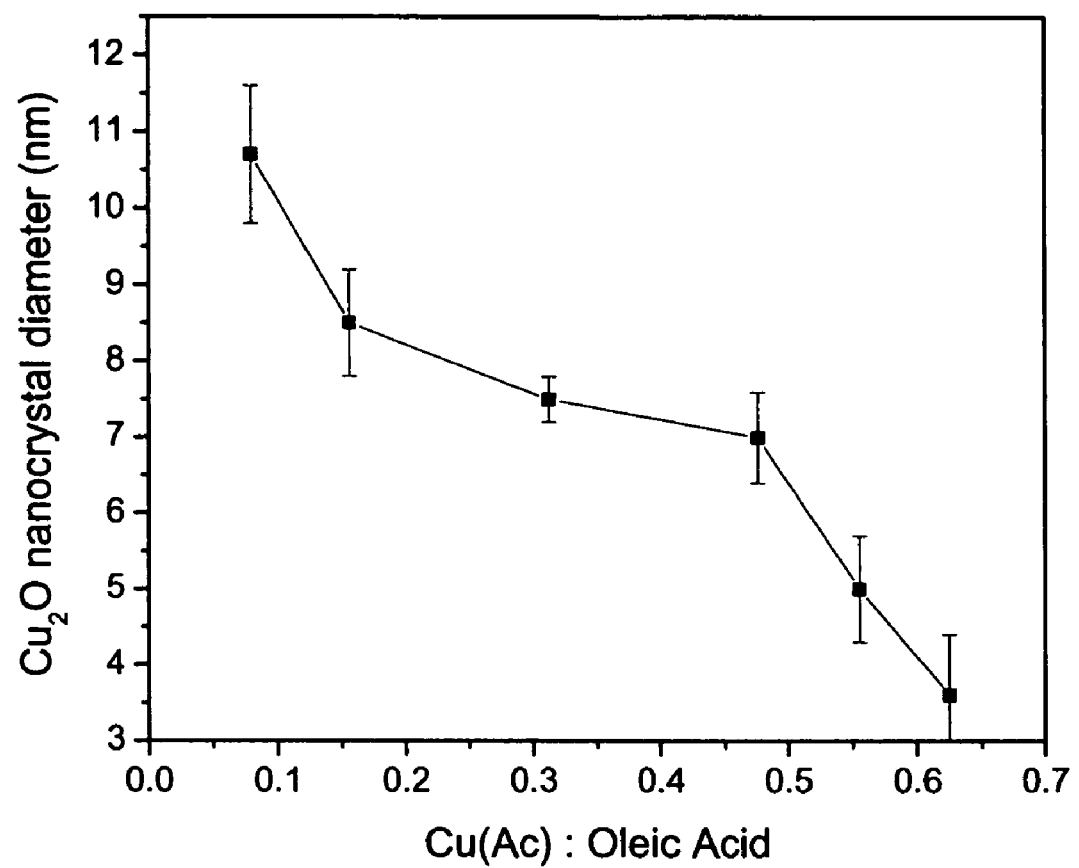
FIG. 15 shows a plot of particle size vs the relative amount of oleic acid to copper (I) acetate, showing the diameter of the final product increases with a increased OA:$Cu(Ac)_2$ ratio.

Nanocrystal assembly from hexane solutions into closed packed arrays was also observed in FIG. 12A, and 13A, demonstrating the uniformity of the particle size and retention of the oleic acid capping group. FIG. 12B shows a view of a close-packed superlattice of 6 nm $Cu_2O$ nanocrystals. The nanocrystals are clearly suitable candidates for the preparation of binary superlattice structures. (26) If the particle is oriented along a low-index zone axis, the distribution of atoms on can be imaged. FIG. 12C gives a profile HRTEM image of cubic $Cu_2O$ nanocrystals. The lattice plane distance is 1.88 Å, indicating (2 1 0) planes. Selected area electron diffraction patterns (FIG. 12D) can be indexed to cubic symmetry, indicating cubic crystal structure of $Cu_2O$.

The role of the capping ligand is very important to nanocrystal synthesis, during nucleation, growth and stabilization of the particles post-synthesis with respect to agglomeration and stabilization in organic solvents. A decrease of particle size from 10.7±0.7 nm to 3.6±0.8 nm was observed as the molar ratio of copper (I) acetate to oleic acid was increased from 0.08 to 0.6 (supporting information, FIG. 15). The ability of controlling particle size is of interest to prepare high quality, monodisperse cuprous oxide nanocrystals and to characterize their optical properties.

Monodisperse, stable $Cu_2O$ nanocrystals were synthesized by using a novel, yet simple wet chemistry route. This method gives a high yield of nanocrystals and narrow size distribution. The $Cu_2O$ nanocrystal size could be controlled from 3.6 nm to 10.7 nm by controlling the molar ratio of oleic acid to copper precursor. From structural analysis, it was concluded that the $Cu_2O$ phase is highly stabilized in these nanocrystals. The investigated $Cu_2O$ nanocrystals show a band gap transition. In addition, they display a band gap transition of the surface CuO layer. XPS reveals an amorphous layer of CuO on the $Cu_2O$ nanocrystal surface and the reduction of surface CuO to $Cu_2O$ by X-ray irradiation.

Nanocrystal Synthesis—Copper (I) acetate ($CH_3CO_2Cu$), trioctylamine ($[CH_3(CH_2)_7]_3N$), oleic acid ($CH_3(CH_2)_7$ $CH=CH(CH_2)_7CO_2H$), hexane, and ethanol were purchased from Aldrich and used as received. In a typical synthesis, a solution containing 4 mmol copper acetate, 4 ml oleic acid and 15 ml trioctylamine was quickly heated to 180° C. under Nitrogen, the color gradually changed from forest green to coffee, finally producing a gray colloid. The presence of oxygen or water is highly undesirable during the decomposition and nucleation stage. The solution was kept at this temperature for 1 hour. Then, it was quickly heated up to 270° C. The gray colloid gradually changed to a deep burgundy solution. The solution was kept at 270° C. for an hour before it was cooled down to RT (room temperature), and particles were precipitated by ethanol and redispersed in hexane. The particles (Cu) are observed to be initially dark red, forming a purple/dark-red solution when dispersed in hexane. The resulting red purple copper particles gradually oxidize to $Cu_2O$ in hexane, and produce a deep green solution. The final $Cu_2O$ nanocrystals were very stable in hexane, both with respect to oxidation and agglomeration, and ready to be used for further experiments.

TEM and XRD characterization—$Cu_2O$ nanocrystals were characterized using transmission electron microscopy (JEOL CX100) with an accelerating voltage of 100 kV, high resolution TEM (JEOL 3000F) with an accelerating voltage of 300 kV, and X-ray powder diffraction (Scintag X2 X-ray diffractometer). TEM samples were prepared by placing a drop of a dilute hexane dispersion of nanocrystals on the surface of a 400 mesh copper grid backed with Formvar, and were dried in a vacuum chamber for 1 hr. JEOL 3000F was used for lattice imaging. XRD samples were prepared by drying a dispersion of nanocrystals on a piece of Si (100) wafer.

UV-Vis characterization—The UV-vis absorbance and fluorescence spectra were measured on a Varian Cary 50 and a Varian Eclipse fluorescence spectrophotometer, respectively. XPS characterization. The XPS experiment was performed on PHI 5500 model spectrometer equipped with an Al KR monochromator X-ray source running at 15 kV and 23.3 mA, a hemispherical electron energy analyzer, and a multi-channel detector. The test chamber pressure was maintained below $2\times10^{-9}$ Torr during spectral acquisition. A low-energy electron flood gun was used to neutralize the possible surface charge. The XPS binding energy (BE) was internally referenced to the aliphatic C(1s) peak (BE, 284.6 eV). Survey spectra were acquired at an analyzer pass energy of 93.9 eV and BE resolution of 0.8 eV, while high resolution spectra were acquired with a pass energy of 23.5 eV and BE resolution of 0.05 eV. The takeoff angle is defined as the angle between the surface normal and detector. High-resolution spectra were resolved by fitting each peak with Guassian-Lorentz functions after subtracting the background using the PHI data processing software package under the constraint of setting a reasonable BE shift and characteristic full width at half-maximum range. Atomic concentrations were calculated by normalizing peak areas to the elemental sensitivity factor data provided by the PHI database.

REFERENCES FOR EXAMPLE 3

(1) Dong, Y.; Li, Y.; Wang, C.; Cui, A.; Deng, Z. J. Colloid. Interface Sci. 2001, 243, 85-89.

(2) Ram, S.; Mitra, C. Mater. Sci. Eng. 2001, A304-306, 805-809.

(3) Musa, A. O.; Akomolafe, T.; Carter, M. Solar Energy Mater. Solar Cells 1998, 51, 305-316.

(4) Bohannan, E. W.; Shumsky, M. G.; Switzer, J. A. Chem. Mater. 1999, 11, 2289-2291.

(5) Deki, S.; Akamatsu, K.; Yano, T.; Mizuhata, M.; Kajinami, A. J. Mater. chem. 1998, 8, 1865.

(6) Caswell, N.; Yu, P. Y. Phys. Rev. B. 1982, 25, 5519.

(7) Borgohain, K.; Murase, N.; Mahamuni, S. J. Appl. Phys. 2002, 92, 1292.

(8) Amikura, H.; Masumi, T. J. Phys. Soc. Jpn. 1995, 64, 2684.

(9) Trebin, H. R.; Cummins, H. Z.; Birman, J. L. Phys. Rev. B. 1981, 23, 597.

(10) Gastev, S. V.; Kaplyanskii, A. A.; Sokolov, N. S. Solid State Commun. 1982, 42, 389.

(11) Snoke, D. W.; Wolfe, J. P.; Mysyrowics, A. Phys. Rev. B. 1990, 41, 11171.

(12) Snoke, D. W.; Braun, D.; Cardona, M. Phys. Rev. B. 1991, 44, 2991.

(13) Goto, T.; Shen, M. Y.; Koyama, S.; Yokouchi, T. Phys. Rev. B. 1997, 55, 7609.

(14) Muramatsu, A.; Sugimoto, T. J. Colloid. Interface Sci. 1997, 189, 167-173.

(15) Ponyatovskil, E. G.; Arosimova, G. E.; Aronin, A. S.; Kulakov, V. I.; Sinitsyn, V. V. Phys. Solid State 2002, 44, 852.

(16) Mcfadyen, P.; Matijevic, E. J. Colloid. Interface Sci. 1973, 44, 95-106.

(17) Son, S. U.; Park, I. K.; Park, J.; Hyeon, T. Chem. Commun. 2004, 778-779.

(18) Gou, L.; Murphy, C. nano Lett. 2003, 3, 231.

(19) Ayyub, P.; Palkar, V. R.; Chattopadhyay, S.; Multani, M. Phys. Rev. B 1995, 51, 6135.

(20) Herhold, A. B.; Chen, C.-C.; Johnson, C. S.; Tolbert, S. H.; Alivisatos, A. P. Structural transformations and metastability in semiconductor nanocrystals, 1999; Vol. 68.

(21) Qadri, S. B.; Skelton, E. F.; Hsu, D.; Dinsmore, A. D.; Yang, J.; Gray, H. F.; Ratna, B. R. Phys. Rev. B 1999, 60, 9191.

(22) Pallkar, V. R.; Ayyub, P.; Chattopadhyay, S.; Multani, M. Phys. Rev. B. 1996, 53, 2167.

(23) Yin, M.; Gu, Y.; Kuskovsky, l. L.; Andelman, T.; Zhu, Y.; Neumark, G. F.; O'Brien, S. J. Am. Chem. Soc. 2004, 126, 6206.

(24) Yin, M.; O'Brien, S. J. Am. Chem. Soc. 2003, 125, 10180.

(25) Park, J.; An, K.; Hwang, Y.; Park, J.-G.; Noh, H.-J.; Kim, J. Y.; Park, J.-H.; Hwang, N.-M.; Hyeon, T. Nature Materials 2004, 3, 891-895.

(26) Redl, F. X.; Cho, K.-S.; Murray, C. B.; O'Brien, S. Nature 2003, 423, 968-971.

All patent applications, published patent applications, issued and granted patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

What is claimed is:

1. A method of preparing metal oxide nanoparticles, comprising:
   (a) mixing a metal acetate precursor with a non-aqueous organic solvent comprising at least one organic stabilizing ligand to form a reaction mixture;
   (b) subjecting the mixture of step (a) to a temperature greater than about 100° C. for a time sufficient to allow formation of metal oxide nanoparticles and decomposition of the metal acetate; and
   (c) extracting the metal oxide nanoparticles into a hydrocarbon solvent at a temperature lower than the temperature of step (b) by precipitation with a flocculating agent;
   wherein the metal of the metal oxide nanoparticles has an oxidation state that is the same or less than the oxidation state of the metal of the metal acetate precursor,
   wherein the metal acetate of step (a) is selected from the group consisting of iron (Fe) acetate, manganese (Mn) acetate, cobalt (Co) acetate, ruthenium (Ru), copper (Cu) acetate, scandium (Sc) acetate, titanium (Ti) acetate, vanadium (V) acetate, chromium (Cr) acetate, chromium (Cr) acetate dimer, molybdenum (Mo) acetate, molybdenum (Mo) acetate dimer, yttrium (Y) acetate, zirconium (Zr) acetate, hafnium (Hf) acetate, and nickel (Ni) acetate.

2. The method according to claim 1, wherein the organic solvent of step (a) comprises a trialkylamine.

3. The method according to claim 2 wherein the solvent is trioctylamine.

4. The method according to claim 1, wherein the organic stabilizing ligand is selected from the group consisting of sulfonic acid, sulfinic acid, phosphonic acid, phosphoric acid, a carboxylic acid and a thiol.

5. The method according to claim 1, wherein the organic stabilizing ligand is oleic acid.

6. The method according to claim 1, wherein the temperature of step (b) is from about 50° C. to about 400° C.

7. The method according to claim 6, wherein the temperature of step (b) is from about 250° C. to about 400° C.

8. The method according to claim 1, wherein the nanoparticles of step (c) are selected from the group consisting of zinc oxide nanoparticles, iron oxide nanoparticles, manganese oxide nanoparticles, cobalt oxide nanoparticles, ruthenium oxide nanoparticles, copper oxide nanoparticles, scandium oxide nanoparticles, titanium oxide nanoparticles, vanadium oxide nanoparticles, chromium oxide nanoparticles, molybdenum oxide nanoparticles, yttrium oxide nanoparticles, zirconium oxide nanoparticles, hafnium oxide nanoparticles, nickel oxide nanoparticles, or a mixture thereof.

9. The method according to claim 8, wherein the nanoparticles are selected from zinc oxide, manganese oxide, or iron oxide nanoparticles.

10. The method according to claim 1, wherein, in step (a), the anhydrous metal acetate precursor is mixed with the organic solvent to form the reaction mixture at room temperature.

11. The method according to claim 1, wherein, in step (b), the mixture is brought to said temperature in a time period of from about 10 minutes to about 30 minutes.

12. The method according to claim 11, wherein, in step (b), the mixture is brought to said temperature in a time period of from about 10 minutes to about 15 minutes.

13. The method according to claim 1, wherein the mixture of step (b) is maintained at said temperature for about 45 minutes to about 1 hour to allow the formation of nanoparticles.

14. The method according to claim 1, wherein in step (c) the hydrocarbon solvent is selected from pentane, hexane, heptane, octane, or dodecane.

15. The method according to claim 1, wherein in step (c) the flocculating agent comprises a polar organic solvent.

16. The method according to claim 15, wherein the polar organic solvent is methanol, ethanol, propanol, or butanol.

17. The method according to claim 1, wherein, in step (c), the nanoparticles are extracted into an alkane solvent by precipitation with an alcohol or ketone.

18. The method according to claim 17, wherein the nanoparticles are extracted into hexane solvent by precipitation with ethanol, followed by centrifugation and redispersion in hydrocarbon solvent.

19. The method according to claim 1, wherein the extracted nanoparticles of step (c) are stable, monodisperse, and have uniform size.

20. The method according to claim 1, wherein the extracted nanoparticles of step (c) have an organic outside coating.

21. The method according to claim 1, wherein the nanoparticles have a size from about 3 nm to about 20 nm.

22. The method according to claim 1, wherein, following step (b), the organic solvent is subjected to a second temperature of at least about 100° C. for a time sufficient to obtain nanocrystals having a specific diameter of from about 10 nm to about 40 nm.

23. The method according to claim 1, further comprising the step of subjecting the extracted metal oxide nanoparticles obtained in step (c) to oxidation to obtain further oxidized metal oxide nanoparticles.

24. Monodisperse and stable nanoparticles produced by the method according to claim 1.

25. The method of claim 24, further comprising adding the monodisperse and stable nanoparticles to other ingredients to form a composition, wherein the composition is for use in the preparation of a formulation to prevent, reduce, retard, ameliorate, or eliminate photodamage and/or photoaging in a human or animal due to exposure to sunlight.

26. The method of claim 24, further comprising adding the monodisperse and stable nanoparticles to other ingredients to form a composition, wherein the composition is for use in the preparation of a pharmaceutical formulation, drug formulation, or medicament, and further comprising a physiologically acceptable carrier, vehicle, or excipient.

27. The method of claim 24, further comprising adding the monodisperse and stable nanoparticles to other ingredients to form a composition, wherein the composition is for use in the preparation of a cosmetic formulation.

28. The method of claim 24, further comprising adding the monodisperse and stable nanoparticles to other ingredients to form a composition, wherein the composition is a cosmetic formulation, wherein the cosmetic formulation is selected from makeups, topical skin care products, soaps, powders, lotions, creams, ointments, sunblocks, sunscreens, conditioners, shampoos, fragrances, deodorants, deodorizers, hair colors, or hair dyes.

29. A method of preparing iron oxide nanoparticles, comprising:
 (a) mixing an iron acetate precursor with an organic solvent comprising at least one organic stabilizing ligand to form a reaction mixture;
 (b) subjecting the mixture of step (a) to a temperature of from about 200° C. to about 260° C. for a time sufficient to allow formation of iron oxide nanoparticles and decomposition of the iron acetate; and
 (c) extracting the iron oxide nanoparticles of step (b) into a hydrocarbon solvent at a temperature lower than the temperature of step (b) by precipitation with a flocculating agent;
 wherein the iron of the iron oxide nanoparticles has an oxidation state that is the same or less than the oxidation state of the iron of the iron acetate precursor.

30. A method of preparing manganese oxide nanoparticles, comprising:
 (a) mixing a manganese acetate precursor with an organic solvent comprising at least one organic stabilizing ligand to form a reaction mixture;
 (b) subjecting the mixture of step (a) to a temperature of from about 300° C. to about 350° C. for a time sufficient to allow formation of monodisperse manganese oxide nanoparticles and decomposition of the manganese acetate; and
 (c) extracting the manganese oxide nanoparticles of step (b) into a hydrocarbon solvent at a temperature lower than the temperature of step (b) by precipitation with a flocculating agent;
 wherein the manganese of the manganese oxide nanoparticles has an oxidation state that is the same or less than the oxidation state of the manganese of the manganese acetate precursor.

31. A method of preparing monodisperse, stable metal oxide nanoparticles, comprising:
 (a) mixing a metal acetate precursor with a non-aqueous organic solvent comprising at least one organic stabilizing ligand to form a reaction mixture;
 (b) subjecting the mixture of step (a) to a temperature of from about 150° C. to about 400° C. for a time sufficient to allow formation of metal oxide nanoparticles and decomposition of the metal acetate; and
 (c) extracting the metal oxide nanoparticles into a hydrocarbon solvent at a temperature of about 100° C. or lower by precipitation with a polar organic solvent;
 wherein the metal of the metal oxide nanoparticles has an oxidation state that is the same or less than the oxidation state of the metal of the metal acetate precursor,
 wherein the metal acetate of step (a) is selected from the group consisting of iron (Fe) acetate, manganese (Mn) acetate, cobalt (Co) acetate, ruthenium (Ru), copper (Cu) acetate, scandium (Sc) acetate, titanium (Ti) acetate, vanadium (V) acetate, chromium (Cr) acetate, chromium (Cr) acetate dimer, molybdenum (Mo) acetate, molybdenum (Mo) acetate dimer, yttrium (Y) acetate, zirconium (Zr) acetate, hafnium (Hf) acetate, and nickel (Ni) acetate.

32. A method of preparing monodisperse, stable metal oxide nanoparticles, comprising:
 (a) mixing a metal acetate precursor with a trialkylamine solvent comprising at least one organic stabilizing ligand comprising a long chain alkyl with one or more carboxylic acid functional groups to form a reaction mixture;
 (b) subjecting the mixture of step (a) to a temperature of from about 150° C. to about 400° C. for a time sufficient to allow formation of metal oxide nanoparticles and decomposition of the metal acetate; and
 (c) extracting the metal oxide nanoparticles into a hydrocarbon solvent at a temperature of about 100° C. or lower by precipitation with a polar organic solvent;
 wherein the metal of the metal oxide nanoparticles has an oxidation state that is the same or less than the oxidation state of the metal of the metal acetate precursor,
 wherein the metal acetate of step (a) is selected from the group consisting of iron (Fe) acetate, manganese (Mn) acetate, cobalt (Co) acetate, ruthenium (Ru), copper (Cu) acetate, scandium (Sc) acetate, titanium (Ti) acetate, vanadium (V) acetate, chromium (Cr) acetate, chromium (Cr) acetate dimer, molybdenum (Mo) acetate, molybdenum (Mo) acetate dimer, yttrium (Y) acetate, zirconium (Zr) acetate, hafnium (Hf) acetate, and nickel (Ni) acetate.

33. A method of preparing monodisperse, stable metal oxide nanoparticles, comprising:
 (a) mixing a metal acetate precursor with a trialkylamine solvent comprising at least one organic stabilizing ligand comprising a long chain alkyl with one or more carboxylic acid functional groups to form a reaction mixture;
 (b) subjecting the mixture of step (a) to a temperature of from about 250° C. to about 400° C. for a time sufficient to allow formation of metal oxide nanoparticles and decomposition of the metal acetate; and
 (c) extracting the metal oxide nanoparticles into a hydrocarbon solvent at a temperature of about 100° C. or lower by precipitation with a polar organic solvent;
 wherein the metal of the metal oxide nanoparticles has an oxidation state that is the same or less than the oxidation state of the metal of the metal acetate precursor,
 wherein the metal acetate of step (a) is selected from the group consisting of iron (Fe) acetate, manganese (Mn) acetate, cobalt (Co) acetate, ruthenium (Ru), copper (Cu) acetate, scandium (Sc) acetate, titanium (Ti) acetate, vanadium (V) acetate, chromium (Cr) acetate, chromium (Cr) acetate dimer, molybdenum (Mo) acetate, molybdenum (Mo) acetate dimer, yttrium (Y) acetate, zirconium (Zr) acetate, hafnium (Hf) acetate, and nickel (Ni) acetate.

34. The method according to any one of claim 31, 32 or 33, wherein the trialkylamine is trioctylamine.

35. The method according to any one of claim 31, 32 or 33, wherein the organic stabilizing ligand is oleic acid.

36. The method according to any one of claim 31, 32 or 33, wherein, in step (a), the anhydrous metal acetate precursor is mixed with the organic solvent to form the reaction mixture at room temperature.

37. The method according to any one of claim 31, 32 or 33, wherein, in step (b), the mixture is brought to said temperature in a time period of from about 10 minutes to about 30 minutes.

38. The method according to any one of claim 31, 32 or 33, wherein the mixture of step (b) is maintained at said temperature for a time period of from about 45 minutes to about 1 hour to allow the formation of metal oxide nanoparticles.

39. The method according to any one of claim 31, 32 or 33, wherein in step (c) the hydrocarbon solvent is selected from pentane, hexane, heptane, octane, or dodecane.

40. The method according to any one of claim 31, 32 or 33, wherein the polar organic solvent is methanol, ethanol, propanol, or butanol.

41. The method according to any one of claim 31, 32 or 33, wherein the extracted metal oxide nanoparticles of step (c) have an organic outside coating.

42. The method according to any one of claim 31, 32 or 33, wherein the nanoparticles have a size of from about 2 nm to about 20 nm.

43. Monodisperse and stable nanoparticles produced by the method according to any one of claim 31, 32 or 33.

44. A composition comprising the nanoparticles according to claim 1 for use in the preparation of a formulation to prevent, reduce, retard, ameliorate, or eliminate photodamage and/or photoaging in a human or animal due to exposure to sunlight.

45. The method of claim 1, further comprising adding the nanoparticles according to step (c) to a pharmaceutical formation, drug formulation or medicament to form a composition, wherein the composition is for use in the preparation of a pharmaceutical formulation, drug formulation, or medicament, comprising the nanoparticles and further comprising a physiologically acceptable carrier, vehicle, or excipient.

46. The method of claim 1, further comprising adding the nanoparticles according to step (c) to a cosmetic formulation to form a cosmetic formulation comprising the nanoparticles.

47. The method of claim 1, further comprising adding the nanoparticles according to step (c) to a makeup, topical skin care product, soap, powder, lotion, cream, ointment, conditioner, shampoo, fragrance, deodorant, deodorizer, hair color, or hair dye to form, a makeup, topical skin care product, soap, powder, lotion, cream, ointment, conditioner, shampoo, fragrance, deodorant, deodorizer, hair color, or hair dye, respectively, comprising the nanoparticles.

48. The method of any one of claim 1, 29, 30, 31, 32 or 33, wherein the metal acetate precursor is anhydrous.

* * * * *